(12) United States Patent
Karaolis

(10) Patent No.: US 8,367,716 B2
(45) Date of Patent: Feb. 5, 2013

(54) METHOD FOR ATTENTUATING VIRULENCE OF MICROBIAL PATHOGENS AND FOR INHIBITING MICROBIAL BIOFILM FORMATION

(76) Inventor: David K. R. Karaolis, Baltimore, MD (US)

( * ) Notice: Subject to any disclaimer, the term of this patent is extended or adjusted under 35 U.S.C. 154(b) by 364 days.

(21) Appl. No.: 10/565,591

(22) PCT Filed: Jul. 22, 2004

(86) PCT No.: PCT/US2004/023498
§ 371 (c)(1),
(2), (4) Date: Oct. 6, 2006

(87) PCT Pub. No.: WO2005/030186
PCT Pub. Date: Apr. 7, 2005

(65) Prior Publication Data
US 2007/0244059 A1    Oct. 18, 2007

Related U.S. Application Data

(60) Provisional application No. 60/490,029, filed on Jul. 28, 2003.

(51) Int. Cl.
*A01N 43/26* (2006.01)
*A61K 31/385* (2006.01)

(52) U.S. Cl. .................................................. 514/440
(58) Field of Classification Search .............. 514/440
See application file for complete search history.

(56) References Cited

U.S. PATENT DOCUMENTS

| | | | |
|---|---|---|---|
| 5,312,813 A * | 5/1994 | Costerton et al. ............... | 514/29 |
| 5,547,941 A | 8/1996 | Battistini et al. | |
| 2002/0091074 A1 * | 7/2002 | Wooley et al. ................... | 514/1 |
| 2002/0169288 A1 * | 11/2002 | Hook et al. ....................... | 530/350 |

OTHER PUBLICATIONS

By Mayer et al 1991 Proc. Natl. Acad. Sci USA vol. 88 pp. 5472-5476.*
Ross et al. Biol. Chem. 265 No. 31 (1990) 18933-18943.*
Parsek et al 2003. Bacterial biofilms: an emerging link to disease pathogenesis. Annu. Rev. Microbiol. 57:677-701.*
Reisner et al 2006 Journal of Bacteriology vol. 188 No. 10 pp. 3572-3581.*
Stratton 2006 Med. Clin North Am vol. 6 pp. 1077-1088.*
Bowie et al (Science, 1990, 247:1306-1310).*
Steinberger et al 1999 FEBS Letters vol. 444 pp. 125-129.*
Galperin, M. Y. et al., "Novel domains of the prokaryotic two-component signal transduction systems", FEMS Microbiology Letters, (2001), vol. 203, No. 1, pp. 11-21.
Jenal, U., "Cyclic di-guanosine-monophosphate comes of age: a novel secondary messenger involved in modulating cell surface structures in bacteria", Current Opinion in Microbiology, (2004), vol. 7, No. 2, pp. 185-191.
Rashid, M. J. et al., "Identification of genes involved in the switch between the smooth and rugose phenotypes of Vibrio cholerae", FEMS Microbiology Letters, (2003), vol. 227, No. 1, pp. 113-119.

* cited by examiner

*Primary Examiner* — Gary Nickol
*Assistant Examiner* — Nina Archie
(74) *Attorney, Agent, or Firm* — Browdy and Neimark, PLLC

(57) ABSTRACT

The present invention relates to the use of the cyclic dinucleotide c-di-GMP and cyclic dinucleotide analogues thereof in a method for attenuating virulence of a microbial pathogen or for inhibiting or reducing colonization by a microbial pathogen. This method further inhibits microbial biofilm formation and is capable of treating bacterial infections. The microbial colonization or biofilm formation inhibited or reduced may be on the skin or on nasal or mucosal surface. The microbial colonization or biofilm formation inhibited can also be on the surfaces of medical devices, especially those in close contact with the patient, as well on the surfaces of industrial and construction material where microbial colonization and biofilm formation is of concern.

26 Claims, 9 Drawing Sheets

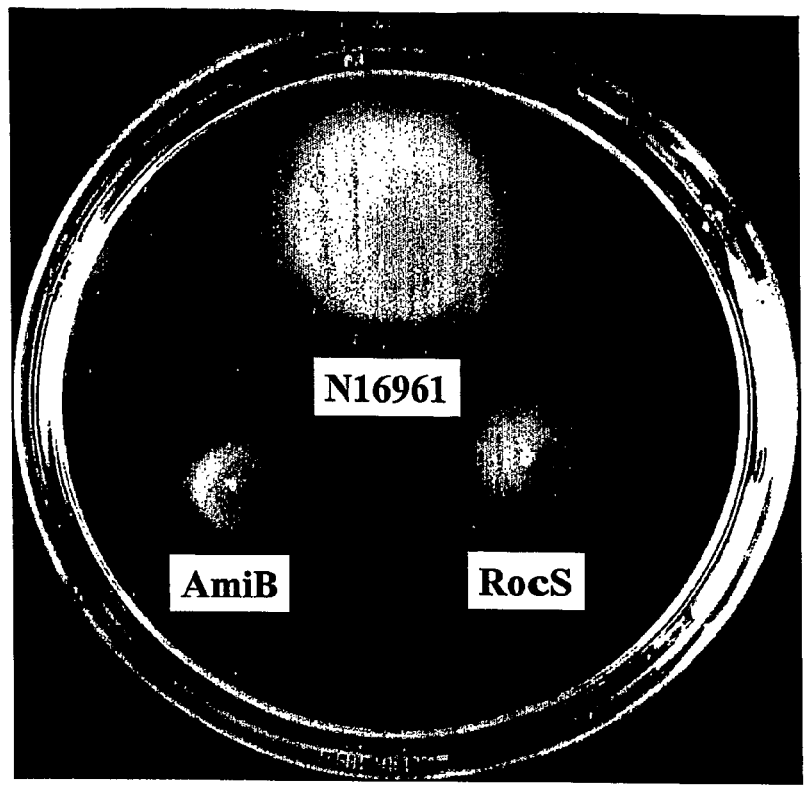
FIG. 3
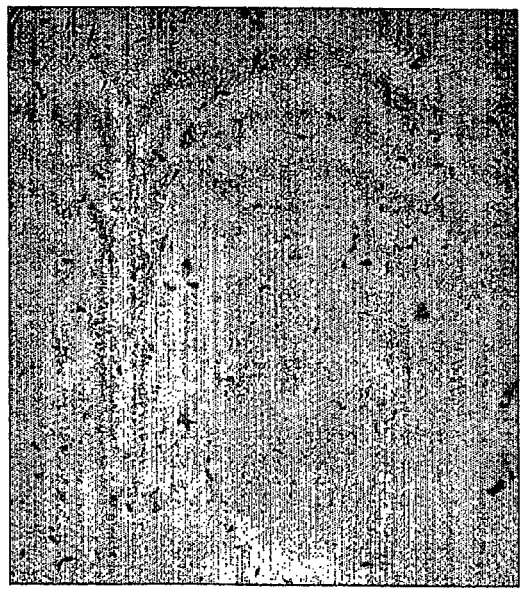
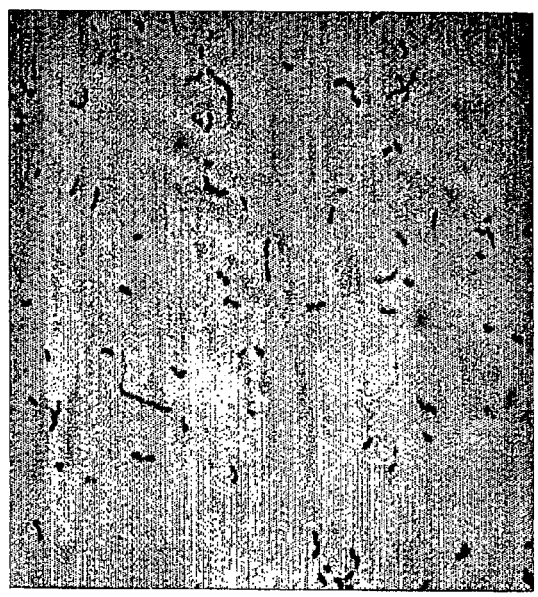
FIG. 4A  FIG. 4B

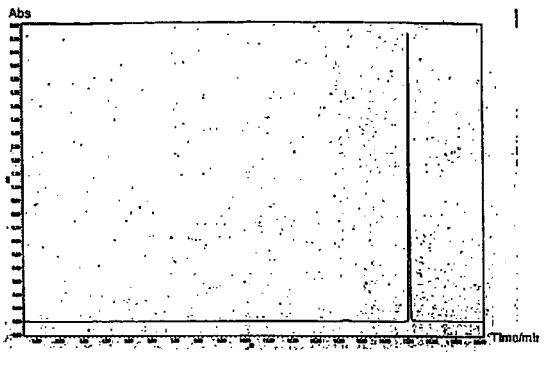
FIG. 5A
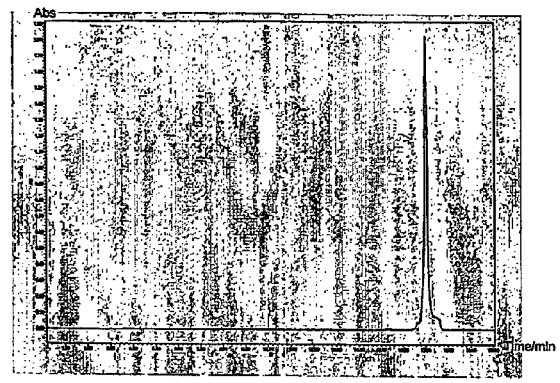
FIG. 5B
FIG. 6A  FIG. 6B
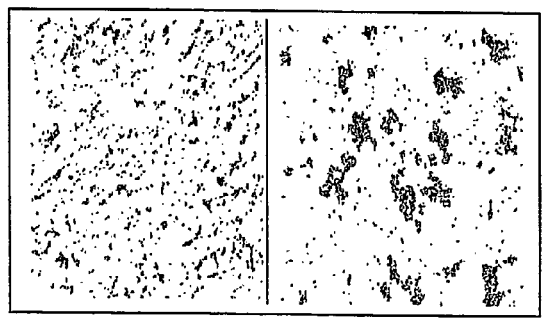
FIG. 6C  FIG. 6D
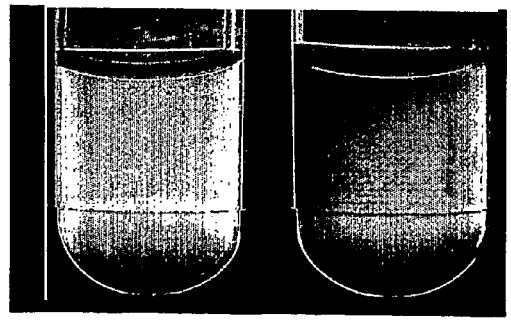
FIG. 6E  FIG. 6F

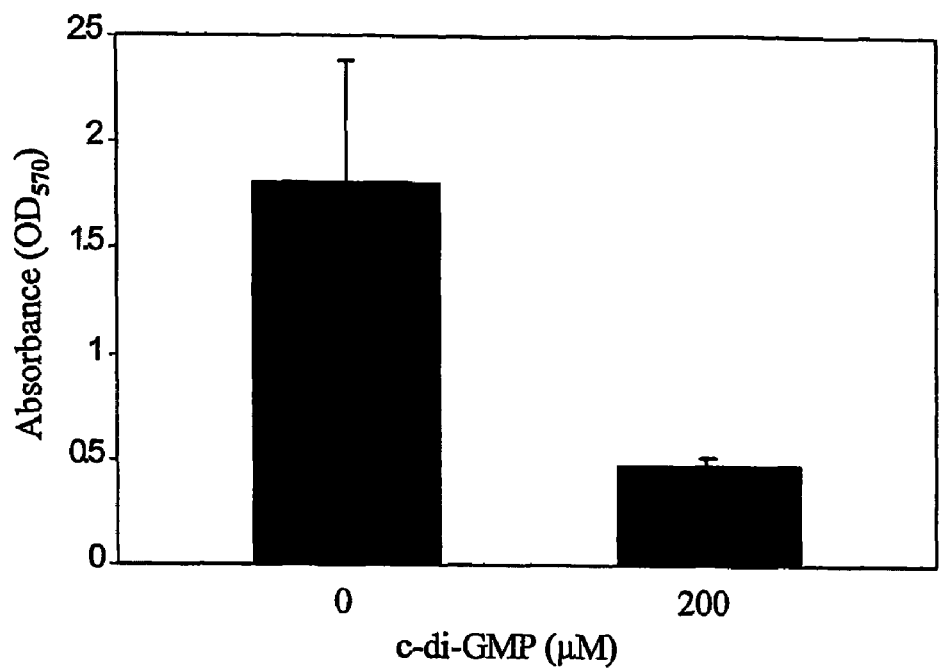
FIG. 10
FIG. 11A  FIG. 11B

METHOD FOR ATTENUATING VIRULENCE OF MICROBIAL PATHOGENS AND FOR INHIBITING MICROBIAL BIOFILM FORMATION

BACKGROUND OF THE INVENTION

1. Field of the Invention

The present invention relates to the use of cyclic dinucleotides to attenuate virulence of microbial pathogens and to inhibit biofilm formation, thereby controlling microbial colonization or infections caused by a wide variety of microbial species.

2. Description of the Related Art

Cholera is an important diarrheal disease of humans that results in significant morbidity and mortality (Pollitzer, 1959; and Kaper et al., 1995). Cholera affects more than 75 countries and every continent (Communicable Disease Surveillance and Response, World Health Organization, who.org). Cholera is acquired by drinking fecally contaminated food or water containing pathogenic *Vibrio cholerae* that can colonize the small intestine and release *cholera* toxin (CT) resulting in massive secretory diarrhea and death if untreated (Kaper et al., 1995). Because of its high death-to-case ratio, persistence in water supplies and its ability to occur in explosive epidemic form, *cholera* is a public health concern. Furthermore, because of the potential threat of weaponized *V. cholerae* to the food and water supply, it is a priority organism in biodefense research. The threat to the economy, environment and human health is also highlighted by the finding that *V. cholerae* has the potential to be transported internationally and invade new regions through the ballast water of ships (McCarthy et al., 1994). *V. cholerae* is known to persist in the environment, however, the factors promoting the environmental persistence of *V. cholerae* are not well understood.

*V. cholerae* can alter its phenotype and reversibly switch from EPSoff (smooth colony morphology) to EPSon (rugose colony morphology) in which the cells are embedded in extracellular polysaccharide or rugose exopolysaccharide (rEPS) and display a wrinkled "rugose" colony morphology (FIGS. 1A and 1B) and an associated biofilm (White, 1940 and Rice et al., 1993). The switch to EPSon and the rugose phenotype promotes biofilm formation (Rice et al., 1993; Morris et al., 1996; and Watnick et al., 1999). Importantly, EPS is essential for *V. cholerae* biofilm formation. The rugose variant is highly chlorine resistant and shows increased resistance to killing by acid, UV light and complement-mediated serum bactericidal activity (Rice et al., 1993; Morris et al., 1996; and Yildiz et al., 1999). Therefore, switching to EPSon and the rugose phenotype might be important in niche specialization and in promoting survival and fitness in particular environments. Rugose strains are virulent and cause fluid accumulation in rabbit ileal loops, produce diarrhea in human volunteers and are highly resistant to complement-mediated bactericidal activity (Rice et al., 1993; Morris et al., 1996; and Yildiz et al., 1999). The rugose or wrinkled colony phenotype consisting of aggregating cells has been reported in *S. enterica Enteritidis* (Petter, 1993), *S. enterica Typhimunium* (Anriany et al., 2001), *V. parahaemolyticus* (Güvener et al., 2003), *P. aeruginosa* (Parsek, 2003), and *Enterobacter sakazakii* (Farmer et al., 1980). Research by the laboratory of the present inventor and others has also shown that production of *V. cholerae* EPS is linked to the type II general extracellular protein secretion pathway which is also involved in secretion of important virulence factors (Ali et al., 2000; Davis et al., 2000).

The vps (*Vibrio polysaccharide*) gene cluster in *V. cholerae* carries the structural genes for the biosynthesis of rEPS (Yildiz et al., 1999). The vps gene cluster is thought to be comprised of two closely located but separate operons in which vpsA and vpsL represent the first genes of each operon (Yildiz et al., 1999 and 2001). Transcription of vpsA and vpsL is regulated by VpsR (a homolog of σ54 transcriptional activators) by a mechanism that is not well understood (Yildiz et al., 2001). VpsR has high homology to NtrC, AlgB and HydG bacterial enhancer-binding protein that activates transcription after phosphorylation of its receiver domain by an associated sensor kinase protein (Kern et al., 1999). Previous studies have found that HapR in some *V. cholerae* strains is linked to the rugose phenotype by some unknown mechanism (Jobling et al., 1997) and CytR can repress transcription of vps genes and the associated biofilm formation (Haugo et al., 2002). The present inventor has also found that switching to the rugose phenotype in *V. cholerae* is independent of ToxT, LuxS and RpoS (Ali et al., 2002). However, the molecular basis underlying switch from the smooth to the rugose phenotype of *V. cholerae* is still not well understood.

Early studies on the rugose phenotype of *V. cholerae* were impeded by the very low frequency of switching to EPSon and the rugose phenotype under the conditions tested (Morris et al., 1996; Yildiz et al., 1999; and Wai et al., 1998). The laboratory of the present inventor recently identified conditions that promote the rapid shift (up to ~80%) to the rugose phenotype in a process called high frequency rugose production (HFRP) (Ali et al., 2002). It was found that there are differences in the expression and stability of the phenotype between epidemic strains and that the ability to switch at high frequency was more common in epidemic *V. cholerae* strains than in nonpathogenic strains (Ali et al., 2002). This suggests that the ability to switch to the rugose phenotype is important in *V. cholerae* and might provide an adaptive advantage under specific conditions.

Biofilms are the primary mode of existence of many bacterial species and are central to their survival, persistence and often virulence (Costerton et al., 1995; Davey et al., 2000; Donlan, 2002 and Watnick et al., 2000). Biofilms resist environmental stresses and adverse conditions better than free-living cells, have increased nutrient availability and can better avoid immune responses (Anwar et al., 1992). A common feature of biofilms is that microorganisms are embedded in an extracellular matrix comprised mostly of EPS (Costerton et al., 1981 and Wingender et al., 1999). EPS is important for the structural and functional integrity of biofilms and determines its physicochemical and biological properties and has a role in adhesion, protection and facilitates community interactions (Wimpenny, 2000). EPS provides protection from a variety of environmental stresses such as UV radiation, pH shifts, osmotic shock, and desiccation.

The role of biofilms in the environmental persistence and transmission of certain pathogens is also well recognized. Like *V. cholerae* (Ali et al., 2002; Morris et al., 1996 and Yildiz et al., 1999), *Salmonella enterica* Typhimurium has the ability to form a rugose EPS-producing phenotype which has increased biofilm forming ability and is proposed to have a role in increased persistence in the environment (Anriany et al., 2001). *Salmonella enteritidis* biofilms resistant to cleaning fluids have been shown to persist for at least 4 weeks in domestic toilets after episodes of salmonellosis (Barker et al., 2000). The finding that *E. coli* and *Salmonella* biofilms can be found on sprouts may make their eradication with antimicrobial compounds difficult and therefore increasing their persistence, resulting in ingestion and infection (Fett, 2000). The importance of biofilms is also highlighted in the process of horizontal gene transfer since some results suggest that DNA exchange may be increased in bacteria that are attached to a surface and in biofilms rather than between free-swimming planktonic cells (Ehlers, 2000). This has implications in the transfer of genes encoding functions such as antibiotic resistance or virulence and overall persistence.

Clinically, biofilm formation is known to be a key factor in the establishment and persistence of several difficult to treat infections. Cystic fibrosis is caused by certain *P. aeruginosa* strains which express copious amounts of EPS and form biofilms in the lung (Davies et al., 1995; Geesey et al., 1993 and Govan et al., 1996). The EPS of these *P. aeruginosa* strains makes them recalcitrant to antimicrobial treatment. Interestingly, like the EPS of *V. cholerae* (Ali et al., 2002 and Morris et al., 1996), alginate EPS production by *P. aeruginosa* protects these strains against chlorine and may contribute to survival of these bacteria in chlorinated water systems (Grobe et al., 2001). Another example of a biofilm-mediated infection is chronic ear infection (otitis media) (Dingman et al., 1998). Peridontitis is also another example of a biofilm-mediated disease that results from chronic inflammation of the tissue supporting the gums and can lead to tooth loss. The main microbe causing this disease is *Porphyromonas gingivalis* (Lamont et al., 1998).

The EPS matrix of biofilms has the potential to physically prevent access of certain antimicrobial agents into the biofilm by acting as an ion exchanger, thereby restricting diffusion of compounds from the external milieu into the biofilm (Goodell et al., 1985; Nichols et al., 1988 and Nickel et al., 1985). *Helicobacter pylori* produces a biofilm that appears to be important in enhancing resistance to host defense factors and antibiotics and in promoting growth under low pH conditions in vivo (Stark et al., 1999). Biofilm bacteria can be up to 1,000-fold more resistant to antibiotic treatment than the same organism grown planktonically (Gilbert et al., 1997). Clinical biofilm infections are marked by symptoms that typically recur even after repeated treatments with antibiotics. Moreover, biofilm infections are rarely resolved by the host's immune system (Costerton et al., 1999). Bacterial biofilms on prosthetic valves are the leading cause of endocarditis in patients who have undergone heart valve replacement. Among patients who develop these infections, the mortality rate is as high as 70% (Hyde et al., 1998). Millions of catheters (e.g., central line, intravenous, and urinary catheters) are inserted into patients every year, and these implants serve as a potential surface for biofilms. Overall, it is thought that upwards of 60% of all nosocomial infections are due to biofilms. These biofilm-based infections can increase hospital stays by up to 2-3 days and cost upwards of $1 billion per year in added costs (Archibald et al., 1997).

*Staphylococcus aureus* is another biofilm-forming bacteria that has long been recognized as an important human and animal pathogen (Archer, 1998; Hermans et al., 2003; Kluytmans et al., 1997 and Sutra et al., 1994). *S. aureus* can be found on the skin and mucosal surfaces of humans, particularly the anterior nares. If followed over time, ~20% of the human population are persistent carriers; ~60%, intermittent carriers while ~20% of the population will never be colonized (Peacock et al., 2001). *S. aureus* is a common cause of both community-acquired and hospital-acquired infections. In a recent population-based active surveillance study from Canada, the annual incidence of invasive *S. aureus* infection was 28.4 per 100,000 population (Laupland et al., 2003). Certain populations including patients with indwelling medical devices such as vascular catheters, patients on hemodialysis, patients who use intravenous drugs, patients with dermatologic disease and diabetes mellitus have higher rates of colonization than the general population (Kirmani et al., 1978; Tuazon et al., 1975 and 1974). The *S. aureus* carrier state is clinically important because a carrier is at risk for infection with the colonizing strain. Studies in patients on dialysis, patients with HIV infection and patients with bloodstream infection support the hypothesis that *S. aureus* isolates causing infection are endogenous in origin when strains are examined by molecular typing (Ena et al., 1994; Luzar et al., 1990; Nguyen et al., 1999; von Eiff et al., 2001 and Yu et al., 1986). Hence, ways to inhibit or reduce *S. aureus* carriage and colonization are needed.

According to the Center for Disease Control and Prevention's National Nosocomial Infection Surveillance system, *S. aureus* is particularly a common cause of nosocomial infections and is the most common cause of surgical site infection and the second most common cause of nosocomial bacteremia (National Nosocomial Infections Surveillance (NNIS) Report, 1998). The overall number of *S. aureus* infections in intensive care units increased from 1987 to 1997 with the majority of the increase due to *S. aureus* isolates resistant to methicillin (Lowry, 1998). *S. aureus* is often resistant to multiple antibiotics. Infections caused by methicillin- and multiple antibiotic resistant *S. aureus* (MRSA) are particularly difficult to treat and MRSA infections are often associated with higher mortality and increased healthcare costs than methicillin-sensitive strains (Cosgrove et al., 2003).

*S. aureus* is also a common cause of intramammary infections (IMI) in lactating females and often results in chronic mastitis with annual losses in the dairy industry associated with subclinical mastitis in dairy cows across the U.S. being estimated at approximately $1 billion (Ott, 1999). The drug of choice for infections due to methicillin-resistant *S. aureus* (MRSA) is vancomycin, although this antibiotic is given as a last line of treatment.

Like other bacterial species, biofilm formation is known to be a key factor in the establishment and persistence of staphylococcal infections. Bacterial cells in biofilms can be up to 1,000-fold more resistant to antibiotic treatment than the same cells grown planktonically. Consistent with this observation, biofilm formation on tissues or on medical devices is an important first step in the pathogenesis of *S. aureus* infection of humans and animals (Bradley et al., 1991; Cole et al., 2001; Cucarella et al., 2001, 2002 and 2004; Götz, 2002; Huang et al., 2003; Kluytmans et al., 1997; Mest et al., 1994; Muder et al., 1991; Peacock et al., 2001; Pujol et al., 1996; and Roghmann et al., 2001). Overall, it is thought that upwards of 60% of all nosocomial infections involve biofilms. These biofilm-based infections can increase hospital stays by up to 2-3 days and cost upwards of $1 billion per year in added costs. Although the risk of infection is high in people colonized with *S. aureus*, there is another compelling reason to prevent colonization and biofilm formation, which is to prevent the transmission of *S. aureus* to others (Muto et al., 2003). MRSA does not spontaneously emerge from existing methicillin-susceptible *S. aureus*. The majority of people with MRSA colonization acquire MRSA through exposure to the hands of healthcare workers transiently colonized with MRSA from prior contact with an MRSA infected or colonized patient (Muto et al., 2003). Infection control measures such as isolation and handwashing reduce but do not eliminate this transmission, although compliance with these policies is often low (Richet et al., 2003). Decolonization regimens, as an approach to controlling transmission to others, have generally been unsuccessful as the eradication of MRSA is generally only temporary. Therefore, the development of novel intervention strategies that prevent or inhibit colonization and biofilm formation are needed.

Cyclic nucleotides, such as cAMP and CGMP, are well recognized as important low-molecular weight signaling molecules in eukaryotes. In bacteria, while cAMP has a role in alleviating glucose catabolite repression (Jackson et al., 2002; Notley-McRobb et al., 1997), cGMP has not been shown to act as a signaling molecule. However, another guanosine nucleotide, the cyclic dinucleotide c-di-GMP (also known as 3',5'-cyclic diguanylic acid, cyclic diguanylate, cyclic diguanosine monophosphate, cyclic bis(3'→5')diguanylic acid, cyclic diguanylic acid, cGpGp, and c-GpGp)

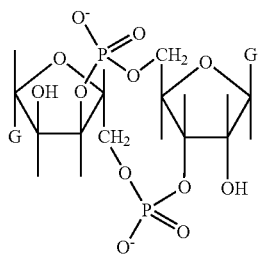

where G in the above structure is guanine, has been reported to be an intracellular bacterial signaling molecule in a few species and whose structure is known and consists of two cGMP molecules bound head-to-tail (Jenal, 2004 and Ross et al., 1991). c-di-GMP was first identified in *Acetobacter xylinum* (renamed *Gluconacetobacter xylinum*) and shown to regulate cellulose production in this species (Amikam et al., 1989; Mayer et al., 1991; Ross et al., 1990 and 1991). The exact molecular mechanism remains unclear but regulation in *G. xylinum* appears to involve c-di-GMP binding to a membrane protein that activates gene expression. Cellulose production appears to be modulated by the opposing effects of two proteins with GGDEF domains, diguanylate cyclase (Dgc) and c-di-GMP phosphodiesterase (PdeA), each controlling the level of c-di-GMP in the cell. Thus, c-di-GMP is thought to be a signaling molecule.

Based on studies by the laboratory of the present inventor and others, it is now becoming increasingly reported that biofilm formation in many pathogens including *Vibrio cholerae*, *Yersinia pestis*, *Salmonella enteritidis Typhimurium* and *Pseudomonas aeruginosa* is associated with GGDEF proteins (Bomchil et al., 2003; D'Argenio et al., 2002; Jones et al., 1999 and Römling et al., 2000).

The increasing emergence of antimicrobial resistance in bacterial pathogens and the importance of colonization and biofilm in the infection process requires that alternate antimicrobial strategies be developed. Until the present invention, the application of cyclic dinucleotides such as c-di-GMP for use as an antimicrobial approach in the control of biofilms and potentially infection has not been described.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a method for attenuating the virulence of a microbial pathogen or for inhibiting or reducing colonization by a microbial pathogen, regardless of whether or not the microbial pathogen is a biofilm-forming bacteria, by administering c-di-GMP or a cyclic dinucleotide analogue of c-di-GMP to a patient in need thereof. This method is capable of treating bacterial infections.

For biofilm-forming bacteria, the present method also inhibits biofilm formation or reduces its presence, i.e., the amount of pre-formed biofilm. Thus, the present invention provides a method for inhibiting biofilm formation or for reducing the amount of pre-formed biofilm and inhibiting further biofilm development to thereby treat an infection caused by a biofilm-forming bacterial pathogen.

The present invention is also directed to a method for inhibiting microbial colonization and biofilm formation and for reducing colonization and promoting biofilm dissolution (reducing pre-existing colonization and pre-formed or accumulated biofilm) on a solid surface, in particular, a solid surface of a medical device that is or comes into close contact with a patient, by exposing the solid surface with c-di-GMP or a cyclic dinucleotide analogue thereof.

A further aspect of the present invention is directed to a pharmaceutical composition containing c-di-GMP or a cyclic dinucleotide thereof as an active ingredient.

BRIEF DESCRIPTION OF THE DRAWINGS

FIG. 3 is a Swarm plate assay showing the motility of *V. cholerae* strains N16961 (wildtype), AmiB mutant (DK630) and RocS mutant (DS567). Plates contain LB media supplemented with 0.3% agar and were incubated at 37° C. for 4 h.

FIGS. 4A and 4B show the effect of an AmiB mutation on the cellular morphology of *V. cholerae* strain N16961, where wildtype cells are shown in FIG. 4A and AmiB mutant cells are shown in FIG. 4B. Note that the AmiB cells have a difference in morphology and show an increase in overall cell size and the presence of numerous cells in chains. Magnification 1000×.

FIGS. 5A and 5B show the HPLC profile of c-di-GMP. Analysis immediately after synthesis of c-di-GMP showing the purity of the product (FIG. 5A). Analysis showing the purity of c-di-GMP in 0.9% NaCl after 3 months storage at 4° C. (FIG. 5B).

FIGS. 6A-6F show the effect of c-di-GMP on *S. aureus* cell-to-cell aggregation. 24 h culture of DK825 treated with 200 μM c-di-GMP (FIG. 6A) and untreated control (FIG. 6B). Gram stain of c-di-GMP treated cells (FIG. 6C) and untreated cells (FIG. 6D). c-di-GMP treated culture of bap mutant M556 (FIG. 6E) and untreated control (FIG. 6F). Magnification in FIGS. 6C and 6D is 630×.

FIG. 10 is a graph showing quantitative biofilm analysis on the effect of c-di-GMP on S. aureus 24 h pre-formed biofilms.

FIGS. 11A and 11B show the effect of c-di-GMP treatment on S. aureus DK825 adherence to HeLa epithelial cells. FIG. 11A, untreated control culture; FIG. 11B, c-di-GMP treated culture.

DETAILED DESCRIPTION OF THE INVENTION

Figure 1A:
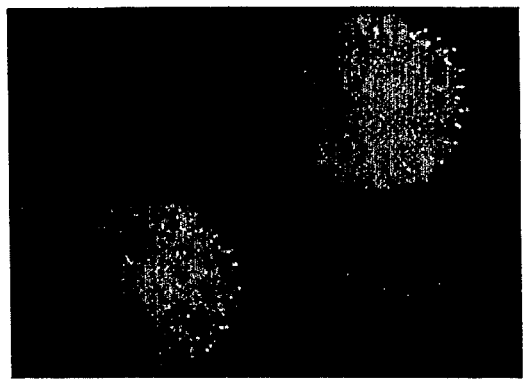
FIGS. 1A and 1B show colony morphology of the smooth (FIG. 1A) and rugose (FIG. 1B) variants of *V. cholerae* strain N16961. Colonies are shown following 48 h on LB agar plates.
Figure 1B:
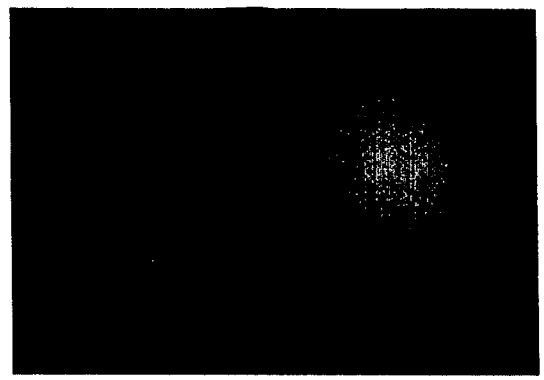

The present inventor has discovered that the cyclic dinucleotide, c-di-GMP (3', 5'-cyclic diguanylic acid, c-GpGp) is a naturally occurring signal (effector) molecule that affects microbial biofilm formation and plays a prominent role in colonization, motility and virulence of pathogenic bacteria. Pure chemically synthesized c-di-GMP is soluble and stable, and treatment of S. aureus with c-di-GMP demonstrates dramatically reduced biofilm formation and cell-to-surface interactions of S. aureus, and a striking anti-clumping effect on S. aureus cells inhibiting cell-to-cell bacterial interactions. Results obtained by the present inventor further demonstrate that c-di-GMP greatly inhibits the adherence of S. aureus to human epithelial cells, shows no significant toxicity in several cell lines, and was non-lethal in mice at biologically relevant doses. Thus, c-di-GMP inhibits biofilm formation in S. aureus and reduces or attenuates its virulence and its ability to colonize.

Further experiments have found that c-di-GMP affects the expression of numerous genes in S. aureus. For instance, quorum sensing genes were up-regulated and genes associated with toxin production, virulence, adhesion and colonization were down-regulated. These results are consistent with the role of quorum sensing genes as regulators with known roles in virulence, toxin, colonization and biofilm-associated genes, and further support the finding that c-di-GMP attenuates biofilm formation, colonization, cell clumping, toxin activity and virulence.

Bacterial cells have the ability to control expression of specific genes by secreting low molecular weight signaling molecules in association with the growth phase in a process called quorum sensing. Physiological processes controlled by quorum sensing occur in diverse species of bacteria and include bioluminescence, antibiotic synthesis, pathogenicity or virulence, protein secretion, capsular exopolysaccharide synthesis, biofilm formation and motility (Miller et al., 2001; Schander et al., 2001; Whitehead et al., 2001). In V. cholerae, biofilm formation and several other phenotypes important for virulence are known to be regulated by small signaling molecules in quorum sensing (Hammer et al., 2003; Miller et al., 2002; Zhu et al., 2002). However, c-di-GMP has not been previously identified as such a signaling molecule for quorum sensing. Controlling cell density and virulence is one of the prominent features of quorum sensing and compounds that cause defects in quorum sensing would have antibacterial activity. Accordingly, one aspect of the present invention provides a method for using c-di-GMP or cyclic dinucleotide analogues thereof to disrupt or inhibit quorum sensing communication regulatory systems in pathogenic bacteria.

From the results with S. aureus, it is expected that c-di-GMP is a universal signaling molecule in bacteria (regardless of whether or not the bacteria is a biofilm-forming bacteria) and therefore is also involved in such physiological processes as biofilm formation, toxin production, colonization and virulence in pathogenic bacteria. The present invention provides a method for attenuating the virulence of a microbial pathogen or for inhibiting or reducing colonization by a microbial pathogen which involves administering to a patient in need thereof, i.e., a patient exposed to, colonized by, or infected with a microbial pathogen, an effective amount of c-di-GMP or a cyclic dinucleotide analogue of c-di-GMP. Thus, by attenuating the virulence of the microbial pathogen, the present method is able to treat bacterial infections, either by using c-di-GMP (or a cyclic dinucleotide thereof) alone or synergistically in combination with another antibiotic/antimicrobial agent. For instance, the inhibition of biofilm formation would certainly make a pathogenic bacteria much more susceptible to the action of another antibiotic/antimicrobial agent, such as those conventionally used to treat pathogen-specific infections. The terms "treatment", "treating" and "to treat" are intended to not only be directed to active or established bacterial infections but also to inhibiting the initial stages of pathogenesis leading to infection.

As a preferred embodiment, the present method inhibits biofilm formation in a microbial pathogen for which the formation of a biofilm is critical to its pathogenicity, i.e., its virulence and its ability to colonize. For S. aureus, c-di-GMP is administered to a patient in need thereof to inhibit S. aureus colonization and biofilm formation (or reduce the colonization and biofilm already formed) and to treat an S. aureus infection. S. aureus is known to cause a wide variety of human and animal infections including, but not limited to, impetigo, mastitis, food poisoning, sepsis, osteomyelitis, arthritis, endocarditis, and pneumonia. Preliminary data in an animal (mastitis) model of infection show that c-di-GMP inhibits mastitis, an S. aureus infection of the mammary gland. Mastitis in dairy cows (bovine mastitis) is of particular concern and economic importance in the dairy industry.

Using Staphylococcus aureus as an example, the presence of S. aureus in a hospital environmental poses a risk of colonization or infection in hospital patients and personnel. Accordingly, c-di-GMP can be administered to hospital patients and personnel and new incoming patients, i.e., by spraying skin, nasal and mucosal surfaces, to inhibit *S. aureus* colonization and biofilm formation on patients and to reduce the colonization and biofilm formation of those individuals who are carriers for *S. aureus*.

Besides c-di-GMP, a cyclic dinucleotide analogue thereof which acts as a c-di-GMP agonist, i.e., having the same effect as c-di-GMP, can be used to inhibit *S. aureus* colonization and biofilm formation (or reduce pre-existing colonization and pre-formed biofilm) and to treat *S. aureus* infection.

The present inventor has further surprisingly found that, depending on the bacteria, c-di-GMP may have the effect of inhibiting biofilm formation or it may have the opposite effect of inducing or enhancing biofilm formation. For instance, in *Vibrio cholerae* and *Salmonela enteritidis*, both of which are gram-negative, c-di-GMP was found to induce or enhance biofilm formation, the opposite of its effect in *S. aureus*, a gram-positive bacteria. Thus, the effect of c-di-GMP is bacteria-specific. Nevertheless, regardless of whether c-di-GMP inhibits or whether it enhances biofilm formation, c-di-GMP still functions as a signaling effector molecule that modulates biofilm formation in bacteria.

While it is possible that the phenomenon of opposite effects of c-di-GMP in different bacteria may be due to a bacteria being gram positive versus being gram negative, this is mere speculation, which can be easily tested. The biofilm formation/inhibition assays in microtiter plates or in test tubes and flasks, as disclosed in the examples hereinbelow, are quick and easy assays for determining the effect of c-di-GMP on a particular bacteria. Moreover, these assays can just as easily accommodate the testing of many different types of bacteria, i.e., many different strains, species and/or genera, for the effect of c-di-GMP with high throughput. Thus, for any biofilm-forming bacteria, the bacteria can be easily and rapidly tested for the effect of c-di-GMP on its biofilm formation. If c-di-GMP is found to inhibit biofilm formation, then c-di-GMP or a cyclic dinucleotide analogue having c-di-GMP activity (acts as a c-di-GMP agonist) can be used to inhibit biofilm formation or to reduce pre-formed biofilm (as well as to attenuate virulence and to inhibit and reduce colonization). Likewise, if c-di-GMP instead enhances or induces biofilm formation, then a cyclic dinucleotide analogue of c-di-GMP having c-di-GMP antagonist activity (acts opposite to the effect of c-di-GMP) can be used to inhibit biofilm formation or to reduce pre-formed biofilm (as well as to attenuate virulence and to inhibit and reduce colonization). *V. cholerae* and *S. enteritidis* are non-limiting examples of bacteria in which an added cyclic dinucleotide analogue of c-di-GMP that acts as a c-di-GMP antagonist inhibits biofilm formation.

It will be appreciated by those of skill in the art that not only can the quick and easy biofilm formation/inhibition assays be used to rapidly determine the effect of c-di-GMP on the bacteria tested, but the assays can also be used to determine with only routine experimentation if a cyclic dinucleotide analogue of c-di-GMP is an agonist or antagonist of c-di-GMP. Non-limiting examples of cyclic dinucleotide analogues of c-di-GMP are presented below as compounds (I)-(XIX):

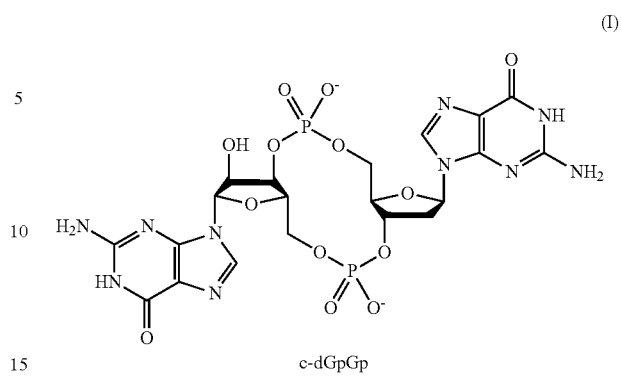

c-dGpGp (I)

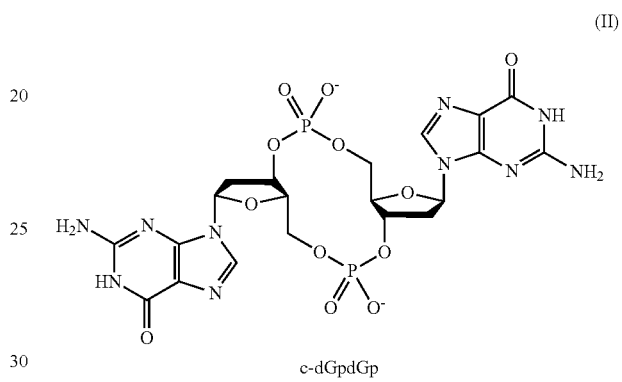

c-dGpdGp (II)

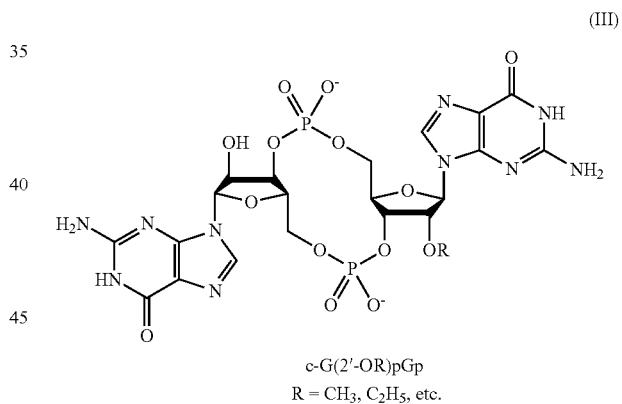

c-G(2'-OR)pGp
R = CH$_3$, C$_2$H$_5$, etc.

(III)

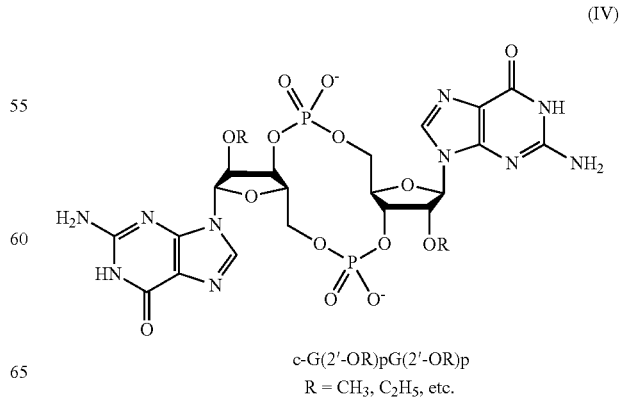

c-G(2'-OR)pG(2'-OR)p
R = CH$_3$, C$_2$H$_5$, etc.

(IV)

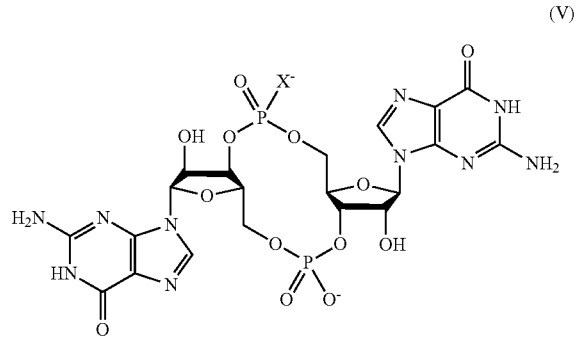
c-gpXGp
X = S, Se, BH$_3$
sterochemically pure
(V)
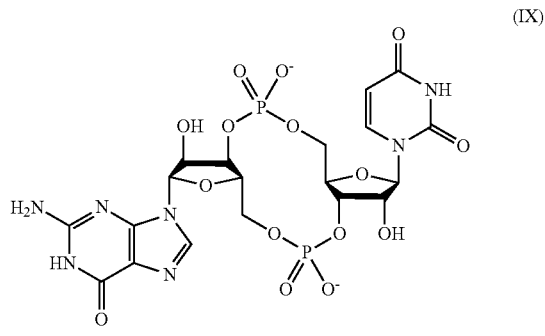
c-GpUp
(IX)
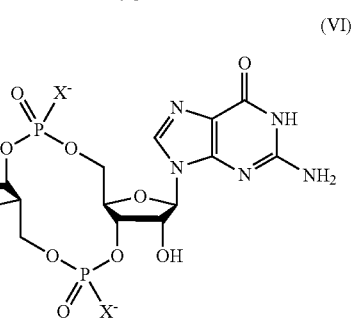
c-GpXGp
X = S, Se
sterochemically pure
(VI)
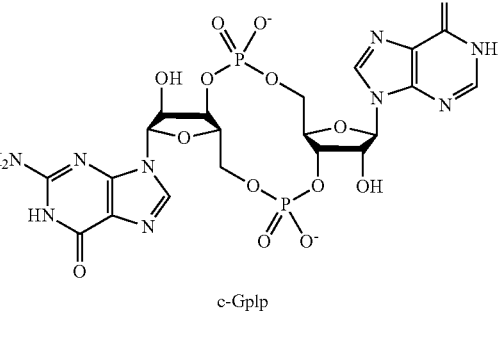
c-GpIp
(X)
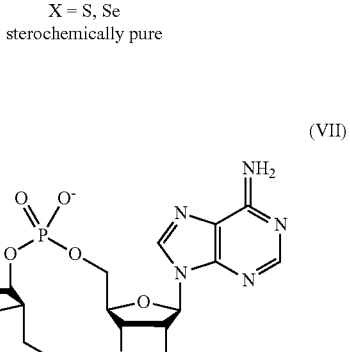
c-GpAp
(VII)
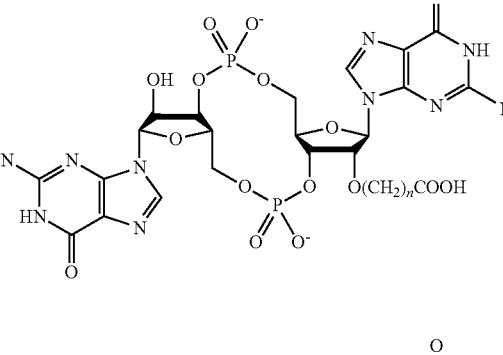
O(CH$_2$)$_n$COOH
(XI)
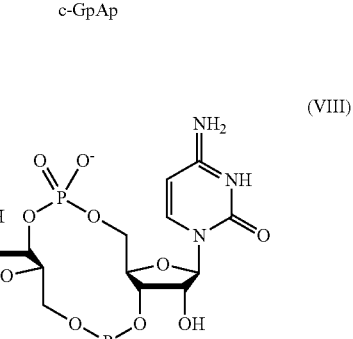
c-GpCp
(VIII)
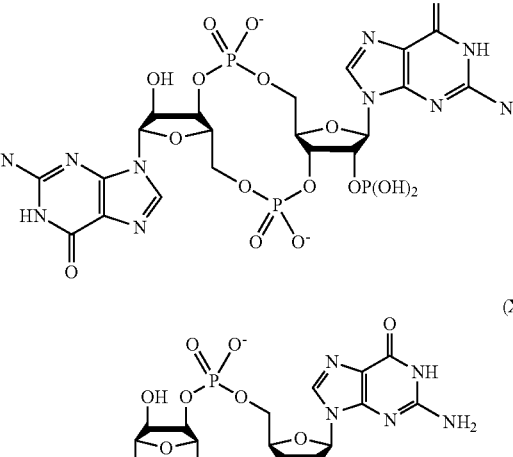
OP(OH)$_2$
(XII)
O(CH$_2$)$_n$PO(OH)$_2$
(XIII)

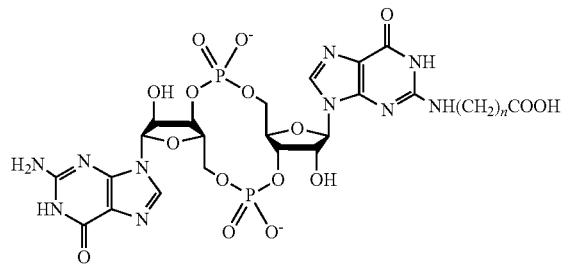

(XIV)

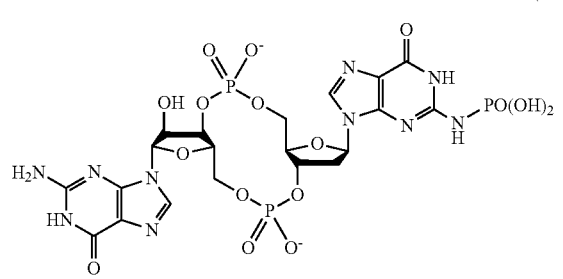

(XV)

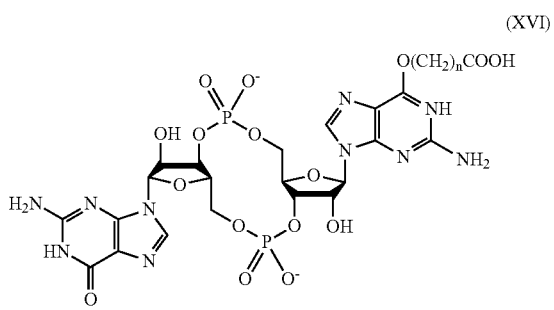

(XVI)

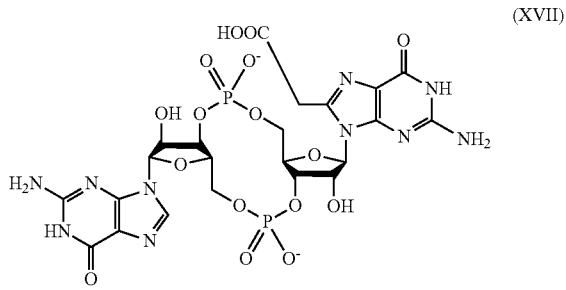

(XVII)

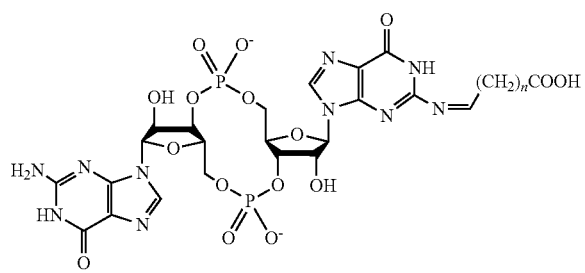

(XVIII)

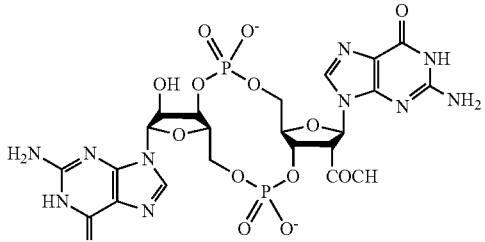

(XIX)

The above cyclic dinucleotides are only preferred embodiments of the cyclic dinucleotide analogues of c-di-GMP and are not intended to be limiting. For example, the guanine base can be substituted with other bases.

The present invention also provides a method for inhibiting microbial colonization and biofilm formation on a solid surface by exposing the solid surface to an effective amount of c-di-GMP or a cyclic dinucleotide analogue thereof to inhibit microbial colonization and biofilm formation or reduce its presence on the surface of a medical device, more preferably a medical device which is implantable or implanted in a patient, i.e., artifical joints, stents, etc., or is otherwise attached or in close contact with the patient, i.e., catheters, in-dwelling devices, intravenous tubing system, insulin pump, etc. It will also be appreciated that the solid surface can be on non-medically oriented devices, such as an industrial pipeline, and buildings or construction material where the presence of biofilm-forming bacteria can cause problems that require remediation. As the microbial biofilm formed by *S. aureus* is of particular concern on the solid surfaces of medical devices, a preferred embodiment of this aspect of the invention is to inhibit *S. aureus* biofilm formation or reduce its presence on a solid surface of a medical device by exposing the surface to an effective amount of c-di-GMP agonist. In this method, as in the method discussed above for attenuating the virulence of a microbial pathogen and for inhibiting colonization and biofilm formation, the c-di-GMP or a cyclic dinucleotide analogue thereof (either agonist or antagonist) can be selected based on the type of biofilm forming bacteria that is of concern for a particular surface. For instance, c-di-GMP can be used if *S. aureus* or a bacteria whose biofilm formation is inhibited by c-di-GMP is of main concern. In other instances, a cyclic dinucleotide analogue of c-di-GMP which acts as a c-di-GMP antagonist can be used when the bacterial biofilm formation of concern is enhanced/induced by c-di-GMP but is inhibited by an antagonist of c-di-GMP.

Those of skill in the art will appreciate that the solid surface can be exposed to c-di-GMP or a cyclic dinucleotide analogue thereof in any number of ways known to those of skill in the art. One way could be to attach or immobilize c-di-GMP or a cyclic dinucleotide analogue thereof on the surface or to incorporate c-di-GMP or a cyclic dinucleotide analogue thereof in the surface. Another way could be to flush the solid surface with a solution containing c-di-GMP or a cyclic dinucleotide analogue thereof.

Non-limiting examples of the variety of bacterial species, both pathogenic and non-pathogenic, for which the methods of the present invention are appropriate include *Vibrio harveyi, Vibrio cholerae, Vibrio parahaemolyticus, Vibrio alginolyticus, Pseudomonas fluorescens, Pseudomonas aeruginosa, Pseudomonas acidovorans, Pseudomonas alcaligenes, Pseudomonas putida, Pseudomonas syringae, Pseudomonas aureofaciens, Pseudomonas fragi, Fusobacterium nucleatum, Treponema denticola, Citrobacter freundii, Porphy-*

*romonas gingivalis, Moraxella catarrhalis, Stenotrophomonas maltophilia, Burkholderia cepacia, Aeromonas hydrophilia, Salmonella typhi, Salmonella paratyphi, Salmonella Enteritidis, Shigella dysenteriae, Shigella flexneri, Shigella sonnei, Enterobacter cloacae, Enterobacter aerogenes Yersinia enterocolitica, Yersinia pestis, Yersinia pseudotuberculosis, Yersinia inten-nedia, Bordetella pertussis, Bordetella parapertussis, Bordetella bronchiseptica, Escherichia coli, Salmonella typhimurium, Haemophilus influenzae, Haemophilus, parainfluenzae, Haemophilus haemolyticus, Haemophilus parahaemolyticus, Pasteurella multocida, Pasteurella haemolytica, Gardnerella vaginalis, Bacteroides* spp., *Clostridium difficile, Mycobacterium avium, Mycobacterium intracellulare, Mycrobacterium. leprae, Corynebacterium diplitheriae, Coxynebacterium ulcerans, Legionella pneurnophila, Listeria monocytogenes Helicobacter pylori, Bacillus subtilis, Bacillus anthracis, Borrelia burgfdorferi, Neisseria meningitidis, Neisseria gonorrhoeae, Borrelia burgdorferi, Campylobacter fetus, Campylobacterjejuni, Campylobacter coli, Deinococcus radiodurans, Mycobacterium tuberculosis, Desulfvibrio* spp., *Actinomyces* spp., *Erwinia* spp., *Xanthomonas* spp., *Xylella* spp., *Clavibacter* spp., *Desulfomonas* spp., *Desulfovibrio* spp., *Desulfococcus* spp., *Desulfobacter* spp., *Desulfobulbus* spp., *Desulfosarcina* spp., *Desulfuromonas* spp., *Acinetobacter calcoaceticus, Acinetobacter haemolyticus, Enterococcus faecalls, Streptococcus pneumoniae, Streptococcus pyogenes, Streptococcus agalactiae, Staphylococcus aureus, Staphylococcus epidermidis, Klebsiella pneumoniae, Klebsiella oxytoca, Serratia marcescens, Francisella tularensis, Morganella morganii, Providencia alcalifaciens, Providencia rettgeri, Providencia stuartii, Proteus mirabilis, Proteus vulgarls, Streptomyces* spp., *Clostridium.* spp., *Rhodococcus* spp., *Thermatoga* spp., *Sphingomonas* spp., *Zymomonas* spp., *Micrococcus* spp., *Azotobacter* spp., *Norcardia* spp., *Brevibacterium* spp., *Alcaligenes* spp., *Microbispora* spp., *Micromonospora* spp., *Methylobacterium organophilum, Pseudomonas reptilivora, Pseudomonas carragienovora, Pseudomonas dentificans, Corynebacterium* spp., *Propionibacteriurn* spp., *Xanothomonas* spp., *Methylobacterium* spp., *Chromobacteriurn* spp., *Saccharopolyspora* spp., *Actinobacillus* spp., *Alteromonas* spp., *Aeronomonas* spp., *Agrobacterium tumefaciens, Staphylococcus aureus, Staphylococcus epidennidis, Staphylococcus hominis, Staphylococcus. haemolyticus, Staphylococcus warneri, Staphylococcus cohnii, Staphylococcus saprophyticus, Staphylococcus capitis, Staphylococcus lugdunensis, Staphylococcus intemedius, Staphylococcus hyicus, Staphylococcus saccharolyticus* and *Rhizobium.* spp., and mutants thereof.

The method of the present invention for attenuating the virulence of a microbial pathogen or for inhibiting or reducing colonization by a microbial pathogen is intended to be used preferably in mammals, most preferably in humans, but can also be used in other animals such as birds.

Pharmaceutical compositions containing c-di-GMP or a cyclic dinucleotide analogue thereof for use in accordance with the method of the present invention for attenuating the virulence of the microbial pathogen or for inhibiting or reducing colonization by a microbial pathogen may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results. It will also be appreciated that c-di-GMP or a cyclic dinucleotide thereof may be used alone as the active ingredient or in combination with another antibiotic or anti-microbial agent such as those conventionally used to treat bacterial infections.

The term "carrier" refers to a diluent, adjuvant, excipient, or vehicle with which the c-di-GMP or cyclic dinucleotide thereof is administered. The carriers in the pharmaceutical composition may comprise a binder, such as microcrystalline cellulose, polyvinylpyrrolidone (polyvidone or povidone), gum tragacanth, gelatin, starch, lactose or lactose monochydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated, i.e., enterically-coated by methods well-known in the art.

Preparations for oral administration may be suitably formulated to give controlled release of the active compound.

For topical administration, c-di-GMP or a cyclic dinucleotide analogue thereof is incorporated into topically applied vehicles such as salves or ointments.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa, butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. A nasal spray, which does not require a pressurized pack or nebulizer as in an inhalation spray, can alternatively be used for intranasal administration. In the case of a pressurized aerosol, the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

A typical regiment for treatment includes administration of an effective amount over a period of several days, up to and including between one week and about six months.

The effective dose at the site of colonization, biofilm formation or infection appears to be in the micromolar range, such as between about 1 μM and 990 μM, preferably about 20 μM to 500 μM, more preferably about 100 μM to 300 μM. It is within the skill of those in the pharmaceutical art to determine with routine experimentation what dosage of c-di-GMP or a cyclic dinucleotide analogue thereof will be needed, depending on route of administration, to deliver such an effective dose to the site of biofilm formation or infection.

It is understood that the dosage of c-di-GMP or a cyclic dinucleotide analogue thereof administered in vivo may be dependent upon the age, sex, health, and weight of the recipient, kind of concurrent treatment, if any, frequency of treatment, and the nature of the pharmaceutical effect desired. The ranges of effective doses provided herein are not intended to be limiting and represent preferred dose ranges. However, the most preferred dosage may be tailored to the individual subject, as is understood and determinable by one skilled in the relevant arts. See, e.g., Berkow et al., eds., *The Merck Manual*, 16$^{th}$ edition, Merck and co., Rahway, N.J., 1992; Goodman et al., eds., Goodman and Gilman's *The Pharmacological Basis of Therapeutics*, 8$^{th}$ edition, Pergamon Press, Inc., Elmsford, N.Y. (1990); Katzung, *Basic and Clinical Pharamacology*, Appleton and Lange, Norwalk, Conn., (1992); *Avery's Drug Treatment: Principles and Practic of Clinical Pharmacology and Therapeutics*, 3$^{rd}$ edition, ADIS Press, LTD., Williams and Wilkins, Baltimore, Md. (1987), Ebadi, Pharmacology, Little, Brown and Col, Boston, (1985), which references are entirely incorporated herein by reference.

Having now generally described the invention, the same will be more readily understood through reference to the following examples which are provided by way of illustration and are not intended to be limiting of the present invention.

Example 1

Researchers studying the rugose phenotype of *V. cholerae* (and other species) have been impeded by the very low (<1%) frequency of switching between smooth (EPSoff) and rugose cells (EPSon) in vitro (Morris et al., 1996; Wai et al., 1998; White, 1940 and 1938; Yildiz et al., 1999). The laboratory of the present inventor has identified culture media and conditions, APW#3 (1% proteose peptone #3, 1% NaCl, pH 8.5), which results in a high frequency shift of smooth cells (EPSoff) to the rugose phenotype (EPSon). This process is called high frequency rugose production (HFRP) (Table 1) (Ali et al., 2002).

TABLE 1

Frequency of switching to rugose EPS production (HFRP) by *V. cholerae* strains.

| | | | % Rugose colonies | | | |
|---|---|---|---|---|---|---|
| | | | Flask | | Tube | |
| Strains[a] | Serogroup/Biotype | Source[b] | 30° C. | 37° C. | 30° C. | 37° C. |
| N16961 | O1/El Tor | C (1971) | 24-38 | 42-51 | 68-74 | 60-80 |
| C6709 | O1/ElTor | C (1991) | 1 | 23 | 15 | 70 |
| NCTC 6585 | O1/classical | C (1943) | 33-48 | 44-45 | 0 | 0 |
| AMS20A73 | O1/classical | C (1945) | 3 | 4 | 0 | 0 |
| Aldova | O37 | C (1965) | 0 | 1 | 71-72 | 23-50 |
| 1803 | non-O1 | C (1992) | 0 | 0 | 16 | 87 |
| 1837 | O139 | C (1992) | 0 | 0.2 | 0 | 0-2 |
| P44 | non-O1 | E (2000) | 12 | 0 | 0 | 2 |
| 1085-93 | O37 | E (1993) | 0 | 0 | 0.1 | 0 |
| 141-94 | O70 | E (1994) | 0 | 0 | 0.3 | 0 |
| 928-93 | O6 | E (1993) | 0 | 0.2 | 0.4 | 0 |

[a]Listed only are strains showing HFRP or spontaneous rugose colonies.
[b]C, clinical; E, environmental; Year isolated is in parentheses.

Switching to the rugose phenotype at high frequency was found to be more common in epidemic strains than in non-pathogenic strains. It was found that 6/19 toxigenic isolates (32%) that were temporally and geographically unrelated and only 1/16 unrelated nontoxigenic strains (6%) could shift to the rugose phenotype (EPSon) and showed HFRP (T test; P<0.05) (Table 1). Of all the strains tested, El Tor strain N16961 had the highest switching rates (up to 80%). Reversion, albeit at a lower frequency, from the rugose phenotype to the smooth phenotype was also found showing that phenotypic switching is conditionally transient. These features suggest the switching process might be associated with phase variation-like mechanism. While not all epidemic strains could switch at high frequency, these results showing that switching at high frequency is more correlated with toxigenic strains suggest it is important in *V. cholerae* and also suggest a link between this process and virulence. Consistent with previous studies (Morris et al., 1996), a low frequency (<0.5%) shift to the rugose phenotype was found in several strains. While it is possible that nonpathogenic strains might have to be grown under different conditions to stimulate switching to the EPSon rugose phenotype, this would still nevertheless indicate that there is a difference between clinical and nonpathogenic strains. The laboratory of the present inventor found that a sixth pandemic (classical biotype) strain, NCTC 6585, switched at high frequency to the rugose phenotype (up to 48%). HFRP was defined as a >3% shift from the smooth to rugose phenotype (Ali et al., 2002). To confirm the rugose variant of NCTC 6585 expressed rEPS, transmission electron microscopy (TEM) was performed on ruthenium red stained thin sections. For TEM, 2 day old smooth and rugose colonies on LB agar were removed as 0.5-cm² blocks then fixed and stained in a solution of 2% glutaraldehyde, 0.075% ruthenium red, 50 mM lysine monohydrochloride in 0.1 M cacodylate buffer (pH 7.2) for 1 h at room temperature then 18 h at 4° C. Samples were washed twice in 0.1 M cacodylate buffer (pH 7.2), encased in 2% molten Noble agar and postfixed with 1% osmium tetroxide in 0.1 M cacodylate buffer (pH 7.2) overnight at 4° C.

Samples were then dehydrated in 30%, 50%, 70% and 90% EtOH for 10 min each and twice in 100% EtOH for 15 min each, followed by two treatments with propylene oxide 15 min each then infiltrated using a 1:1 solution of propylene oxide and epon for 2 h at room temperature then in 3:1 epon/propylene oxide overnight. Samples were then placed in pure epon for 1 h, embedded in epon and put in a 60° C. oven for 2 days then thin sectioned (50-80 nm thick). Sections were stained with uranyl acetate for 20 min then lead citrate for 20 min. Samples were examined under a JEOL 1200 EX II transmission microscope at 80 kV. TEM of rugose NCTC 6585 showed the presence of extracellular polysaccharide between cells and the absence of this material from smooth cells. It appears that all major epidemic clones of *V. cholerae* (classical, El Tor and O139) can shift to the rugose phenotype.

Production of rEPS is known to promote resistance of El Tor strains to a variety of environmental stresses such as chlorine, UV light, hydrogen peroxide, and complement-mediated bactericidal activity (Morris et al., 1996; Rice et al., 1993; Watnick et al., 1999 and Yildiz et al., 1999). In order to determine whether rugose cells of the $6^{th}$ pandemic classical biotype strain NCTC 6585 promoted resistance to environmental stresses, smooth and rugose variants were exposed to chlorine. Chlorine resistance was assayed (four independent experiments) by using a 1:50 dilution of an overnight culture of NCTC 6585 in 3 ml of fresh LB (Miller) broth. Cultures were then incubated statically at 37° C. for 3 h until CFU/ml ~$2 \times 10^8$ CFU/ml, the cells harvested by centrifugation and resuspended in phosphate buffered saline (PBS) (pH 7.2) containing 3 mg/L free chlorine (sodium hypochlorite, Sigma). Following 5 min exposure to 3 mg/L chlorine, cultures were serially diluted and plated on LB agar to determine the number of surviving cells. Consistent with El Tor strain 92A1552 (Yildiz et al., 1999), rugose NCTC 6585 cells were 10,000-fold more resistant to chlorine (5 min. exposure to 3 mg/L) than smooth cells. These findings are the first to report the rugose phenotype by classical biotype strains and shows that rEPS also promotes the survival of classical biotype strains.

Switching to EPSon and the Rugose Phenotype Promotes Biofilm Formation

As the rugose phenotype can promote biofilm formation in El Tor and O139 strains, the ability of smooth and rugose variants of N16961 (El Tor), NCTC6585 (classical) and Aldova (non-O1/non-O139) strains to form biofilms was tested using previously described methods (Watnick et al., 2001). Glass test tubes containing 500 µl LB broth were inoculated with a 1:100 dilution of overnight culture of each variant.

Figure 2:
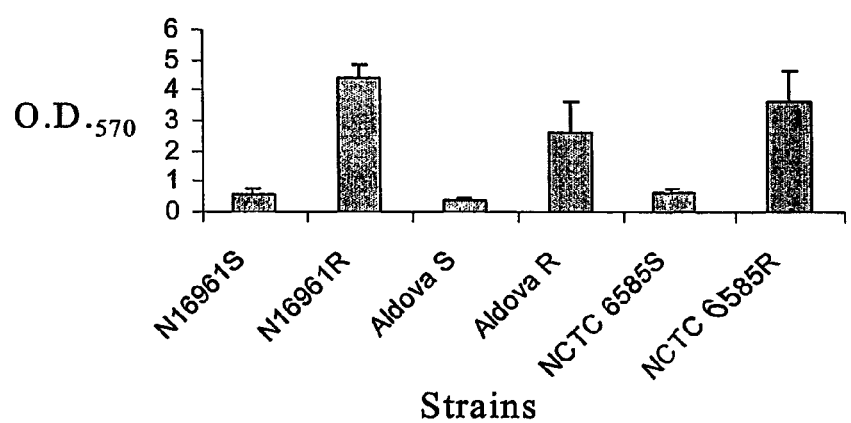
FIG. 2 is a graph showing biofilm formation by smooth and rugose colony variants of *V. cholerae*.

These cultures were then incubated statically at room temperature for 24 h. Culture supernatants were then discarded, tubes rinsed vigorously with distilled water to remove non-adherent cells, filled with 600 µl 0.1% crystal violet (Sigma), incubated for 30 min at room temperature and again rinsed with water. Quantitative biofilm formation was assayed by measuring optical density at 570 nm of the solution produced by extracting cell associated dye with 600 µl DMSO (Sigma). Consistent with other studies (Yildiz et al., 1999), the results show that rugose variants of all strains tested had significantly greater (~7-fold) biofilm forming ability than smooth cells (FIG. 2) and that EPS is essential for *V. cholerae* biofilm formation.

*V. cholerae* can Switch to the Rugose Phenotype (EPSon) in the Environment

The supposition that switching to EPSon and the rugose phenotype promotes the survival of *V. cholerae* in the environment is based on the premise that switching to EPSon occurs in the environment. However, there have been no reports detecting rugose *V. cholerae* from environmental (or clinical) sources. Unfortunately, there is no current enrichment method for isolating rugose strains from the environment and while TCBS is a selective and differential media for *V. cholerae*, the laboratory of the present inventor has found that TCBS inhibits (masks) the rugose phenotype (Ali et al., 2002).

To test whether smooth cells switch to the rugose phenotype in natural environmental water samples, natural lake water from Lake Kittamaqundi that is located on the edge of the City of Columbia, Howard County, Maryland was used. Lake Kittamaqundi is a 27-acre man-made lake approximately 1 mile long by $\frac{1}{8}^{th}$ mile wide and has a maximum depth of 7 feet. The Chesapeake Bay, which is approximately only several miles away, is known to be a natural reservoir of *V. cholerae*. Fresh water samples were collected from the lake between the warmer months of March-September, 2002. At collection, the lake water had pH 7.6 and $Na^+$ and $Cl^-$ concentrations of 6 mM and 2 mM, respectively. Lake water was autoclaved for 1 h prior to use. In this study, *V. cholerae* strain N16961 was grown in LB broth overnight at 37° C., centrifuged, washed twice with 0.85% NaCl, resuspended in PBS, appropriately diluted and inoculated into 100 ml lake water to a final concentration of $10^4$-$10^5$ cfu/ml confirmed by plate count. Microorganisms were incubated statically at room temperature in the dark and at appropriate time intervals aliquots were plated onto LB agar and plate counts and colony morphology were determined. The preliminary results after approx. 6 months sampling suggest that *V. cholerae* N16961 can persist under these conditions with only 1-log decrease in viability. Importantly, N16961 was able to switch from the smooth (EPSoff) to rugose (EPSon) phenotype at high frequency (up to 16%) under these conditions by day 50. An advantage of this study is that it closely mimics a true environmental scenario and the switching of a wildtype strain of N16961. While these studies could be extended, these results suggest that *V. cholerae* can shift to the rugose phenotype in natural environments.

Compositional Analysis of the rEPS in *V. cholerae*

The previous findings above from the laboratory of the present inventor were the first to report the rugose phenotype in a classical ($6^{th}$ pandemic) biotype strain of *V. cholerae*. In order to determine the structural composition of the rugose variant of classical biotype strain NCTC 6585 and to compare it to polysaccharides in other strains, a rugose colony of classical biotype strain NCTC 6585 was inoculated into APW#3 and incubated at 37° C. for 3 days under static conditions to promote EPS production and biofilm formation. To harvest the EPS, the cultures were filtered using a large (10 μm) pore size filter (VWR). The biofilm was washed once gently with PBS to remove planktonic cells, transferred to a fresh tube and 3 mm glass beads added to disrupt the biofilm. The sample was then centrifuged at 20,000 rpm (50,000×g) for 16 h at 4° C. to remove cell debris and other contaminants. The supernatant was passed though a Detoxi-Gel Affinitypak column (Polymixin B immobilized on agarose column) (Pierce) to remove any traces of LPS from the sample and DNase and RNase (final conc. 100 μg/ml) was added, then incubated at 37° C. for 4 h. Proteinase K (final conc. 100 μg/ml) was added and incubated at 37° C. overnight followed by 60° C. for 15 min. Following the addition of 3 volumes of 95% ethanol, the mixture was precipitated overnight at 4° C. then centrifuged at 12,000 rpm for 20 min. The precipitated EPS was washed twice, first with 80% ethanol and then with 95% ethanol. The EPS precipitate was resuspended in 0.5 ml MQ, incubated at −80° C. for 2 h, lyophilized for 4 h, then analyzed by combined gas chromatography/mass spectrometry (GC/MS) and performed by the Complex Carbohydrate Research Center in Atlanta, Ga.

The analysis in Table 2 below shows that the rugose EPS (rEPS) for $6^{th}$ pandemic strain NCTC 6585 differs markedly from the EPS of $7^{th}$ pandemic strain 92A1552 which has glucose as the predominant sugar (Yildiz et al., 1999) and strain TSI-4 which has mannose as the predominant sugar (Wai et al., 1998). The compositional analysis result also suggests that the extracellular carbohydrate described here is quite different from O1 LPS which typically contains large amounts of perosamine and quinovosamine (Raziuddin, 1980). In contrast to the results of El Tor strain 92A1552 in which 4-linked galactose and 4-linked glucose were the dominant linkages (Yildiz et al., 1999), the glycosyl linkage analysis using gas chromatography-mass spectrometry (GC-MS) performed on the classical biotype strain show that the predominant linkage is a 4-linked galactosyl residue and may represent the backbone of the saccharide.

TABLE 2

Glycosyl composition and linkage analysis of rEPS from strain NCTC 6585

| Sugar | Glycosyl Composition % | Glycosyl linkage Glycosyl residue[a] | % |
|---|---|---|---|
| Rhamnose | 8.92 | terminal linked-fucosyl residue | 9.8 |
| Fucose | 10.46 | terminal linked-glucosyl residue | 7.9 |
| Mannose | 4.68 | 3 linked-glucosyl residue | 8.8 |
| Galactose | 18.71 | 2 linked-glucosyl residue | 15.0 |
| Glucose | 9.29 | 4 linked-manosyl residue | 14.2 |
| GalNAc | 16.86 | 4 linked-galactosyl residue | 24.8 |
| GlcNAc | 27.65 | 2,3,4 linked-fucosyl residue | 7.7 |
|  |  | 2,3 linked-manosyl residue | 11.8 |

[a]All residues are in the pyranose (p) form.

Example 2

*Vibrio cholerae* can switch to a "rugose" phenotype characterized by an exopolysaccharide (EPS) matrix, wrinkled colony morphology, increased biofilm formation and increased survival under specific conditions. The vps gene cluster responsible for the biosynthesis of the rugose EPS (rEPS) is positively regulated by VpsR. Media (APW#3) promoting EPS production and the rugose phenotype was identified and epidemic strains were found to switch at higher frequency than nonpathogenic strains, suggesting this switch and extracellular polysaccharide is important in *cholera* epidemiology. In the experiments in this example, transposon mutagenesis on a smooth *V. cholerae* strain was used to identify mutants that were unable to shift to the rugose phenotype under inducing conditions to better understand the molecular basis of the switch. The present inventor identified vpsR, galE and vps previously associated with the rugose phenotype, and also identified genes not previously associated including rfbD and rfbE having roles in LPS synthesis and aroB and aroK with roles in aromatic amino acid synthesis. Additionally, a mutation in amiB encoding N-acetylmuramoyl-L-alanine amidase caused defects in the switch, motility and cell morphology. It was also found that a gene encoding a novel regulatory protein termed RocS (regulation of cell signaling) containing a GGDEF and EAL domain and that is associated with c-di-GMP levels is important for the rugose phenotype, EPS, biofilm formation and motility.

Materials and Methods
Mutagenesis and Screening for Genes with Roles in the Switch to the Rugose Phenotype The previous identification of culture conditions that promote the switch to the rugose phenotype at high frequency (HFRP) by the laboratory of the present inventor (Ali et al., 2002) was exploited in the development of an assay to identify genes involved in the molecular switch from the smooth to the rugose phenotype. In previous studies, the laboratory of the present inventor reported that incubation of cells in a medium called APW#3 resulted in a high frequency of *V. cholerae* smooth N16961 cells (up to ~80%) switching to the rugose phenotype (Ali et al., 2002). N16961 is a wildtype seventh pandemic (El Tor strain) isolated in Bangladesh (Levine et al., 1981). To identify the genes involved in the molecular switch from the smooth (EPSoff) to the rugose (EPSon) phenotype, mini-Tn5 km2 mutagenesis was used (de Lorenzo et al., 1990 and Herrero et al., 1990). Tn5 is contained on the R6K-based plasmid pUT/mini-Tn5 Kan (or pUTKm) that is derived from suicide vector pGP704 (Miller et al., 1988) and can only be maintained in donor strains (e.g., a λpir lysogen of *Escherichia coli*) that produce the R6K-specified λpir protein which is an essential replication protein for R6K and plasmids derived therefrom. It also carries the origin of transfer, orit, of plasmid RP4 which enables efficient conjugal transfer. Delivery of the donor plasmid pUTKm into recipient cells is mediated by the cognate transposase encoded on the plasmid at a site external to the transposon. An advantage of this mutagenesis system is the stability of the Tn5 insertion since the cognate transposase is not carried with the transposon during transposition. Thus, each mutant has only a single Tn5 insertion to screen.

*E. coli* S17 λpir (pUT/mini-Tn5 Km) was mated with smooth N16961 (EPSoff) cells and 14,500 mini-Tn5 mutants from 30 independent conjugations were obtained and were subsequently stored in wells of microtiter plates. A high throughput screen for HFRP mutants was performed in which the transposon mutants were inoculated into 200 μl APW#3 media in wells of microtiter plates, incubated for 48 h then replica plated onto LB agar and incubated for 24-48 h after which the colony morphology was visually examined. Using this approach, 43 mutants operationally defined as HFRP-negative that did not produce any rugose colonies were identified. It was further confirmed that these mutants were stable and defective in switching to the rugose phenotype under HFRP-inducing conditions by inoculating a colony into 3 ml APW#3 in glass test tubes and incubating statically for 48 h at 37° C. Sterile glass beads (4 mm diameter) were then added and the cultures vortexed to disrupt any aggregates of rugose cells. Appropriate dilutions of each culture were plated on LB agar and colonies were counted by standard plate count to determine the total CFU/ml and the frequency of rugose cells. The 43 mutants identified and tested by these screening methods did not produce any detectable rugose colonies under rugose-inducing (HFRP) conditions and were further studied.
Sequencing of Transposon Insertion Sites and Identification of Disrupted Genes To identify the transposon insertion site in these mutants, a non-laborious arbitrary primed PCR method was used followed by DNA sequencing similar to that described previously (Bahrani-Mougeot et al., 2002). Briefly, arbitrary PCR was performed in two steps: in the first reaction, chromosomal DNA of the mutant was used as a template for PCR using primers reading out from both sides of the transposon and two arbitrary primers. These primary reactions yielded numerous amplicons including some that were derived from the junction of the transposon insertions. The products of the first-round PCR were purified by Geneclean and amplified using a second pair of outward transposon primers external to the first pair and an arbitrary primer corresponding to the constant region of the original arbitrary primers. This secondary PCR reaction serves specifically to amplify products of the first PCR that include transposon junctions. Amplified fragment ranged between 100- to 800-bp. The products that gave the strongest bands were from agarose gels and sequenced using the same transposon and arbitrary primers used in the second-round PCR. Sequencing was performed using an automated DNA sequencer (model 373A, Applied Biosystems) using the Prism ready reaction dye deoxy termination kit (Applied Biosystems) according to the manufacturer's instructions.

Cloning of vpsR

The vpsR gene of N16961 was obtained on a 2.61-kb PCR fragment using PCR primers KAR486 (5'-CGGGATC-CCGCTAAGTCAGAGTTTTT ATCGC-3'; SEQ ID NO:3) and KAR487 (5'-TCCCCGCGGGTCGGTG-GTTTTGATCG TGT-3'; SEQ ID NO:4). The PCR fragment was digested with BamHI and SacII, respectively, and suitably cloned into the low copy vector pWSK29 (Wang et al., 1999), creating plasmid pDK104.

Motility Assay

Motility was determined in a swarm plate assay by measuring the swarm diameter of each zone after stabbing an equal amount of *V. cholerae* cells (grown in LB broth) into LB media containing 0.3% agar and incubation at 37° C. for 4 h.

Microscopic Analysis of amiB Mutant Strain

A single 18 h colony on a LB plate from the wildtype N16961 and amiB mutant strain DK630 was resuspended in 1 ml PBS and a 50 µl aliquot smeared onto a glass slide, heat fixed then stained with 0.1% crystal violet for 30 sec. The slide was then rinsed with $dH_2O$, dried and cell morphology observed using a Zeiss Axioskop epifluorescence microscope (Carl Zeiss, Inc. N.Y.). The images were acquired using an AxioCam Mrm camera (Carl Zeiss, Inc. N.Y.).

Results and Discussion

The laboratory of the present inventor has successfully sequenced and identified the transposon insertion site in 43 *V. cholerae* mutants that are unable to switch from the smooth to the rugose phenotype. A summary of a BLAST search against the published *V. cholerae* N16961 genome to identify the disrupted genes (Heidelberg et al., 2000) is shown in Table 3.

TABLE 3

Representative HFRP mutants of *V. cholerae* N16961

| Mutant[a] | Locus[b] | Predicted protein | Predicted function |
|---|---|---|---|
| DK568 (2) | VC0243 | RfbD | LPS biosynthesis, GDP-mannose 4,6 dehydratase |
| DK623 (1) | VC0244 | RfbE | LPS biosynthesis, perosamine synthase |
| DK578 (2) | VCA0744 | GalE | LPS biosynthesis, UDP-glucose 4-epimerase |
| DK589 (1) | VC0920 | Vps (EpsF) | EPS biosynthesis, glycosyl transferase |
| DK576 (2) | VC0921 | Vps (Wzx) | EPS, polysaccharide export, flippase |
| DK588 (7) | VC0922 | Vps | EPS, hypothetical protein |
| DK562 (13) | VC0665 | VpsR | EPS biosynthesis, $\sigma^{54}$ transcriptional activator |
| DK614 (10) | VC2628 | AroB | aromatic a.a. synthesis, 3-dehydroquinate synthase |
| DK625 (1) | VC2629 | AroK | aromatic a.a. synthesis, shikimate kinase |
| DK630 (1) | VC0344 | AmiB | N-acetylmuramoyl-L-alanine amidase |
| DK567 (3) | VC0653 | RocS | regulatory, contains GGDEF and EAL domains |

[a]Numbers in brackets indicate number of mini-Tn5 mutants having insertions in same locus.
[b]Loci and predicted proteins derived from the *V. cholerae* N16961 TIGR sequencing project.

Previous transposon mutagenesis studies have identified gene mutations that result in stable rugose-to-smooth mutants (Watnick et al., 1999; Yildiz et al., 1999; and Ali et al., 2000). In contrast, taking advantage of the conditions developed by the laboratory of the present inventor that promote switching to rugose phenotype, transposon mutagenesis on a smooth strain of N16961 was performed and stable mutants that were unable to switch to the rugose phenotype under rugose-inducing conditions were screened. While the findings revealed mutants with defects in genes previously identified with roles in the rugose phenotype such as several biosynthesis (vps operon) and regulatory genes (vpsR) and LPS genes (galE), this screen also identified mutants sustaining insertions in previously unidentified genes. These newly identified mutants could be clustered into several functional groups coding for LPS (rfbD and rfbE) in which the genes might have roles in catalyzing the addition of certain sugar linkages and whereby impairment in the LPS structure might also be linked to the shutdown of the rugose (EPSon) phenotype; genes involved in aromatic amino acid synthesis (aroB and aroK) whereby aromatic amino acid synthesis genes might be directly or indirectly associated with the rugose phenotype; a gene involved in cell wall hydrolysis (amiB) and a novel locus, VC0653, designated "pdeA-like" in the N16961 genomic database, which the present inventor has now termed RocS (for regulation of cell signaling; SEQ ID NO:1) encoding a putative protein (SEQ ID NO:2) containing GGDEF and EAL domains. While the exact function of GGDEF and EAL domains is not well understood but are thought to have some role in signaling, proteins containing these domains are widespread in prokaryote species and appear to play a key function in the regulation and biology of many species.

VpsR has an Essential Role in Switching to the Rugose Phenotype

The importance in regulating vps biosynthetic genes in *V. cholerae* led the present inventor to further study several vpsR transposon mutants, designated DK562 and DK581. VpsR, encoded by the locus VC0665 is a predicted 444 amino acid protein with high similarity to the family of $\sigma 54$ response regulators such as NtrC, AlgB, and HydG (Yildiz et al., 2001 and Ali et al., 2000). The laboratory of the present inventor found that supplying vpsR on plasmid pDK104, can restore switching to the rugose phenotype in both these vpsR mutants. These findings confirm that the defect in switching to the rugose phenotype in these mutants is due to the mutation in vpsR. Since VpsR is predicted to be a transcriptional activator, the present inventor speculated whether it controlled motility in *V. cholerae*. The motility tests performed on the VpsR mutants (DK562 and DK581) showed that the mutants are consistently ~50% reduced in its motility compared to the parent N16961 (data not shown). Since *V. cholerae* cells are typically motile and motility is important for virulence (Yancey et al., 1978 and Richardson, 1991), it is tempting to speculate that VpsR might also have a role in virulence of *V. cholerae*. Although VpsR is important in regulating EPS (vps) biosynthesis genes and potentially other phenotypes, the conditions promoting VpsR expression and its mechanism of regulating vps genes is not well understood.

The AmiB Amidase has a Role in the Switch to the Rugose Phenotype

The AmiB (N-acetylmuramoyl-L-alanine amidase) protein is encoded by the amiB gene (VC0344). Since it was previously found that rugose strains of *V. cholerae* are affected in motility (Ali et al., 2002), amiB mutants were tested to see if their motility was affected. Motility assays showed that the AmiB mutant (strain DK630) was consistently >50% reduced in its motility (10 mm zone) compared to its parent N16961 (26 mm zone) (FIG. 3). These results suggest that AmiB affects motility and the rugose phenotype in *V. cholerae*.

The bacterial cell wall is typically composed of a heteropolymer known as murein or peptidoglycan. Many Gram-negative bacteria degrade up to 50% of their murein per generation and recycle it to form new murein (Goodell, 1985; Park, 1993). N-acetylmuramoyl-L-alanine amidases are often associated with autolysis or microbial cell wall hydrolysis. Surprisingly, enzymes in Gram-negative bacteria that cleave the septum such as AmiB have only recently been studied in a few species, and in *E. coli*, AmiB mutants are found growing as long chains of unseparated cells (Heidrich et al., 2001 and Holtje et al., 2001). In *Azotobacter vinelandii*, an N-acetylmuramoyl-L-alanine amidase is linked to alginate production by the ability of *A. vinelandii* cells to recycle their cell wall (Nunez et al., 2000).

A BLAST search shows that the *V. cholerae* AmiB sequence has high similarity to N-acetylmuramoyl-L-alanine amidases found in a wide variety of species including *Pseudomonas aeruginosa* ($7e^{-78}$), *Salmonella enterica* Typhi ($7e^{-69}$), *E. coli* O157:H7 ($6e^{-57}$) and Yersinia pestis ($6e^{-50}$). AmiB in *V. cholerae* strain N16961 is predicted to be a 59-kDa protein that is unusually rich in serine (9.5%), proline (6%) and threonine (6%). Such a composition is common in protein domains associated with the cell wall in Gram-positive bacteria (Fischetti et al., 1991) and is similar to a putative peptidoglycan hydrolase of *Lactococcus lactis* (acmB) (Huard et al., 2003). In *V. cholerae*, like in *E. coli* and *Y. pestis*, amiB is located immediately upstream of mutL which has a role in DNA mismatch-repair (Tsui et al., 2003 and Parkhill et al., 2001). A computer analysis using PSORT shows that *V. cholerae* AmiB is predicted to have a cleavable N-terminal signal sequence and an analysis using TMpred strongly predicts that AmiB has two transmembrane domains (score 2363), one at the N-terminal end (a.a. 10-29) which could also represent an N-terminal signal anchor sequence and another transmembrane domain at the C-terminal end (a.a. 446-465). One would expect TMpred to predict a transmembrane region at the N-terminal end if a sec-dependent signal sequence was also predicted. The *V. cholerae* AmiB is also predicted to contain a LysM (lysin motif) domain at its C-terminal end and this has been found in enzymes involved in cell wall degradation (Bateman et al., 2000). Interestingly, the *V. cholerae* AmiB contains a Arg-Gly-Asp (RGD) motif that is often associated with a surface binding domain for various mammalian adhesion proteins.

Since AmiB has been associated with septation in other species such as *E. coli* (Heidrich et al., 2001 and 2002), it was determined whether the *V. cholerae* AmiB mutant was affected in its cellular morphology as well as the rugose phenotype. Examination of the cells showed an obvious difference between the AmiB mutant (FIG. 4B) and the wildtype strain (FIG. 4A) in the morphology and arrangement of the cells. Many cells of the AmiB mutant were altered in shape and some were dramatically increased in cell size (length and width). The AmiB mutant appeared to have a higher percentage of cells in chains. This finding suggests that cell division or septation might be affected. No difference in growth rate between wildtype and the AmiB mutant DK630 was found (data not shown), suggesting that the difference in cell structure is not due to differences in growth rate. While the findings of cells grown on LB plates bred true following subculture, no obvious dramatic differences between the strains when grown in LB broth were found (data not shown). Although further studies are required to analyze the cellular structure and morphology of the AmiB mutant in more detail, such as using electron microscopy, the results of the studies presented in this example suggest there is a link between cell division, structure or septation and the rugose phenotype of *V. cholerae*. These findings provide evidence for a new function for a prokaryotic amidase, namely its importance in the switch to the rugose phenotype and biofilm formation.

*V. cholerae* RocS: a Conserved Regulatory Protein with a GGDEF and EAL Domain Regulates the Rugose Phenotype Another class of mutants that the laboratory of the present inventor was particularly interested in were mutants with defects in the locus VC0653 encoding a putative protein termed RocS (formerly "PdeA-like" protein in the database) containing a GGDEF and EAL domain. It is important to note that three independent mutants containing mutations in rocS from three independent conjugations were isolated. This result suggests that *V. cholerae* RocS has an important role in rEPS production, the rugose phenotype, in biofilm formation and possibly other phenotypes. The defect in the rugose phenotype in this mutant was not explained by differences in growth rate between the wildtype N16961 and RocS (DK567) cells (data not shown). The finding that *V. cholerae* RocS mutants appear to be defective in the switch to the rugose phenotype prompted testing their motility as described above. Motility assays showed that the RocS mutant (DK567) was consistently >50% reduced in its motility (12 mm zone) compared to its parent N16961 (26 mm zone) suggesting that this locus also affects motility in *V. cholerae* (FIG. 3). Based on these results, the present inventor proposes. that *V. cholerae* RocS (and c-di-GMP) regulates several phenotypes, including those with roles in virulence, biofilms and the persistence of species.

Interestingly, GGDEF domains have been shown in proteins known to be involved in the regulation of cellulose (β-1,4-glucan) synthesis (Ausmees et al., 2001). Cellulose production in *Acetobacter xylinum*, *Rhizobium leguminosarum bv. trifolii* and *Agrobacterium tumefaciens* is modulated by the opposing effects of two enzymes, diguanylate cyclase (Dgc) and c-di-GMP diesterase (PdeA), each controlling the level of the novel signaling molecule c-di-GMP in the cell (Amikam et al., 1989 and Ross et al., 1990 and 1991). Diguanylate cyclase acts as a positive regulator by catalyzing the formation of c-di-GMP that specifically activates cellulose production while the phosphodiesterase cleaves c-di-GMP and negatively regulates cellulose. The c-di-GMP molecule is predicted to be a reversible, allosteric activator (effector) of cellulose biosynthesis (Ross et al., 1991). Furthermore, genetic complementation studies using genes from different species encoding proteins with GGDEF domains as the only element in common suggest that the GGDEF domain has a role in diguanlylate cyclase activity and is important in modulating the level of c-di-GMP (Ausmees et al., 2001). The laboratory of the present inventor found that the *V. cholerae* RocS protein plays a key role in the switch to the rugose phenotype that is associated with the production of an EPS-like material and increased biofilm formation.

A BLAST search of the *V. cholerae* RocS shows that it is highly conserved and has significant homologues to putative proteins found in a wide variety of other species including *P. aeruginosa* (PA0575; 42% id; $5e^{-92}$), *Bacillus anthracis* (BA5593; 37% id; $6e^{-90}$), *Ralstonia solanacearum* (RSc0588; 36% id; $4e^{-88}$) and *A. xylinum* (c-di-GMP diguanylate cyclase Dgc; 40%, $9e^{-82}$). Although dgc and pdeA genes share some homology and have similar domain architecture, the finding here that the rocS mutant is unable to produce an EPS-like material is more consistent with a diguanylate cyclase (dgc) mutant that is unable to produce cellulose. *V. cholerae* RocS has slightly higher similarity to *A. xylinum* Dgc than PdeA (data not shown). Recent reports have identified "RocS" homologues in *P. aeruginosa* that appear essential for biofilm formation (Connolly et al., 2003) and in *V. parahaemolyticus* that regulate capsular polysaccharide production (Güvener et al., 2003). Additionally, the autoaggregation phenotype (which is typical of the rugose phenotype) in the plague bacterium *Y. pestis* requires the GGDEF-containing protein HmsT (Jones et al., 1999). Although homologous regulatory (GGDEF-containing) proteins have been found in several species and have been associated with wrinkled colonies, EPS production and biofilm formation, their role in regulating these processes has not been well studied, in part due to the lack of available reagents. There is growing evidence suggesting that GGDEF-containing proteins possess nucleotide cyclase activity (Ausmees et al., 2001; Ross et al., 1987; Pei et al., 2001 and Tal et al., 1998) and are widespread in bacteria (Croft et al., 2000 and Galperin et al., 2001). The potential widespread occurrence of this protein homologue and c-di-GMP in prokaryotes suggests common regulatory systems and that they might have an important function in regulating phenotypes including EPS production, the rugose phenotype and biofilm formation in *V. cholerae* and phenotypes in other species.

A rugose-like phenotype has been reported in several species including *S. enterica Enteritidis* (Petter, 1993), *S. enterica Typhimurium* (Anriany et al., 2001), *V. parahaemolyticus* (Güvener et al., 2003), *P. aeruginosa* (D'Argenio et al., 2002) and *Enterobacter sakazakii* (Farmer et al., 1980). It is now becoming increasingly recognized that the rugose phenotype might have an important role in *V. cholerae* and in several other species suggesting that these "variants" might represent the "tip of an iceberg". Data is accumulating suggesting that rugose variants are filling a specific role in biofilm formation, particular niches or in particular environments. In the case of *V. cholerae*, rEPS production, the rugose phenotype and HFRP may provide some evolutionary or adaptive advantage to that subpopulation of cells in a particular environment.

In the studies presented in this example, the identification by the laboratory of the present inventor of conditions that promote the high frequency switch from the smooth to the rugose phenotype of *V. cholerae* was exploited to identify and study the genes involved in the molecular switch between the smooth and rugose phenotypes. It appears that some *V. cholerae* strains have evolved an efficient mechanism for a high frequency shift to the rugose phenotype that is associated with EPS production, increased biofilm formation and increased cell survival under specific conditions. The switching ability that can lead to increased biofilm formation might provide an adaptive advantage in particular environments where strains compete for the same ecological niche and where slight variations in phenotype that promote resistance, increased colonization or cell aggregates are important for adaptation and survival.

Example 3

*Staphylococcus aureus* is an important pathogen of humans and animals and its antibiotic resistance is a public health concern. Biofilm formation is essential in pathogenesis, and the ability to form biofilms and resist traditional antibiotic treatments often results in difficult-to-treat and persistent infections. As such, novel antimicrobial approaches are of great interest to the scientific, medical and agricultural community. The present inventor proposed in Example 1 that modulating levels of the cyclic dinucleotide signalling molecule, c-di-GMP (3', 5'-cyclic diguanylic acid), has application in regulating phenotypes of prokaryotes. In the experiments described below in this example, extracellular c-di-GMP shows activity against human clinical and bovine intramammary mastitis isolates of *S. aureus*, including methicillin-resistant (MRSA) strains. The present example shows that chemically synthesized c-di-GMP is soluble and stable in water physiological saline and stable following boiling and exposure to acid and alkali. Treatment of *S. aureus* with extracellular c-di-GMP inhibited cell-to-cell (intercellular) adhesive interactions in liquid media and reduced (>50%) cell-to-surface interactions and biofilm formation in human and bovine isolates compared to untreated controls. c-di-GMP inhibited the adherence of *S. aureus* to human epithelial HeLa cells with c-di-GMP showing no obvious toxicity on HeLa cells and was non-lethal in mice. The guanosine nucleotide analog cGMP had a lesser effect on biofilms while 5'-GMP had no effect. The data here suggests that *S. aureus* might sense and respond to extracellular c-di-GMP signals. Cyclic dinucleotides, such as c-di-GMP, when used either alone or in combination with other antimicrobial agents, represent a novel and attractive approach in inhibiting and controlling biofilms and in the control and treatment of infection.

Materials and Methods c-di-GMP, CGMP and 5'-GMP nucleotides used. c-di-GMP used in the studies in this example was biochemically synthesized in pure form using a recently described novel synthesis method that produces a pure and high yielding preparation of c-di-GMP diammonium salt (FIG. 5A) (Hayakawa et al., 2003). Before use, the purity and stability of lyophilized c-di-GMP was determined by first resuspending the molecule in 0.9% NaCl creating a 2 mM solution then confirmed by HPLC analysis and ESI-TOF MS spectrometry. The cGMP (guanosine 3', 5'-cyclic monophosphate, Sigma #G7504) and 5'-GMP (guanosine 5'-monophosphate, TCI, Tokyo Kasei Kogyo Co.) nucleotides were also used. Unless otherwise stated, a 4 mM stock solution of each nucleotide in 0.9% NaCl was prepared and stored at 4° C. until needed.

Bacterial strains and growth media used. Human clinical isolates of *S. aureus* were used in this study and stored at −70° C. in 50% glycerol. *S. aureus* strain DK825 was isolated in 2003 from the blood culture of a patient at the Veterans Affairs Medical Center (approximately 200 acute care beds) in Baltimore, Md. DK825 was isolated by the diagnostic microbiology laboratory at the VAMC and confirmed as methicillin-resistant *S. aureus* (MRSA) using standard plating techniques, latex agglutination using a BactiStaph Latex 150 test kit (Remel) for the detection of coagulase and by antibiotic susceptibility tests (Sensititre plates, Microbiology Systems). *S. aureus* strain 15981 is a highly adherent hyperbiofilm human clinical strain that was isolated in 1999 from an otitis patient by the clinical laboratory at the Universitaria de Navarra, Spain (Iñigo Lasa, personal communication) (Valle et al., 2003). *S. aureus* 15981 is a natural agr mutant and is susceptible to MET, AMX, CLI, ERY, DOX, FOF, VAN, CIP and resistant to GEN. The wildtype bovine subclinical mastitis strains used in this study were V329 (hyperbiofilm strain) (Cucarella et al., 2001), V299 (bap-negative icaADBC-positive) (Cucarella et al., 2004) and V315 (bap-negative and icaADBC-negative) (Cucarella et al., 2004). *S. aureus* strain M556 (isogenic transposon insertional bap-mutant of V329) was also used (Cucarella et al., 2001). Unless otherwise noted, *S. aureus* strains were grown at 37° C. on sheep blood agar plates or in tryptic soy broth (TSB, Difco) supplemented with 0.25% glucose.

c-di-GMP stability tests. Although the term c-di-GMP is used here, c-di-GMP diammonium salt (and not the free diphosphoric acid) was used for these stability tests. (i) In boiling water: A 2 mM solution of c-di-GMP in water was prepared by dissolving 2.42 mg (3.3 μmol) of c-di-GMP in 1.65 mL of ion-exchanged/ion-free water (prepared by passing distilled water through ion-exchange resins). This solution was heated at 100° C. for 10 min and then concentrated under reduced pressure. The resulting residual was subjected to the HPLC analysis under conditions shown below. (ii) In pH 3 solution: From the 2 mM c-di-GMP aqueous solution described above, 500 μl (containing 1 μM of c-di-GMP) was dissolved in 20 mL of 1 mM HCl to produce a solution with pH 3 (confirmed by pH meter). The resulting solution was stirred at room temperature for 1 h and then neutralized by the addition of 200 mL of a 0.1 mM NaOH. Water was evaporated under reduced pressure and the resulting residue was subjected to HPLC analysis. (iii) In pH 10 solution: From the 2 mM c-di-GMP aqueous solution described above, 500 μl (containing 1 μM of c-di-GMP) was dissolved in 200 mL of a 0.1 mM NaOH aqueous solution to produce a solution with pH 10 (confirmed by pH meter). The resulting solution was stirred at room temperature for 1 h. The reaction was quenched by addition of 20 mL of a 1 mM HCl. Concentration of the resulting neutral solution under reduced pressure gave a residual material that was subjected to the HPLC analysis. The HPLC analysis was performed on a Waters 2695 Separation Module with a Waters 2996 Photodiode Array Detector under the following conditions. Column: Nacalai Tesque COSMOSIL 5C18-AR-II column (4.6 mm (diameter)×250 mm (length)); detection: 254 nm of UV ray; temperature: 40° C.; eluent: A=0.9% NaCl (aq), B=a 20:80 mixture of water:acetonitrile; flow rate:1 mL/min; 0-10 min: A 100%; 10-60 min: linear gradient from A100%/B 0% to A 40% to B 60%.

Antibiotic susceptibility testing. Susceptibility tests were performed in Sensititre microtitre plates according to the manufacturer's instructions (Microbiology Systems).

Effect on growth rate of *S. aureus*. *S. aureus* DK825 was subcultured from glycerol stocks onto a blood agar plate and incubated at 37° C. for 18 h. A single colony was then inoculated into 5 ml TSB broth (supplemented with 0.25% glucose) and incubated at 37° C. for 24 h with shaking at 250 rpm. From a $10^{-3}$ dilution of the overnight culture a 100 μl aliquot was inoculated into tubes containing 5 ml TSB broth resulting in an initial cell count of $10^{-5}$ cfu/ml (confirmed by plating). For "treated" samples, an appropriate aliquot of c-di-GMP was added to give 200 μM c-di-GMP (final concentration). As a negative "untreated" control, tubes containing TSB and a similar volume of 0.9% NaCl were included in the studies. At time zero, 50 μl from each sample was plated on blood agar plates to determine the initial cfu/ml. The tubes were then incubated at 37° C. for 8 h under shaking conditions with aliquots being plated from all tubes every 30 min.

Tube agglutination assay and light microscopy. Colonies from a 18 h blood agar plate were inoculated into 1 ml PBS to make a 0.5 McFarland standard containing ~$5 \times 10^8$ cfu/ml (confirmed by plate count). A 5 μl aliquot from the 0.5 McFarland standard was then inoculated into 5 ml polystyrene tubes containing 1 ml TSB representing ~105 cfu/ml (confirmed by plate count). These tubes were inoculated either with 50 μl c-di-GMP to give a 200 μM c-di-GMP final concentration representing a "treated" sample or inoculated with 50 μl 0.9% NaCl as a control and representing an "untreated" control. Cultures were incubated at 37° C. for 24 h statically. Following incubation, these cultures were examined macroscopically and microscopically (Zeiss Axioskop) for the presence or absence of visible cell-to-cell clumping.

Effect of c-di-GMP on *S. aureus* biofilm formation. *S. aureus* strains were subcultured from glycerol stocks onto blood agar plates and incubated at 37° C. for 18 h. A single colony was inoculated into 5 ml TSB broth with a sterilized loop and incubated at 37° C. for 18 h with shaking at 250 rpm and until the O.D.$_{660}$ reached 3.0 as measured spectrophotometrically using a spectrophotometer (SpectraMAX 250, Molecular Devices). Following incubation, the culture was diluted 1:250 with fresh TSB and a 200 μl of the diluted culture was transferred into wells of a flat-bottom polystyrene microtitre plate (Evergreen Scientific). To test the effect of c-di-GMP treatment on biofilm formation, a series of "treated" samples containing 10-fold dilutions of c-di-GMP were set up in TSB which contained the following final concentrations of c-di-GMP (0-, 2-, 20- and 200 μM). In these biofilm experiments, similar volumes of 0.9% NaCl was added to a set of different wells representing the "untreated" control samples. The microtitre plates were then incubated statically at 37° C. for 24 h or 48 h. Following incubation, the supernatant was carefully discarded and the wells washed twice with 260 μl PBS. The plate was then kept for drying on a paper towel for 30 min after which 260 μl 0.1% crystal violet was added to each well and the plates incubated at room temperature for 30 min. The crystal violet was discarded and plate washed gently with water, the wells allowed to dry for 30 min then 260 μl DMSO was added to each well and gently agitated for 1 h and the O.D.$_{570}$ measured by using a spectrophotometer (SpectraMAX 250, Molecular Devices). The results of these biofilm assays were based on data obtained from at least three independent colonies tested in duplicate.

Effect of c-di-GMP on *S. aureus* pre-formed biofilms. *S. aureus* DK825 was subcultured from glycerol stocks onto blood agar plate and incubated at 37° C. statically. A single colony was inoculated into 5 ml TSB broth (containing 0.25% glucose) and incubated at 37° C. overnight with shaking at 250 rpm until the culture reached OD$_{660}$~3.0. Following incubation the culture was diluted to 1:250 with fresh TSB broth and a 200 μl of the diluted culture was transferred into each well of microtitre plate and the plate containing wells with *S. aureus* cultures was incubated statically at 37° C. for 24 h. After 24 h, an appropriate volume of c-di-GMP was added to give a final concentration of 200 μM and represented the "treated" sample. As an "untreated" control, an identical volume of 0.9% NaCl was added to independent wells. The plates were then incubated statically at 37° C. for an additional 24 h. Following incubation the culture was discarded and microtitre plate was washed twice with 1X PBS. An equal volume (260 μl) of 1X PBS was added to each well for washing. The plates were then kept for drying on paper towel ~30 min. A 260 μl of 0.1% crystal violet was added to each well to stain the cells in the biofilm and the plates were incubated at room temperature for 30 min. Crystal violet was discarded and plate was washed with tap water gently and kept on a paper towel to dry for 30 min. A 260 µl DMSO was added to each well and gently rocked for 1 h. To quantitatively assay the amount of biofilm, the $OD_{570}$ was measured by a spectrophotometer (SpectraMAX 250, Molecular Devices). The results were based on at least three independent colonies tested in duplicate.

Epithelial cell assay. HeLa cells (ATCC CCL2) were grown to confluence in complete medium (10% FBS from Sigma, DMEM/F12 with glutamine from Invitrogen and 50 µg/ml gentamicin) and were trypsinized with 0.1% trypsin-EDTA. Approximately $1 \times 10^5$ HeLa cells were seeded in each well of a chamber slide and then the HeLa cells were incubated at 37° C. in 5% $CO_2$ for at least 18 h until 85% confluent. Prior to infection, the HeLa cells were washed twice with warm PBS and then 500 µl warm FMEM/F12 was added to each well. For the bacterial adherence assay, an overnight culture of S. aureus strain DK825 was grown overnight in 5 ml LB broth at 37° C. with shaking at 250 rpm. Following incubation, 1 ml of the overnight culture was pelleted, washed twice with PBS and resuspended in 1 ml of PBS. The HeLa cells in the wells were washed twice with 500 µl of HBSS and aliquots of DMEM with the desired final concentration of c-di-GMP (0-, 2-, 20- and 200 µM) were prepared. DMEM (500 µl) containing the respective concentrations of c-di-GMP was inoculated into the wells containing HeLa cells followed by the addition of 10 µl ($\sim 10^7$ cells) S. aureus (MOI HeLa:bacteria~1:100). The epithelial cell assay was incubated in $CO_2$ for 45 min. Following incubation the cells were washed twice with 500 µl PBS and fixed with 2% formalin for 20 min. The cells were again washed twice with PBS and stained with Giemsa stain for 10 seconds, washed three times with PBS, then the cells covered with 40 µl of 90% glycerol in water and a cover slip was placed. The slides were observed under a light microscope (Zeiss Axioskop) at 630×mag. The level of bacterial adherence to 100 individual HeLa cells was calculated for each duplicate treatment and the average determined.

Safety and toxicity assays. For HeLa cell toxicity studies, various concentrations (0-, 25-, 50-, 100-, 200- and 400 µM) of c-di-GMP were tested in separate wells of chamber slides containing HeLa cells prepared as described above in complete media (in the absence of bacteria). HeLa cell morphology was examined microscopically after 12-, 24- and 48 h incubation. The potential lethality of c-di-GMP administered to mice was also examined. In these studies, adult female CD-1 mice and 5 day old infant mice were inoculated orally with 50 µL of 200 µM c-di-GMP and examined 24 h after c-di-GMP treatment.

Results and Discussion

The ability of S. aureus to form biofilms on various surfaces such as medical devices and tissues is an important and necessary first step in the pathogenesis of disease. The overall prevalence of S. aureus in the community and in hospitals, its ability to form biofilms, and the fact that S. aureus is frequently resistant to multiple antibiotics makes S. aureus a major public health problem. As such, novel intervention and antimicrobial methods that reduce biofilm formation in humans and animals may result in a corresponding increase in antibiotic susceptibility and more effective prevention and treatment strategies. This study shows that extracellular c-di-GMP inhibits cell-to-cell interactions and biofilm formation in human and animals isolates of S. aureus.

Identification of GGDEF domains in S. aureus suggests a link to c-di-GMP. c-di-GMP is associated with proteins containing GGDEF amino acid domains. The GGDEF domains are ~180 amino acid protein fragments that have an adenylate cyclase-like fold and work as a cyclic diguanylate synthetase. These domains have a conserved GG(D/E)EF motif (SEQ ID NO:5) but also many other conserved residues (Galperin, 2001 and 2004). GGDEF proteins are increasingly being found to be important in the regulation of bacterial exopolysaccharide, biofilm formation, colonization and adherence (Bomchil et al., 2003; D'Argenio et al., 2002; Jones et al., 1999 and Romling et al., 2000). These types of protein are widespread in bacteria suggesting that a broad range of species can potentially be targeted and phenotypes regulated by modulating c-di-GMP levels and numerous species have a large number of proteins with GGDEF domains (Galperin, 2001 and 2004). Interestingly, a search of the COG database shows that S. aureus has only one protein (SA0701, COG2199) with a C-terminal GGDEF domain and another protein (SA0013, COG3887) with a modified GGDEF domain (Tatusov et al., 2001). According to a Pfam analysis (pfam.wustl.edu), the N-terminal fragment of SA0701 is predicted to be an integral membrane sensor domain of the 5TM-5TMR_LYT type (5 predicted transmembrane segments, Pfam entry PF07694) and therefore is predicted to be a membrane receptor with a diguanylate cyclase output domain. Unfortunately, the role of these putative signal transduction proteins in S. aureus and whether they are potentially linked to c-di-GMP, whether c-di-GMP is made by S. aureus and whether the regulatory effects of c-di-GMP are similar in all species is not yet known.

Stability of c-di-GMP. The stability of c-di-GMP under various physical conditions and treatments is not well understood. However, if c-di-GMP is to be used as part of an antimicrobial strategy or therapeutic agent, its stability needs to be better studied. The laboratory of the present inventor determined the stability of c-di-GMP after several storage conditions and following various exposures including heat, acid (pH 3) and alkali (pH 10) treatment.

HPLC analysis of a neat (from lyophilized powder) form of c-di-GMP that was resuspended in ion-free distilled water (prepared by passing distilled water through an ion-exchange resin column) immediately before HPLC analysis to produce a 2 mM stock indicated that storage of a neat form of c-di-GMP for several days at −78° C. formed aggregate molecules whose structure is unknown at present but is being determined (data not shown). Furthermore, storage of a 2 mM stock solution having water as the diluent at ambient temperature (10-20° C.) for several days resulted in the formation of an aggregated product. Interestingly, however, adjustment of the solution to a concentration of 0.9% NaCl was found to revert the aggregated molecules back to the monomeric form as determined by HPLC and ESI-TOF MS spectrometry (data not shown). In phosphate buffer solution, c-di-GMP was stable in a 100 mM phosphate buffer for at least one month at −78° C., 4° C., and 25° C. and did not undergo any structural changes (data not shown). In a 0.9% NaCl solution, HPLC analysis showed that c-di-GMP was very stable as the monomeric structure following storage at either −78° C., 40° C., and 25° C. for at least three months (FIG. 5B). c-di-GMP was also found to be stable in a 100 mM ammonium acetate buffer for at least one month at −78° C., 4° C., and 25° C. and did not undergo any structural changes. These results suggest that stock solutions of c-di-GMP should be prepared in 0.9% NaCl such that c-di-GMP will be stable and remain as a monomeric form for at least several months.

Consistent with a previous study by Ross et al. (Ross et al., 1991) in G. xylinum examining the role of c-di-GMP in activating cellulose production, HPLC analysis in this study demonstrated that chemically synthesized c-di-GMP is stable following 10 min exposure at 100° C. While Ross found that the "activator" (measured by cellulose activating activity) is labile after treatment in relatively strong alkali (0.2 N NaOH, ~pH 13.5, 37° C. for 24 h), HPLC analysis conducted in this study suggests that c-di-GMP is stable following treatment in mild alkali (0.0001 N NaOH, pH 10, 20-25° C. for 1 h). Consistent with the findings in the previous study by Ross et al. (Ross et al., 1991), the data from the laboratory of the present inventor showed that chemically synthesized c-di-GMP is stable following acid treatment (0.001 N HCl, pH 3, 20-25° C. for 1 h). Based on these studies, c-di-GMP is a stable and soluble low molecular weight molecule.

Antibiotic susceptibility of *S. aureus* strain DK825. To further characterize *S. aureus* DK825, antibiotic susceptibility tests were performed against commonly used antibiotics. Antibiotic susceptibility tests for DK825 produced the following MIC profiles (μg/ml): Penicillin, PEN>8; Ampicillin, AMP 4; Oxacillin, OXA>2; Tetracycline, TET>32; Rifampin, RIF>2; Clarithromycin, CLR>4; Levofloxacin, LVX 2; Ciprofloxacin, CIP>2; Moxifloxacin, MXF 2; Clindamycin, CLI>2; Erythromycin, ERY>4; Vancomycin, VAN<0.5. These findings further showed that *S. aureus* DK825 is resistant to multiple commonly used antibiotics but is sensitive to vancomycin.

c-di-GMP treatment prevents *S. aureus* cell-to-cell interactions. Initial experiments on the effect of c-di-GMP on *S. aureus* examined whether c-di-GMP had any effect on the growth rate of *S. aureus*. Hourly examination of the growth rate for up to 8 h showed that 200 μM c-di-GMP had no obvious effect on growth rate. The laboratory of the present inventor then tested whether c-di-GMP treatment affected the macroscopic growth and appearance of *S. aureus* cells after 24 h static incubation in liquid culture. Following incubation, the treated and untreated cultures were visually examined for visible cell-cell clumping and aggregation. The results with *S. aureus* DK825 showed that the 200 μM c-di-GMP treated culture exhibited no obvious visible cell aggregation or pellet at the bottom of the tube (FIG. 6A) while the untreated culture showed obvious cell aggregation and a pellet (FIG. 6B). Plating of c-di-GMP-treated and untreated cultures showed no difference in final cell count ($6 \times 10^8$ CFU/ml) between the cultures further suggesting that the inhibition of cell-to-cell interactions is not due to major differences in growth rate or final cell numbers. Similar effects on cell aggregation at the bottom of the tube in response to c-di-GMP were observed with several independent wildtype *S. aureus* bovine mastitis strains (V329, V299, V315) (data not shown). A recent study by Cucarella et al. (Cucarella et al., 2001) reported that accumulation of cell aggregates at the bottom of the tube was macroscopically only observed for wildtype V329 and not with the isogenic bap mutant M556. While much less visible clumping in strain M556 was observed, the results here clearly suggested that c-di-GMP treatment inhibits cell aggregation of M556 cell at the bottom of the tube compared to untreated cultures (FIGS. 6E and 6F). It is also important to note that strain M556, while being a bap mutant is ica-positive (Cucarella et al., 2001). Two possibilities that might explain the findings in these two studies are that the results of Cucarella et al. were based on shaking cultures or that TSB obtained from different sources might influence cell growth and cell interactions. Inhibition of cell aggregation was consistent and was observed following similar c-di-GMP treatment in which the c-di-GMP used was independently synthesized. The results from this macroscopic analysis indicate that *S. aureus* respond to extracellular c-di-GMP and that c-di-GMP treatment inhibits *S. aureus* cell aggregation in human and animal isolates.

Figure 7A:
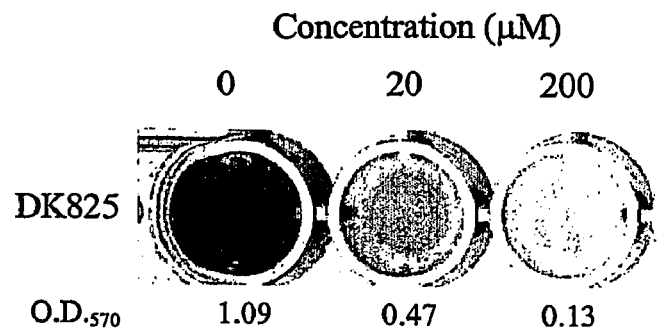
FIGS. 7A-7C show the effect of c-di-GMP on the ability of *S. aureus* human clinical isolates to form biofilms on a polystyrene surface using microtiter plates. Inhibition of biofilm formation in wells of a microtiter plate by *S. aureus* strain DK825 in TSB and 0.25% glucose treated with various concentrations of c-di-GMP for 24 h and stained with crystal violet. Visual appearance and $O.D._{570}$ values of the wells are shown (FIG. 7A). Quantitative analysis of dose-response of the inhibition of biofilm formation in *S. aureus* strain DK825 treated with c-di-GMP (FIG. 7B). Quantitative analysis of the inhibition of biofilm formation in hyperbiofilm *S. aureus* strain 15981 treated with c-di-GMP (FIG. 7C).
Figure 7B:
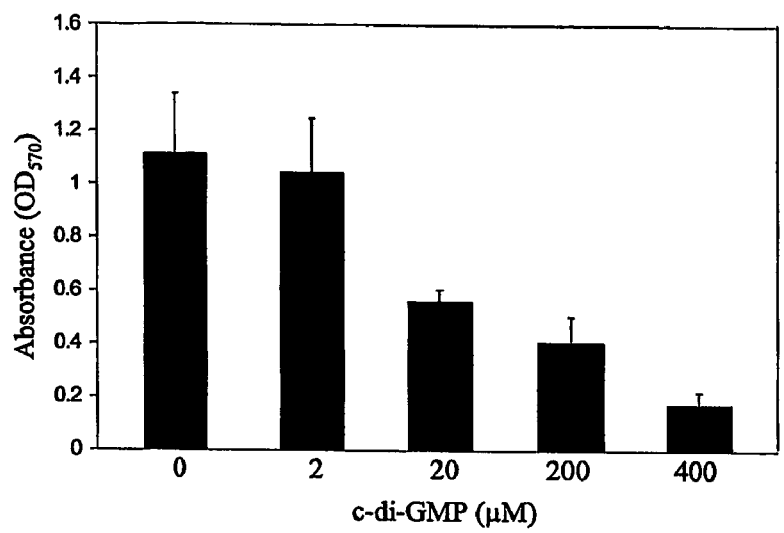
Figure 7C:
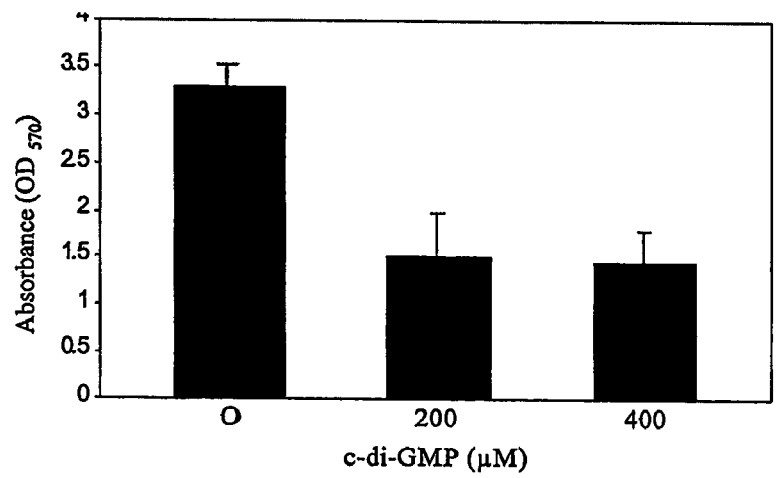

In order to further study the basis underlying the macroscopic difference observed between treated and untreated cultures described above, the cells in these cultures were vortexed, Gram-stained and visualized by light microscopy. The name *Staphylococcus* is derived from the Greek meaning "bunch of grapes". However, Gram-stained examination of the DK825 c-di-GMP treated cultures showed dramatically less cell-to-cell interactions and clumping in liquid media (FIG. 6C) than untreated cells that showed typical grape-like clusters (FIG. 6D). Similar to the findings in FIG. 6 and consistent with the macroscopic analyses, less intercellular interactions and clumping was observed by Gram-stain and light microscopy for the wildtype bovine mastitis strains (V329, V299, V315) (data not shown). It is important to note that wildtype strain V329 is bap-positive icaADBC positive while wildtype strains V299 and V315 are bap-negative icaADBC positive and bap-negative icaADBC negative, respectively (Cucarella et al., 2004). While most bovine mastitis isolates appear to be bap-negative as the bap gene seems to be only present in a small percentage of bovine mastitis isolates, bap appears to be absent from human isolates (Cucarella et al., 2001). In the experiments in this example, although cell aggregation in the isogenic bap mutant strain M556 was much less than its parent V329, the data suggests that c-di-GMP treatment inhibits cell clumping in M556 (FIG. 6E and 6F). This data from analyses of wildtype and mutant strains seems to imply that the inhibition of cell interactions is independent of bap and the icaADBC gene clusters. Importantly, the results of the microscopic analysis correlated with the macroscopic observations and further indicate that c-di-GMP treatment can inhibit *S. aureus* cell-to-cell (intercellular) adhesive interactions in human and bovine isolates.

c-di-GMP inhibits biofilm formation in human and bovine *S. aureus*. Given that c-di-GMP treatment inhibits *S. aureus* cell-to-cell interactions, the present inventor predicts that c-di-GMP inhibits biofilm formation. The quantitative biofilm results showed that c-di-GMP treatment inhibits *S. aureus* DK825 biofilm formation on abiotic polystyrene surfaces at 24 h in a dose-dependent manner (FIG. 7A and 7B). The inhibitory effect of extracellular c-di-GMP was seen at 20 μM (~50% reduction), 200 μM (~65% reduction) and 400 μM (~85% reduction). A similar difference in biofilm formation between treated and untreated cultures was observed after measurement at 48 h suggesting that selection for resistance to treatment did not occur (data not shown). The results also showed similar c-di-GMP inhibition of biofilm formation at 24 h in the highly adherent hyperbiofilm *S. aureus* strain 15981 at the concentrations tested (FIG. 7C). Although coagulase has been shown to be important for *S. aureus* colonization to host tissues, no difference in coagulase production (bound or free) in DK825 between treated and untreated cells was found (data not shown). The quantitative biofilm results correlate with the macroscopic and microscopic cell-to-cell aggregation data suggesting that extracellular c-di-GMP inhibits cell interactions and biofilm formation in human isolates.

Figure 8A:
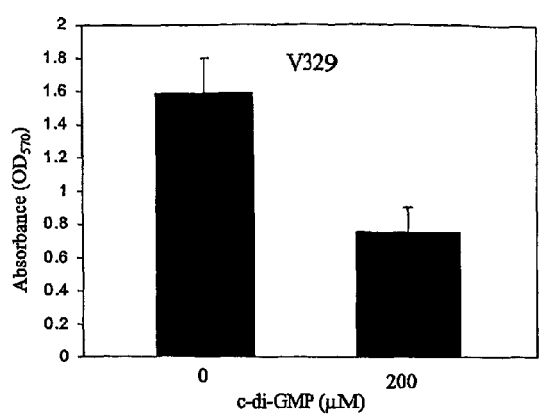
FIGS. 8A-8D are graphs showing quantitative analysis on the effect of c-di-GMP on the ability of *S. aureus* bovine mastitis isolates V329 (FIG. 8A), M556 (FIG. 8B), V299 (FIG. 8C), and V315 (FIG. 8D) to form biofilms on a polystyrene surface.
Figure 8B:
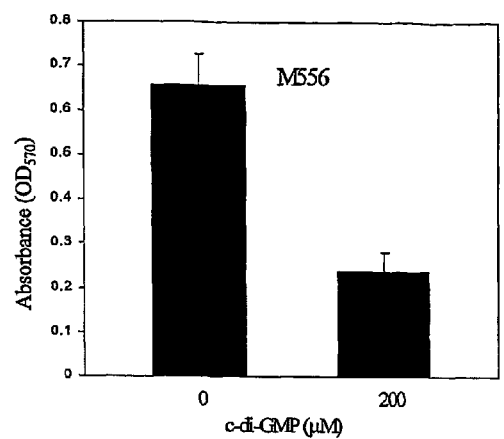
Figure 8C:
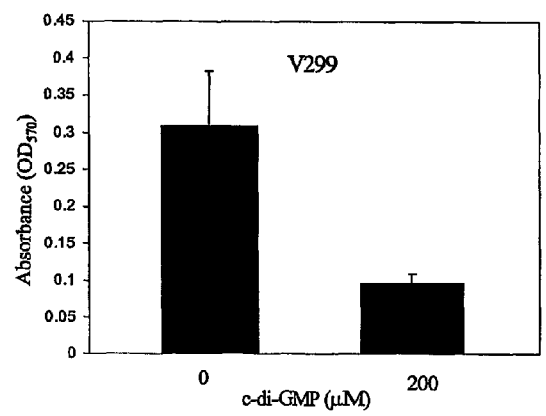
Figure 8D:
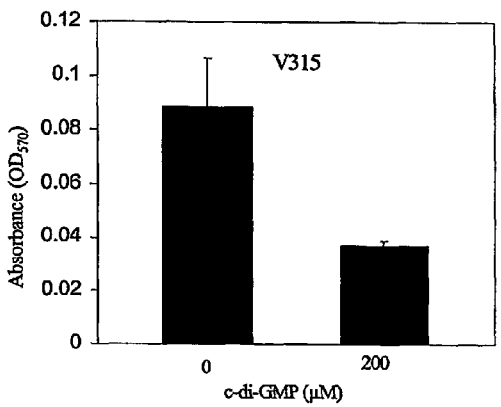

Quantitative biofilm analysis also demonstrated that c-di-GMP inhibits biofilm formation of bovine subclinical mastitis strains (FIG. 8A-8D). The wildtype bovine strain V329 was previously shown to be a strong biofilm producer on polystyrene surfaces while the isogenic bap mutant M556 was attenuated in this biofilm ability (Cucarella et al., 2001). The analysis here supports this finding but also importantly shows that like human isolates, c-di-GMP dramatically inhibits biofilm formation (~50-70% reduction) in these wildtype and mutant bovine strains as well as in the wildtype bap-negative strain V299 and the wildtype bap-negative icaADBC-negative strain V315 that formed very low levels of biofilm (FIGS. 8C and 8D). Together, these results provide further compelling evidence to indicate that c-di-GMP treatment inhibits *S. aureus* cell-to-cell interactions and cell-to-surface interactions involved in biofilm formation. These findings also suggest that cyclic dinucleotides such as c-di-GMP would be useful in preventing biofilms on clinically relevant surfaces such as medical devices and potentially in the control of human and animal infection.

The regulatory mechanisms involved in *S. aureus* biofilm formation are not fully understood. However, *S. aureus* biofilms formation is known to be mediated through the production of the extracellular polysaccharide intercellular adhesin (PIA/PNAG/PSA) that is synthesized by the icaADBC genes and also has a role in cell aggregation (Cramton et al., 1999; Maira-Litran et al., 2002 and McKenney et al., 1999). The SarA regulator has been shown to be important for biofilm formation (Beenken et al., 2003; Blevins et al., 2002 and Valle et al., 2003) as has the Bap protein (Cucarella et al., 2001 and 2002). While the exact mechanism of action remains to be determined, our results for strain 15981 suggest the mechanism might be agr-independent and our earlier studies with the bovine isolates suggest that the mechanism might be independent of bap and icaADBC.

Figure 9A:
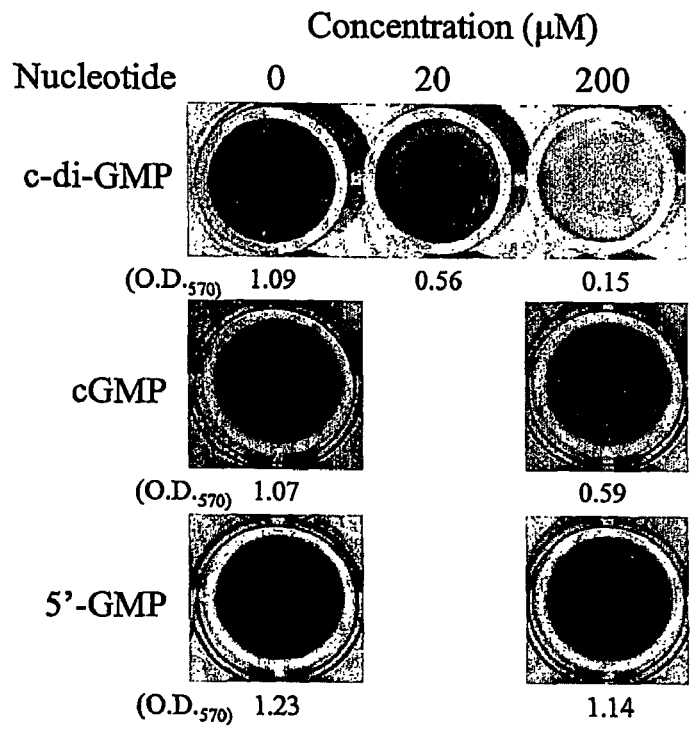
FIGS. 9A and 9B show the effect of guanosine nucleotide analogs on inhibiting S. aureus biofilm formation on polystyrene surfaces. Inhibition of biofilm formation in wells of a microtiter plate by S. aureus DK825 in TSB and 0.25% glucose treated with the nucleotides c-di-GMP, cGMP and 5'-GMP. Visual appearance and $O.D._{570}$ values of the wells are shown in FIG. 9A. Quantitative biofilm analysis on the effect of 5'-GMP, cGMP and c-di-GMP treatment on biofilm formation is shown in FIG. 9B.
Figure 9B:
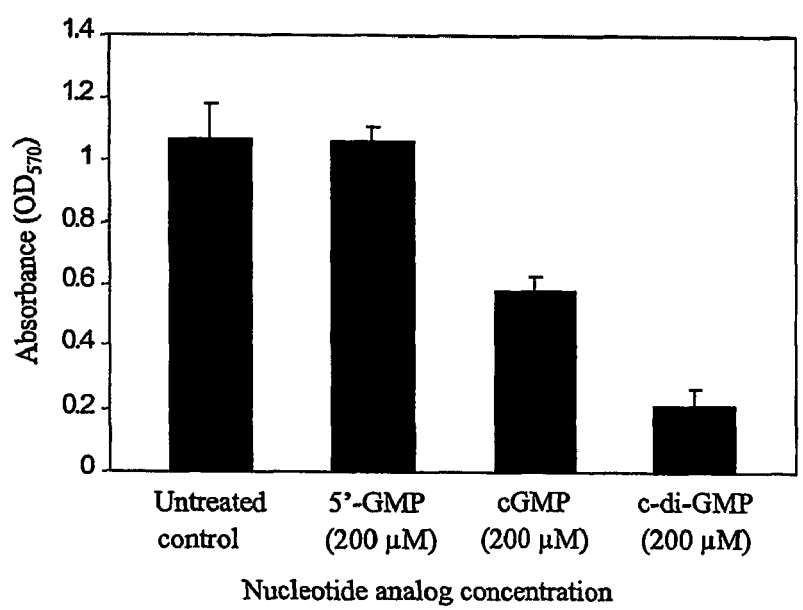

Effect of cGMP and 5'-GMP on biofilm formation. Based on the observed effects with c-di-GMP, the laboratory of the present inventor then tested whether treating cultures with extracellular guanosine nucleotide analogs such as cGMP (guanosine 3', 5'-cyclic monophosphate) and 5'-GMP (guanosine 5'-monophosphate) at the same concentration (200 µM) could also inhibit *S. aureus* DK825 biofilm formation. These experiments were performed to rule out the possibility that the effects on biofilm observed in the studies in this example were merely due to the presence of extracellular guanosine nucleotides in general or cyclic guanosine (mononucleotide) analogs. These two particular nucleotides were also chosen as the structure of c-di-GMP is somewhat similar to two cGMP molecules being linked head-to-tail (3'-5') and 5'-GMP is a known breakdown product of c-di-GMP (Ross et al., 1991). The addition of cGMP to the growth medium was found to inhibit biofilm formation (~40%) but to a much lesser extent than c-di-GMP while 5'-GMP had no effect on biofilm formation compared to c-di-GMP (FIGS. 9A and 9B). These findings indicate that the inhibitory effect observed with c-di-GMP compared to cGMP is not due to the molecule merely having a guanosine base or merely being cyclic in nature but is somehow unique to its cyclic dinucleotide structure. It is believed that the overall lack of potency of cGMP and 5'-GMP in their ability to inhibit biofilm formation in *S. aureus* compared to c-di-GMP further highlights the importance, novelty and perhaps specificity and affinity of c-di-GMP in its mechanism of action and effect on the cell. Considering the unusual shape and structure of the molecule, it is possible that it might bind with some specificity to a particular cell (or cell wall) target or receptor.

Effect of c-di-GMP treatment on *S. aureus* pre-formed biofilms. Since data presented in this example showed that c-di-GMP treatment inhibited biofilm formation in *S. aureus* strains DK825 and 15981, the hypothesis that extracellular c-di-GMP has an effect on pre-formed established biofilms was tested. The results obtained showed that c-di-GMP treatment (200 µM) of a 24 h pre-formed biofilm blocks further biofilm development (~75% reduction) compared to the untreated control (FIG. 10). Based on these data, it appears that c-di-GMP inhibits both the initial formation of biofilms and the further development of pre-formed biofilms.

c-di-GMP treatment inhibits *S. aureus* adherence to human epithelial cells. Studies examining the adherence of *S. aureus* to epithelial cell monolayers and the effect of potential therapeutic agents to inhibit adherence have been performed (Balaban et al., 2003; Cucarella et al., 2002; Matsuura et al., 1996; Miyake et al., 1989 and 1991; Roche et al., 2003; and Wyatt et al., 1990). The data from the studies here showed that treatment with 2- and 20 µM c-di-GMP did not show any obvious effect on adherence. However, compared to untreated controls (FIG. 11A), treatment with 200 µM c-di-GMP reduced the numbers of *S. aureus* cells adhering to HeLa cells (FIG. 11B). The data indicated that c-di-GMP treatment results in an average reduction in adherence from 12 bacteria/cell to 4 bacteria/cell (~66% reduction). Experiments examining the effects of various concentrations (0-, 25-, 50-, 100-, 200- and 400 µM) of c-di-GMP on HeLa cells prepared as described above in complete media (but in the absence of bacteria) showed no obvious visible effect on HeLa cell morphology examined microscopically at 12-, 24- and 48 h incubation. While the molecular basis for c-di-GMP inhibiting *S. aureus* epithelial cell adherence is not yet understood, these in vitro data are clearly consistent with previous biofilm results using polystyrene (abiotic) surfaces and suggest that c-di-GMP can also be used to inhibit biofilm formation of epithelial cell (biotic) surfaces.

Safety and Toxicity tests. Analysis of HeLa cells showed that c-di-GMP treatment with concentrations up to 400 µM did not cause any obvious changes in cell morphology after 24 h exposure. However, HeLa cells treated with 400 µM c-di-GMP did appear to undergo morphological changes after 48 h exposure. These findings suggest that c-di-GMP at concentrations <400 µM appear to be relatively noncytotoxic to these epithelial cells under the conditions tested.

The safety and potential lethality of c-di-GMP was further examined in CD-1 mice. In these studies, examination of the mice 24 h after c-di-GMP treatment (50 µL of 200 µM, orally) showed all mice were alive and no lethal effects were observed. Following sacrifice, various tissues and fluids were collected for future histological and biochemical analysis. Although the level of tissue distribution following c-di-GMP treatment and its potential tissue toxicity is not yet known, but is being currently studied, the in vivo studies show that c-di-GMP treatment at this concentration is nonlethal in mice and support other data from the laboratory of the present inventor indicating that c-di-GMP is relatively safe and nontoxic.

Possible mechanism of action of c-di-GMP on *S. aureus*. Studies in the Gram-negative bacterial species *A. xylinum* showed that c-di-GMP is an intracellular signaling molecule and does not appear able to enter these bacterial cells. Based on the findings here in *S. aureus*, a Gram-positive species, it is speculated that *S. aureus* can sense and repond to extracellular c-di-GMP. These findings suggest that extracellular c-di-GMP treatment and the resulting inhibition of cell-to-cell interactions and biofilm formation might involve c-di-GMP binding to a receptor (possibly exposed on the cell surface) which then triggers signaling events modulating gene and protein expression. As c-di-GMP has been reported to be able to enter eukaryotic cells (Steinberger et al., 1999), another possibility is that c-di-GMP might be able to enter *S. aureus* and trigger changes in protein expression. Regardless of the molecular mechanism involved, the findings in this example clearly indicate that c-di-GMP treatment inhibits cell-to-cell interactions and biofilm formation in *S. aureus*. This ability would be a valuable auxiliary property to antimicrobial treatments as it might increase the availability of the bacterial target site to the antibiotic.

Example 4

Figure 12:
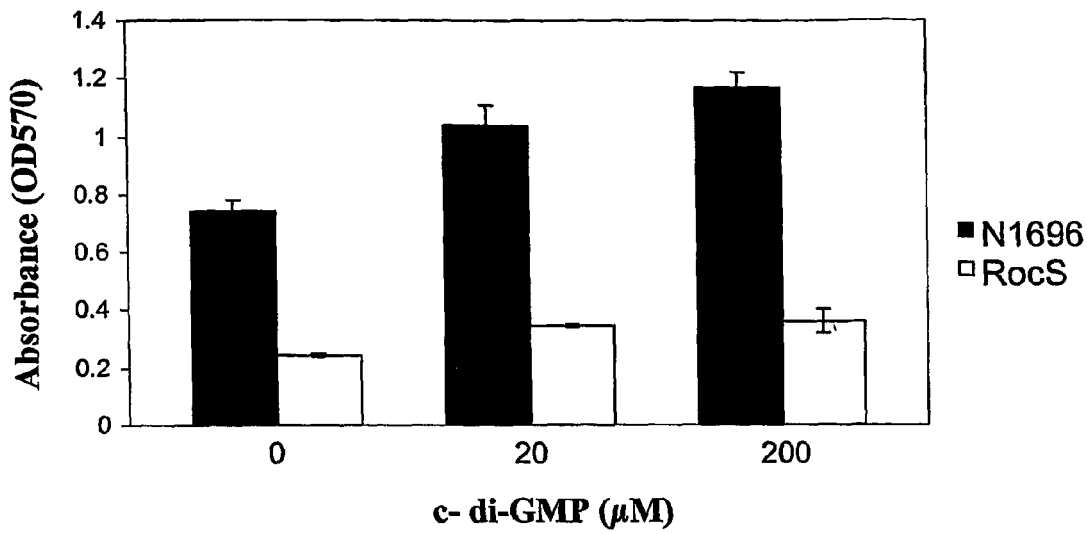
FIG. 12 is a graph showing the effect of c-di-GMP on biofilm formation in V. cholerae strain N16961 and in a RocS mutant. Results are averages based on at least three independent colonies.

Extracellular c-di-GMP regulates *V. cholerae* biofilm formation. Tests examining the stability of the molecule under different buffers and temperatures have shown it is stable for at least several months in physiological saline at 4° C. and stable following boiling for 10 min and stable following treatment in acid (pH 3) and alkali (pH 10) for 1 h. Using a standard crystal violet quantitative biofilm assay following 24 h static incubation in glass test tubes containing LB broth supplemented with various concentrations of c-di-GMP, extracellular c-di-GMP was found to increase biofilm formation in *V. cholerae* N16961 in a dose-dependent manner compared to untreated controls (FIG. 12). These findings are consistent with findings in *G. xylinum* that increasing c-di-GMP levels increases cellulose production. The results obtained did not appear to be due to differences in growth rate between treated and untreated cultures. Interestingly, the RocS mutant shows less biofilm forming ability compared to the wildtype strain and showed increased biofilm forming activity in response to c-di-GMP. Given that RocS is linked to c-di-GMP, the inability of extracellular c-di-GMP to restore wildtype biofilm levels in the mutant could imply that the RocS mutant is not only defective in c-di-GMP regulation but in other properties associated with biofilm formation.

Example 5

In a physiological environment, such as the surface of a catheter, *S. aureus* is expected to colonize and form biofilms enabling the persistence of cells under conditions of flow. To mimic these conditions in vitro, and to further explore the potential use of c-di-GMP as a novel anti-biofilm agent, a continuous culture Flow-cell biofilm model will be used to study c-di-GMP treatment on *S. aureus* biofilm formation on silicon and stainless steel surfaces. The effect of treatment with c-di-GMP alone and treatment with c-di-GMP in combination with the commonly used antibiotic oxacillin to increase susceptibility and reduce biofilm formation on silicon and stainless steel will also be tested.

Figure 13:
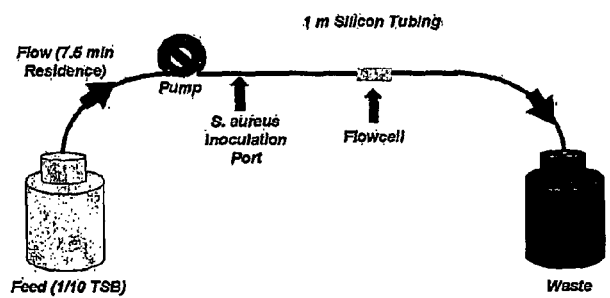
FIG. 13 is a schematic representation of a biofilm growth reactor system, which is a once-through system entirely enclosed within a 37° C. incubator. $10^7$ CFUs are injected into the reactor tubing and allowed to attach for 30 min at which time flow is restored to the system. Biofilms may be harvested by removing the flow-cell or opening the silicon tubing and scraping the inner lumen.
Figure 14:
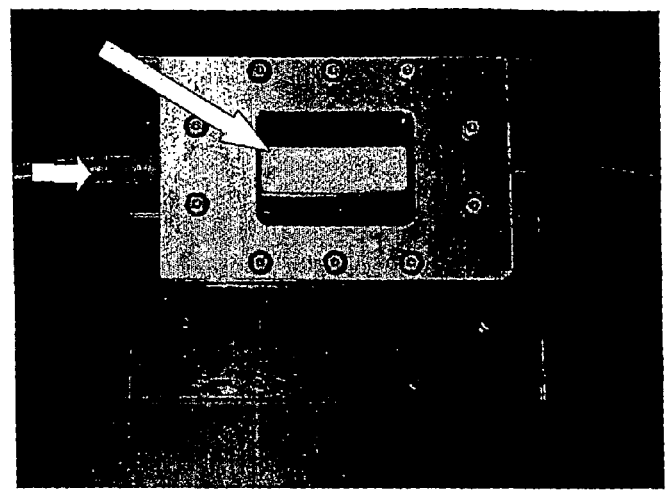
FIG. 14 shows a sealed flowcell (Protofab, Inc., Bozeman, M T) which is inserted inline into the biofilm growth reactor system shown in FIG. 13 and is used to obtain biofilm samples attached to various surfaces including PMMA and stainless steel. Inserts are easily removed for biofilm harvest.

Flow-cell Biofilm Model to Test the Effect of c-di-GMP on *S. aureus* Biofilm Formation i. Growth Conditions For biofilm cultures grown under dynamic flow on silicon surfaces, the interior surfaces of 1 m sections of silicon tubing (size 16, resulting volume of 7 ml, Masterflex) will be used as attachment surfaces (see FIG. 13 for reactor diagram). In experiments in which biofilms are to be grown within a flow-cell, a Protofab Sealed Flowcell will be used (FIG. 14). This flow-cell can be incorporated into the middle of the 1 m sections of silicon tubing in the reactor system and has an insert (either PMMA or stainless steel) that can be removed and harvested for adherent biofilm. The hypothesis that c-di-GMP treatment a) inhibits biofilm formation on silicon and steel; and b) reduces pre-formed biofilms on silicon and steel will be tested.

ii. Effect on Biofilm Formation

*S. aureus* DK825 cultures will be grown overnight at 37° C. with shaking in TSB. The overnight culture is then diluted 1:1000 in fresh TSB and samples are grown with shaking at 37° C. until they have attained logarithmic growth phase. An aliquot (5 ml) of this logarithmic phase culture ($\approx 10^7$ CFU) containing 200 µM c-di-GMP (treated) and a sample inoculated with an identical aliquot of 0.9% NaCl (untreated) will be injected into the tubing and allowed to attach for 30 min before the flow of TSB (with c-di-GMP and without) is started (0.7 ml/min). Since the residence time is 7.5 minutes (less than the $\approx$30-40 minute bacterial doubling time in batch growth conditions), only attached organisms are retained on the surfaces. All biofilm experiments will be conducted within a 37° C. incubator and all samplings will be performed in triplicate. Biofilm samples will be harvested 24 h post-inoculation by scraping the silicon and steel surfaces, thereby loosening the biofilm. Each sample will be suspended in 2 ml PBS and vortexed to disrupt any aggregated cells. Serial dilutions of the vortexed samples will be plated out onto blood agar plates in order to enumerate cfu/ml of treated and untreated samples and therefore the effect of c-di-GMP on the viability of *S. aureus* in a model biofilm system on silicon and steel.

iii. Effect on Pre-formed Biofilms

*S. aureus* DK825 will be grown overnight at 37° C. with shaking in TSB. The overnight culture is then diluted 1:1000 in fresh TSB and samples are grown with shaking at 37° C. until they have attained logarithmic growth phase. An aliquot (5 ml) of this logarithmic phase culture ($\approx 10^7$ CFU) without c-di-GMP will be injected into the tubing and allowed to attach for 30 min before the flow of TSB either with 200 µM c-di-GMP (treated) or containing an identical aliquot of 0.9% NaCl (untreated) is started (0.7 ml/min). Since the residence time is 7.5 minutes (less than the $\approx$30-40 minute bacterial doubling time in batch growth conditions), only attached organisms are retained on the surfaces. All biofilm experiments are conducted within a 37° C. incubator and all samplings will be performed in triplicate. Biofilm samples will then be harvested 24 h post-inoculation by scraping the silicon and steel surfaces, thereby loosening the biofilm. Each sample will be suspended in 2 ml PBS and vortexed to disrupt any aggregated cells. Serial dilutions of the vortexed samples will be plated out onto blood agar plates in order to enumerate cfu/ml of treated and untreated samples and therefore the effect of c-di-GMP on the viability of *S. aureus* in a model biofilm system on silicon and steel will be tested. Since the results in Example 3 suggest that c-di-GMP treatment reduces cell-to-cell interactions, cell-to-surface interactions on plastic, epithelial cell adherence and reduces *S. aureus* cell viability, the present inventor expects to find that c-di-GMP will inhibit biofilm formation on silicon and steel and will also reduce pre-formed biofilm levels.

Flow-cell Biofilm Model to Test the Effect of c-di-GMP and Antibiotics on Susceptibility and Biofilm Formation Based on preliminary data in the laboratory of the present inventor, it is expected that c-di-GMP treatment increases the antibiotic susceptibility of *S. aureus*. Therefore, to further explore the potential use of c-di-GMP as an "antibiofilm" agent, the hypothesis that c-di-GMP treatment increases antibiotic susceptibility will be tested. Initially, the effect of c-di-GMP alone and in combination with the commonly used antibiotic oxacillin to increase the susceptibility of biofilm-associated *S. aureus* will be tested. These studies will use the continuous culture flow-cell biofilm model described above to analyze *S. aureus* biofilm formation in the presence of c-di-GMP alone and in combination.

To study the potential of any combined antibiotic activity (synergy) of c-di-GMP and oxacillin against *S. aureus* biofilms, a modification of the flow-cell biofilm model described above will be used. The MIC of oxacillin will first be determined using standard tube assays by testing concentrations 1-1,024 µg/ml using National Committee for Clinical Laboratory Standards (NCCLS). The MIC of oxacillin in the presence of 200 µM c-di-GMP will be quantitated to determine if there is any reduction in susceptibility and synergy.

For studies in the biofilm model, *S. aureus* DK825 will be grown overnight at 37° C. with shaking in TSB. The overnight culture is then diluted 1:1000 in fresh TSB and samples are grown with shaking at 37° C. until they have attained logarithmic growth phase. An aliquot (5 ml) of this logarithmic phase culture ($\approx 10^7$ CFU) containing i) 200 µM c-di-GMP alone, ii) c-di-GMP+oxacillin (concentration determined above), iii) oxacillin alone, and iv) 0.9% NaCl alone will be injected into the tubing and allowed to attach for 30 min before the flow of TSB (same conditions as above) is started (0.7 ml/min). Since the residence time is 7.5 minutes (less than the $\approx$30-40 minute bacterial doubling time in batch growth conditions), only attached organisms are retained on the surfaces. All biofilm experiments are conducted within a 37° C. incubator and all samplings will be performed in triplicate. Biofilm samples will be harvested 24 h post-inoculation by scraping the silicon surface, thereby loosening the biofilm. Each sample will be suspended in 2 ml PBS and vortexed to disrupt any aggregated cells. Serial dilutions of the vortexed samples will be plated out onto blood agar plates in order to enumerate cfu/ml of treated and untreated samples and therefore the effect of c-di-GMP on the antibiotic susceptibility and inhibition of *S. aureus* biofilm formation. Time-kill curves similar to the method of Domaracki et al. (Domaracki et al., 2000) will also be performed to study the effect of combinations of c-di-GMP and oxacillin on the growth of MRSA strain DK825 throughout a 12-h incubation in the biofilm model described above. The strain will be tested in TSB plus 2% NaCl with a sub-MIC concentration of oxacillin alone (concentration to be used will be determined above) or in combination with c-di-GMP (200 µM). In these studies, viability counts will be performed at 0, 3, 6, and 12 h by plating samples from the flow-cell system onto blood agar.

The biofilm model system used in this example mimics the clinical setting (e.g., a medical device) as a constant concentration of the "drug" is being administered with the flow-cell system and avoids re-administering drug at later intervals. Since data in Exmaple 3 above suggests that c-di-GMP inhibits cell viability by approximately 1-log and inhibits cell-to-cell interactions and biofilms under the previous conditions tested, reductions with c-di-GMP treatment in this model biofilm system are expected. While it is possible, no antagonism to oxacillin susceptibility is anticipated. Also, while unlikely, given the inhibition of cell-to-cell interactions and thus the presumed better access of antimicrobial targets, it is possible that c-di-GMP will not be synergistic and will not increase the antibiotic susceptibility of DK825. However, the present inventor expects to find that combination c-di-GMP treatment will produce a synergistic effect and cause a measurable increase in antibiotic susceptibility in *S. aureus* compared to oxacillin or c-di-GMP treatment alone. Such a synergistic effect would demonstrate that c-di-GMP could be used in combination with other drugs to increase antimicrobial activity. If differences in susceptibility are found in this system, these findings would support c-di-GMP having useful antimicrobial activity, and further susceptibility studies will be performed using different antibiotics. Time-kill curves are expected to show an enhancement of killing in the presence of combinations of c-di-GMP and oxacillin. Synergy would be indicated if, for example, 2-logs of killing were found compared to the starting inoculum for *S. aureus*. This study might indicate that sub-MICs of oxacillin together with c-di-GMP are effective in killing or at least increasing the susceptibility of MRSA. If synergy is found, further investigations could be conducted with animal models to see if a c-di-GMP-oxacillin combination is synergistic in vivo. Additional testing could also be performed to determine the prevalence of a synergistic effect in different species of staphylococci and in the clinical staphylococcal population.

Example 6

The sequencing of the *V. cholerae* strain N16961 (Heidelberg et al., 2000) has enabled new approaches to studying this pathogen. A microarray of the N16961 genome, represented by 3884 oligos (1 oligo/gene of the genome) was printed on polylysine-coated glass microscope slides (Corning) using a microarray maker, PS5200 (Cartesian Technologies). The oligonucleotide probes were suspended in 20 mMTris, 50 mM KCl, pH 6.5, 50% DMSO as a printing buffer, then arrayed in a 96 well plate and spotted under appropriate conditions of temperature and humidity. After printing, the slide is dried and then the spotted DNA is bound to the slide by UV-crosslinking at 60 mJ using a Stratalinker (Stratagene) and baked at 80 C for two hours. Target nucleic acid will be labeled either with Cy3 or Cy5 fluorescent dyes.

Proteins with a GGDEF domain have regulatory roles and are thought to be associated with c-di-GMP. Since *V. cholerae* contains approximately 41 GGDEF proteins (Galperin et al., 2001), the present inventor expects that c-di-GMP regulates many genes and important processes in *V. cholerae* (and other pathogens), including virulence. This hypothesis will be tested using a transcriptional profiling approach to study the transcriptome of *V. cholerae* st rain N16961.

In these initial studies wildtype cells grown in the presence and absence of c-di-GMP will be compared to identify genes whose expression is affected by c-di-GMP. RNA from log phase cells grown in LB broth at 37° C. shaking will be extracted from the cultures after adjusting to $OD_{600}$ 0.3-0.4 using RNA Easy kit (Qiagen) and treated with DNase I (Qiagen) before labeling. For labeling reactions, mRNA will be labeled either with Cy3 or Cy5 dyes. Both labeling reactions will be performed with all samples to account for systematic variation based on the labeling reaction and characteristics of the dyes. The fluorescent label will be incorporated using the standard method involving reverse transcriptase with amino acyl-labeled nucleotides. Unincorporated dNTPs and the oligo-dT primers will be removed by ethanol precipitation. The label is incorporated in a second step. Amino acyl labeling was found to provide a more uniformly product from sample to sample in control samples. In order to maximize the signal and minimize the background, the microarrays will be prehybridized in 1 M NaCl, 50 mM Tris pH 7.0, 50% formamide, 10% dextran sulfate, 1% SDS and 1% bovine serum albumin for 1 hr and 42 C. The labeled target nucleic acid is denatured at 95° C. for 5 minutes, cooled to 4° C. and added to the hybridization chamber containing the slide. The hybridization reaction incubates at 42° C. overnight. The slide is removed from the chamber and washed with 0.1 M NaCl and 0.1% SDS for 5 minutes at room temperature. The slide is then allowed to air dry. The hybridized microarrays will be scanned in a Scan Array 3000 (GSI Lumonics) scanner. The scanner uses lasers operating at 633 nm and 543 nm to excite Cy5 and Cy3 respectively. Cy5 is scanned first because it is more sensitive to photodegradation. Data from each fluorescent channel is stored separately as a TIFF file. The Irnagene (Biodiscovery) software will be used to identify the location of each spot, link the spot identifiers, measure the background density around each spot, and record the fluorescent intensities into a simple flat file. Data from replicate spots and from spots representing the same taxa will be compared, outliers discarded and the others averaged using the software GeneSight (Biodiscovery).

Experimental Design of microarray data analysis. To compare the expression profile of the cells grown with and without c-di-GMP, a Latin square design will be used. For each pair of samples (with and without c-di-GMP), two aliquots of each sample will be prepared, i.e., two from the sample without c-di-GMP (A1 and A2) and two from the sample with c-di-GMP (B1 and B2). The first array will consist of the first untreated sample (A1) labeled red and hybridized with the first treated sample (B1) labeled green. The second array will consist of the second treated sample (B2) labeled red and hybridized with the second untreated sample (A2) labeled green. The layout of the Latin square design is shown below in Table 4:

TABLE 4

| Dye | Chip 1 | Chip 2 |
|---|---|---|
| Red | A1 | A2 |
| Green | B1 | B2 |

This design will be very effective in eliminating of dye bias for each with- and without c-di-GMP comparison. Six chips will be used since the Latin square design will be applied for each triplicate pair of samples.

Data Processing. Typically, the background of a microarray image is not uniform over the entire array. The procedure of extraction of local background intensity will be implemented. The (background subtracted) intensity values from the two channels from each array will be plotted against one another to check the quality of the data, namely that data for all genes whose transcription levels have remained essentially unchanged should fall on a straight diagonal line. The range of the values should be nearly the same for all channels, and neither channel should be saturated. Log transformation ensures that the data are approximately normally distributed within each gene, which improves statistical performance of the analysis of variance. The method is fairly robust to departures from normality. The log base2 scale will be used in our analysis because each unit after transformation corresponds to a two-fold difference.

Normalization. To account for experiment-wide systematic effects that may bias inference made on the data from the individual genes, an ANOVA model which fits the raw fluorescence intensity values as a function of dye and array will be used to perform a normalization (Wolfinger et al., 2001). Let $Y_{gijk}$ be the base-2 logarithm of the background-corrected intensity value from gene g, variety i (i=1,2), dye j (j=1,2) and array k (k=1,*,6). The genetic term "variety" here signifies the type of the mRNA samples (from N16961 wildtype or VpsR mutant cells). The normalization model is:

$$y_{gijk} = \mu + D_j + A_k + (DA)_{jk} + \epsilon_{gijk}.\quad(1)$$

where μ is an overall mean, D is the main effect for dyes, A is the main effect for arrays, DA is the interaction effect of arrays and dyes, and ε is a random error. In model (1), the main and interaction effects may be treated as random effects. The residuals from this model, computed by subtracting the fitted values for the effects from the $Y_{gijk}$ values can be viewed as the relative fluorescence intensities for each gene relative to the sample mean. The basic idea of the normalization model is to remove overall differences between the dyes and between the arrays.

Gene-Specific Significance Models. To identify differentially expressed genes between treated and untreated cells, perform gene-specific ANOVAs (Wolfinger et al., 2001) will be performed. Let $r_{gijk}$ denote the residuals from the model (1), i.e., the relative fluorescence intensities for gene g. The gene model is:

$$r_{gijk} = V_{gi} + D_{gj} + (VD)_{gij} + \epsilon_{gijk}.\quad(2)$$

All effects are indexed by g and are assumed to serve similar roles to those in model (1) but at the gene level, V is the main effect for varieties. Except V, other effects may be treated as random effects. The estimates of primary interest are those of the $V_{gi}$ effects, which measures the variety effects for each gene. Differences between these effects will be tested by using SAS procedure such as PROC MIXED within a gene. Based on this statistical approach, the cut-off will be established. Finally, a list of differentially expressed genes will be selected for each comparison.

Alternative Analysis. The Significant Analysis of Microarrays (SAM) (Tusher et al., 2001) is an alternative to the ANOVA approach. SAM, developed by Rob Tibshirani, Stanford University, is a statistical method adapted specifically for microarrays. SAM assigns each gene with a score that is based on its change in gene expression relative to the standard deviation of repeated measurements for that gene. Genes with scores greater than a threshold are deemed potentially significant. This procedure provides the false discovery rate (FDR), the percentage of such genes identified by chance. By controlling proper FDR (such as 0.05), a set of differentially expressed genes will be identified for each comparison. In comparison with the results of ANOVA, more attention will be paid on those genes identified by both methods.

Expected results and interpretations. These transcriptional profiling studies will identify genes that are regulated by c-di-GMP. Specific genes of interest (e.g. regulatory and virulence) that are significantly activated or repressed by c-di-GMP will be confirmed by RT-PCR and can be further studied. Even if c-di-GMP regulates known virulence genes, this would represent a novel signaling cascade controlling virulence. Using a similar approach, the effect of c-di-GMP and analogs in the regulation of other pathogens can be studied.

Example 7

A *Staphylococcus aureus* amplicon-based microarray was constructed by TIGR (The Institute for Genomic Research, Rockville, Md.) and contains amplicons representing segments of 2480 ORFs from *Staphylococcus aureus* strain COL (reference strain), *Staphylococcus aureus* strain MU50, *Staphylococcus aureus* strain MW2, and *Staphylococcus aureus* strain N315. The microarray is also printed with control transcript spots.

Table 5 below show a subset of the microarray data obtained on the effects of c-di-GMP (200 μM) on *S. aureus* strain DK825. Only some of the known regulatory, virulence- and biofilm-associated genes whose expression (level of transcription) is differentially regulated (either up-regulated or down-regulated) in response to c-di-GMP are shown in this table. The fold-increase or decrease in expression for each gene, as determined by the intensity of hybridization of the amplicon spots on the microarray to RNA isolated from *S. aureus* treated with 200 μM c-di-GMP compared with the intensity of hybridization to RNA isolated from the *S. aureus* untreated control, is presented.

TABLE 5

| Up-regulated | |
|---|---|
| agrA (quorum sensing) | 5.4 |
| agrB (quorum sensing) | 5.8 |
| agrC (quorum sensing) | 2.0 |
| agrD (quorum sensing) | 2.2 |
| saeR (response regulator) | 2.5 |
| saeS (histidine kinase) | 1.5 |
| rsbW (anti-sigmaB) | 4.5 |

TABLE 5-continued

| | |
|---|---|
| PBP-2 | 2.0 |
| PBP-4 | 1.7 |
| Down-regulated | |
| fnbB (fibronectin binding) | 0.47 |
| fbnA (fibrinogen binding) | 0.66 |
| clfA (clumping factor) | 0.54 |
| clfB (clumping factor) | 0.43 |
| icaR (intercellular adhesin) | 0.62 |
| collagen adhesin | 0.55 |
| vacuolating cytotoxin | 0.56 |
| enterotoxin A | 0.54 |
| enterotoxin 1 | 0.35 |
| exfoliative toxin | 0.52 |
| toxic shock syndrome toxin | 0.45 |

The data indicate that c-di-GMP affects the expression of numerous genes in *S. aureus*. Notably, the c-di-GMP molecule affects expression of quorum sensing (agr) genes, regulators with known roles in virulence, toxin genes and colonization and biofilm-associated genes. The data are consistent with *S. aureus* being attenuated for biofilm formation, colonization, cell clumping, toxin activity and overall (regulation) of virulence. The rsbw gene encodes an anti-sigmaB factor that represses the expression of sigmaB which is important for full virulence. Therefore, increased expression of rsbw is consistent with decreased virulence.

Example 8

Figure 15:
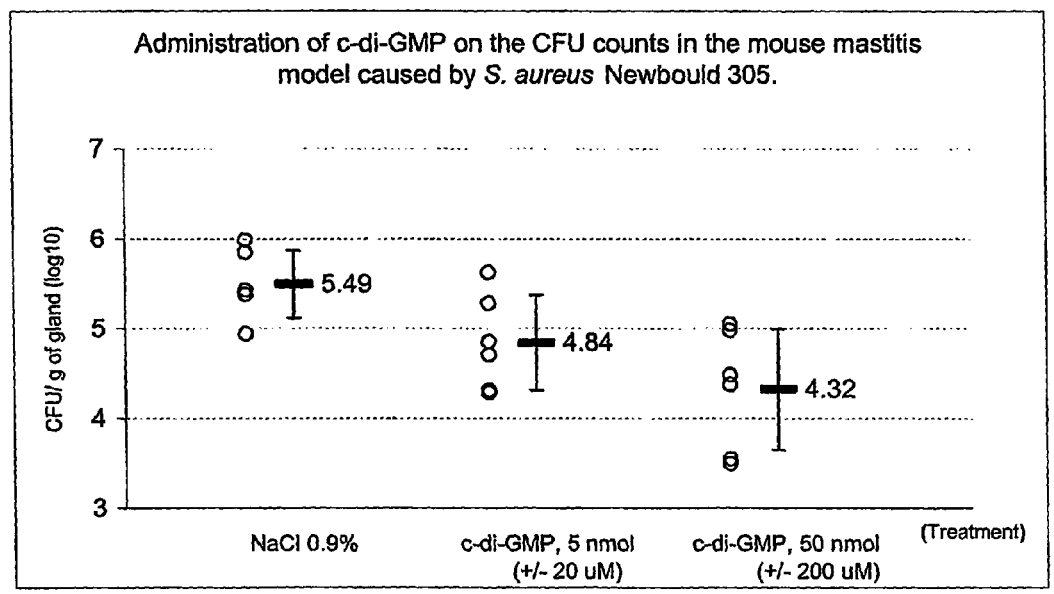
FIG. 15 is a graph showing the effect of c-di-GMP on CFU counts of S. aureus Newbould 305 strain in a mouse mastitis model.

A mouse mastitis model of *S. aurreus* infection using the *S. aureus* Newbould 305 strain (Brouillette et al., 2003, 2004a and 2004b) was used to show the effectiveness of treatment with c-di-GMP. Three mice per group and two glands per mouse were used for a total of six samples per treatment. 100 CFU (colony forming units) of *S. aureus* Newbould 305 strain were inoculated into each mammary gland. Five or 50 nanomoles of c-di-GMP was administered by injection twice into each mammary gland at 0 hr. (pre-mixed with the *S. aureus* inoculum in 100 µl volume, i.e., 50 or 500 µM concentration) and at 4 hr. post-infection (in 50 µl, i.e., 100 or 1000 µM). The mammary glands were harvested at 10 hrs. post-infection. Considering the volume of the mammary gland with milk to be about 250 µl, the final concentration of c-di-GMP in the mammary gland at each injection was estimated to be 20 µM or 200 µM. Treatment with c-di-GMP clearly show a significant dose-dependent suppressing effect (reduction in CFU counts) of c-di-GMP on the ability of *S. aureus* to multiply or colonize in the mammary gland (FIG. 15). The results show that 50 nanomoles of c-di-GMP injected into the mammary gland in vivo significantly inhibits *S. aureus* infection of the mammary gland by at least 10-fold (T test: p=0.004; Mann-Whitney U-test: p=0.009).

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Ali, A., Johnson, J. A., Franco, A. A., Metzger, D. J., Connell, T. D., Morris, J. G. J. and Sozhamannan, S. (2000) Infection and Immunity 68, 1967-1974.

Ali, A., M. H. Rashid, and D. K. R. Karaolis. 2002. High-frequency rugose exopolysaccharide production in *Vibrio cholerae*. Appl Environ Microbiol. 68:5773-5778.

Ali, A., Mahmud, Z. H., Morris, J. G., Jr., Sozhamannan, S. and Johnson, J. A (2000) Infection and Immunity 68, 6857-6864.

Ali, A., Rashid, M. H. and Karaolis, D. K. R. (2002) Applied and Environmental Microbiology 68, 5773-5778.

Altschul, A. F., W. Gish, W. Miller, E. W. Myers, and D. J. Lipman. 1990 Basic local alignment search tool. J. Mol. Biol. 215:403-410.

Amikam, D., and M Benziman. 1989. Cyclic diguanylic acid and cellulose synthesis in *Agrobacterium tumefaciens*. J. Bacteriol. 171:6649-55.

Anriany, Y. A., R. M. Weiner, J. A. Johnson, C. E. De Rezende, and S. W. Joseph. 2001. *Salmonella enterica* serovar *Typhimurium* DT104 displays a rugose phenotype. Appl Environ Microbiol. 67:4048-4056.

Anriany, Y. A., Weiner, R. M., Johnson, J. A., De Rezende, C. E. and Joseph, S. W. (2001) Applied and Environmental Microbiology 67, 4048-4056.

Anwar, H., J. L. Strap, and J. W. Costerton. 1992. Establishment of aging biofilms: possible mechanism of bacterial resistance to antimicrobial therapy. Antimicrob Agents Chemother. 36:1347-1351.

Archer, G. L. 1998. *Staphylococcus aureus*: a well-armed pathogen. Clin Infect Dis. 26:1179-81.

Archibald, L., L. Phillips, D. Monnet, J. E. J. McGowan, F. Tenover, and R. Gaynes. 1997. Antimicrobial resistance in isolates from inpatients and outpatients in the United States: increasing importance of the intensive care unit. Clin Infect Dis. 24:211-5.

Ausmees, N., Mayer, R., Weinhouse, H., Volman, G., Amikam, D., Benziman, M. and Lindberg, M. (2001) FEMS Microbiol Lett 204, 163-7.

Bahrani-Mougeot, F. K., Buckles, E. L., Lockatell, C. V., Hebel, J. R., Johnson, D. E., Tang, C. M. and Donnenberg, M. S. (2002) Mol Microbiol 45, 1079-93.

Balaban, N., Y. Gov, A. Bitler, and J. R. Boelaert. 2003. Prevention of *Staphylococcus aureus* biofilm on dialysis catheters and adherence to human cells. Kidney Int. 63:340-5.

Barker, J., and S. F. Bloomfield. 2000. Survival of *Salmonella* in bathrooms and toilets in domestic homes follwoing *salmonellosis*. Journal of Applied Microbiology. 89:137-144.

Bateman, A. and Bycroft, M. (2000) J Mol Biol 299, 1113-9.

Beenken, K. E., J. S. Blevins, and M. S. Smeltzer. 2003. Mutation of sarA in *Staphylococcus aureus* limits biofilm formation. Infect. Immun. 71:4206-11.

Blevins, J. S., K. E. Beenken, M. O. Elasri, B. K. Hurlburt, and M. S. Smeltzer. 2002. Strain-dependent differences in the regulatory roles of sarA and agr in *Staphylococcus aureus*. Infect. Immun. 70:470-80.

Bomchil, N., P. Watnick, and R. Kolter. 2003. Identification and characterization of a *Vibrio cholerae* gene, mbaA, involved in maintenance of biofilm architecture. J. Bacteriol. 185:1384-90.

Bradley, S. F., M. S. Terpenning, M. A. Ramsey, L. T. Zarins, K. A. Jorgensen, W. S. Sottile, D. R. Schaberg, and C. A. Kauffman. 1991. Methicillin-resistant *Staphylococcus aureus*: colonization and infection in a long-term care facility. Ann Intern Med. 115:417-22.

Brouillette E., Talbot B. G., Malouin F. 2003. The fibronectin-binding proteins of *Staphylococcus aureus* may promote mammary gland colonization in a lactating mouse model of mastitis. Infect Immun. 71(4):2292-2295.

Brouillette E, Martinez A, Boyll B J, Allen N E, Malouin F. 2004a. Persistence of a *Staphylococcus aureus* small-colony variant under antibiotic pressure in vivo. FEMS Immunol Med Microbiol. 41(1):35-41.

Brouillette E, Grondin G, Lefebvre C, Talbot B G, Malouin F. 2004b. Mouse mastitis model of infection for antimicrobial compound efficacy studies against intracellular and extracellular forms of *Staphylococcus aureus*. Vet Microbiol. 101(4):253-62.

Cole, A. M., S. Tahk, A. Oren, D. Yoshioka, Y. H. Kim, A. Park, and T. Ganz. 2001. Determinants of *Staphylococcus aureus* nasal carriage. Clin Diagn Lab Immunol. 8:1064-9.

Connolly, J. P., Kuchma, S. L. and O'Toole, G. A. (2003) in: 103rd General meeting of the American Society for Microbiology, Washington, D.C.

Cosgrove, S. E., G. Sakoulas, E. N. Perencevich, M. J. Schwaber, A. W. Karchmer, and Y. Carmeli. 2003. Comparison of mortality associated with methicillin-resistant and methicillin-susceptible *Staphylococcus aureus* bacteremia: a meta-analysis. Clin Infect Dis. 36:53-9.

Costerton, J. W., P. S. Stewart, and E. P. Greenberg. 1999. Bacterial biofilms: a common cause of persistent infections. Science. 284:1318-1322.

Costerton, J. W., R. T. Irvin, and K. J. Cheng. 1981. The bacterial glycocalyx in nature and disease. Annu Rev Microbiol. 35:299-324.

Costerton, J. W., Z. Lewandowski, D. E. Caldwell, D. R. Korber, and H. M. Lappin-Scott. 1995. Microbial biofilms. Annu Rev Microbiol. 49:711-745.

Cramton, S. E., C. Gerke, N. F. Schnell, W. W. Nichols, and F. Gotz. 1999. The intercellular adhesion (ica) locus is present in *Staphylococcus aureus* and is required for biofilm formation. Infect. Immun. 67:5427-33.

Croft, L., Beatson, S. A., Whitchurch, C. B., Huang, B., Blakeley, R. L. and Mattick, J. S. (2000) Microbiology 146 (Pt 10), 2351-64.

Cucarella, C., C. Solano, J. Valle, B. Amorena, I. Lasa, and J. R. Penades. 2001. Bap, a *Staphylococcus aureus* surface protein involved in biofilm formation. J. Bacteriol. 183:2888-2896.

Cucarella, C., M. A. Tormo, C. Ubeda, M. P. Trotonda, M. Monzon, C. Peris, B. Amorena, I. Lasa, and J. R. Penades. 2004. Role of biofilm-associated protein bap in the pathogenesis of bovine *Staphylococcus aureus*. Infect. Immun. 72:2177-85.

Cucarella, C., M. A. Tormo, E. Knecht, B. Amorena, I. Lasa, T. J. Foster, and J. R. Penades. 2002. Expression of the biofilm-associated protein interferes with host protein receptors of *Staphylococcus aureus* and alters the infective process. Infect. Immun. 70:3180-6.

D'Argenio, D. A., M. W. Calfee, P. B. Rainey, and E. C. Pesci. 2002. Autolysis and autoaggregation in *Pseudomonas aeruginosa* colony morphology mutants. J. Bacteriol. 184:6481-9.

Davey, M. E., and G. A. O'toole. 2000. Microbial biofilms: from ecology to molecular genetics. Microbiology and Molecular Biology Reviews. 64:847-867.

Davies, D. G., and G. G. Geesey. 1995. Regulation of the alginate biosynthesis gene algc in *Pseudomonas aeruginosa* during biofilm development in continuous culture. Appl Environ Microbiol. 61:860-867.

Davis, B. M., Lawson, E. H., Sandkvist, M., Ali, A., Sozhamannan, S. and Waldor, M. K. (2000) Science 288, 333-5.

de Lorenzo, V., M. Herrero, U. Jakubzik, and K. N. Timmis. 1990. Mini-Tn5 transposon derivatives for insertion mutagenesis, promoter probing, and chromosomal insertion of cloned DNA in gram-negative eubacteria. J. Bacteriol. 172:6568-72.

Dills, W. L., C. D. Goodwin, T. M. Lincoln, J. A. Beavo, P. J. Bechtel, J. D. Corbin, and E. G. Krebs. 1979. Purification of cyclic nucleotide receptor proteins by cyclic nucleotide affinity chromatography. Adv Cyclic Nucleotide Res. 10:199-217.

Dingman, J. R., M. G. Rayner, S. Mishra, Y. Zhang, M. D. Ehrlich, J. C. Post, and G. D. Ehrlich. 1998. Correlation between presence of viable bacteria and presence of endotoxin in middle-ear effusions. J Clin Microbiol. 36:3417-3419.

Domaracki, B. E., A. M. Evans, and R. A. Venezia. 2000. Vancomycin and oxacillin synergy for methicillin-resistant staphylococci. Antimicrob. Agents Chemother. 44:1394-6.

Donlan, R. M. 2002. Biofilms: microbial life on surfaces. Emerging Infectious Diseases. 8:881-890.

Donnenberg, M. S., and J. B. Kaper. 1991. Construction of an eae deletion mutant of enteropathogenic *Escherichia coli* by using a positive-selection suicide vector. Infect. Immun. 59:4310-4317.

Ehlers, L. J. 2000. Gene transfer in biofilms, p. 215-256. In D. G. Allison, P. Gilbert, H. M. Lappin-Scott, and M. Wilson (eds), Community structure and co-operation in biofilms. General Society for Microbiology, Cambridge.

Ena, J., J. R. Boelaert, L. D. Boyken, H. W. Van Landuyt, C. A. Godard, and L. A. Herwaldt. 1994. Epidemiology of *Staphylococcus aureus* infections in patients on hemodialysis. Infect Control Hosp Epidemiol. 15:78-81.

Fang, L., Z. Gan, and R. R. Marquardt. 2000. Isolation, affinity purification, and identification of piglet small intestine mucosa receptor for enterotoxigenic *Escherichia coli* k88ac+fimbriae. Infect. Immun. 68:564-9.

Farmer, J. J., 3rd, Asbury, M. A., Hickman, F. W., Brenner, D. J. and Group, E. S. (1980) International Journal of Systematic Bacteriology 30, 569-584.

Fett, W. F. 2000. Naturally occurring biofilms on alfalfa and other types of sprouts. J. Food Protection. 63:625-32.

Fischetti, V. A., Pancholi, V. and Schneewind, O. (1991) in: Genetics and molecular biology of *Streptococci, Lactococci* and *Enterococci*, pp. 290-294 (Dunny, G. M., Cleary, P. P. and McKay, L. L., Eds.) American Society for Microbiology, Washington, D.C.

Galperin, M. Y. 2004. Bacterial signal transduction network in a genomic perspective. Environ Microbiol. 6:552-67.

Galperin, M. Y., A. N. Nikolskaya, and E. V. Koonin. 2001. Novel domains of the prokaryotic two-component signal transduction systems. FEMS Microbiol. Lett. 203:11-21.

Geesey, D. G., A. M. Chakrabarty, and G. G. Geesey. 1993. Exopolysaccharide production in biofilms: substratum activation of alginate gene expressionby *Pseudomonas aeruginosa*. Appl Environ Microbiol. 59:1181-1186.

Gilbert, P., J. Das, and I. Foley. 1997. Biofilm susceptibility to antimicrobials. Adv Dent Res. 11:160-7.

Goodell, E. W. 1985. Recycling of murein by *Escherichia coli*. J Bacteriol. 163:305-10.

Goodell, E. W. and Schwarz, U. (1985) J Bacteriol 162, 391-7.

Götz, F. 2002. *Staphylococcus* and biofilms. Mol. Microbiol. 43:1367-1378.

Govan, J. R. W., and V. Deretic. 1996. Microbial pathogenesis in cystic fibrosis: mucoid *Pseudomonas aeruginosa* and *Burkholderia cepacia*. Microbiol Rev. 60:539-574.

Grobe, S., J. Wingender, and H. C. Flemming. 2001. Capability of mucoid *Pseudomonas aeruginosa* to survive in chlorinated water. Int J Hyg Environ Health. 204:139-142.

Güvener, Z. T. and McCarter, L. L. (2003) in: 103rd General Meeting of the American Society for Microbiology, Washington, D.C.

Hammer, B. K., and B. L. Bassler. 2003. Quorum sensing controls biofilm formation in *Vibrio cholerae*. Mol. Microbiol. 50:101-4.

Harlow, E., and D. Lane 1988. Antibodies: A laboratory manual. Cold Spring Harbor Laboratory. Cold Spring Harbor.

Haugo, A. J. and Watnick, P. I. (2002) Molecular Microbiology 45, 471-483.

Hayakawa, Y., R. Nagata, A. Hirata, M. Hyodo, and R. Kawai. 2003. A facile synthesis of cyclic bis(3'-5')diguanylic acid. Tetrahedron. 59:6465-6471.

Heidelberg, J. F., J. A. Eisen, W. C. Nelson, R. A. Clayton, M. L. Gwinn, R. J. Dodson, D. H. Haft, E. K. Hickey, J. D. Peterson, L. Umayam, S. R. Gill, K. E. Nelson, T. D. Read, H. Tettelin, D. Richardson, M. D. Ermolaeva, J. Vamathevan, S. Bass, H. Qin, I. Dragoi, P. Sellers, L. McDonald, T. Utterback, R. D. Fleishmann, W. C. Nierman, O. White, S. L. Salzberg, H. O. Smith, R. R. Colwell, J. J. Mekalanos, J. C. Venter, and F. C. M. 2000. DNA sequence of both chromosomes of the *cholera* pathogen *Vibrio cholerae*. Naure. 406:477-483.

Heidrich, C., Templin, M. F., Ursinus, A., Merdanovic, M., Berger, J., Schwarz, H., de Pedro, M. A. and Holtje, J. V. (2001) Molecular Microbiology 41, 167-78.

Heidrich, C., Ursinus, A., Berger, J., Schwarz, H. and Holtje, J. V. (2002) Journal of Bacteriology 184, 6093-6099.

Hermans, K., L. A. Devriese, and F. Haesebrouck. 2003. Rabbit staphylococcosis: difficult solutions for serious problems. Vet. Microbiol. 91:57-64.

Herrero, M., de Lorenzo, V. and Timmis, K. N. (1990) Journal of Bacteriology 172, 6557-6567.

Holtje, J. V. and Heidrich, C. (2001) Biochimie 83, 103-108.

Huang, S. S., and R. Platt. 2003. Risk of methicillin-resistant *Staphylococcus aureus* infection after previous infection or colonization. Clin Infect Dis. 36:281-5.

Huard, C., Miranda, G., Wessner, F., Bolotin, A., Hansen, J., Foster, S. J. and Chapot-Chartier, M. P. (2003) Microbiology 149, 695-705.

Hyde, J. A., R. O. Darouiche, and J. W. Costerton. 1998. Strategies for prophylaxis against prosthetic valve endocarditis: a review article. J Heart Valve Dis. 7:316-326.

Jackson, D. W., J. W. Simecka, and T. Romeo. 2002. Catabolite repression of *Escherichia coli* biofilm formation. J. Bacteriol. 184:3406-10.

Jenal, U. 2004. Cyclic di-guanosine-monophosphate comes of age: a novel secondary messenger involved in modulating cell surface structures in bacteria? Curr Opin Microbiol. 7:185-91.

Jobling, M. G. and Holmes, R. K. (1997) Molecular Microbiology 26, 1023-1034.

Jones, H. A., J. W. Lillard, Jr., and R. D. Perry. 1999. HmsT, a protein essential for expression of the haemin storage (Hms+) phenotype of *Yersinia pestis*. Microbiology. 145 (Pt 8):2117-28.

Jones, H. A., Lillard, J. W., Jr. and Perry, R. D. (1999) Microbiology 145 (Pt 8), 2117-28.

Kaper, J. B., Morris Jr., J. G. and Levine, M. M. (1995) Clinical Microbiology Reviews 8, 48-86.

Kern, D., Volkman, B. F., Luginbuhl, P., Nohaile, M. J., Kustu, S. and Wemmer, D. E. (1999) Nature 402, 894-8.

Kirmani, N., C. U. Tuazon, H. W. Murray, A. E. Parrish, and J. N. Sheagren. 1978. *Staphylococcus aureus* carriage rate of patients receiving long-term hemodialysis. Arch Intern Med. 138:1657-9.

Kluytmans, J., A. van Belkum, and H. Verbrugh. 1997. Nasal carriage of *Staphylococcus aureus*: epidemiology, underlying mechanisms, and associated risks. Clin. Microbiol. Rev. 10:505-20.

Laemmli, U. K. 1970. Cleavage of structural proteins during the assembly of the head of bacteriophage T4. Nature. 227:680-685.

Lamont, R. J., and H. F. Jenkinson. 1998. Life below the gum line: pathogenic mechanisms of *Porphyromonas gingivalis*. Microbiol Mol Biol Rev. 62:1244-1263.

Laupland, K. B., D. L. Church, M. Mucenski, L. R. Sutherland, and H. D. Davies. 2003. Population-based study of the epidemiology of and the risk factors for invasive *Staphylococcus aureus* infections. J. Infect. Dis. 187:1452-9.

Levine, M. M., Black, R. E., Clements, M. L., Nalin, D. R., Cisneros, L. and Finkelstein, R. A. (1981) in: Acute enteric infections in children. New prospects for treatment and prevention (Holme, T., Holmgreri, J., Merson, M. H. and Mollby, R., Eds.) Elsevier/North-Holland Biomedical Press, Amsterdam.

Lincoln, T. M., W. L. Dills, Jr., and J. D. Corbin. 1977. Purification and subunit composition of guanosine 3':5'-monophosphate-dependent protein kinase from bovine lung. J. Biol. Chem. 252:4269-75.

Lowy, F. D. 1998. *Staphylococcus aureus* infections. N. Engl. J. Med. 339:520-32.

Luzar, M. A., G. A. Coles, B. Faller, A. Slingeneyer, G. D. Dah, C. Briat, C. Wone, Y. Knefati, M. Kessler, and F.

Peluso. 1990. *Staphylococcus aureus* nasal carriage and infection in patients on continuous ambulatory peritoneal dialysis. N. Engl. J. Med. 322:505-9.

Maira-Litran, T., A. Kropec, C. Abeygunawardana, J. Joyce, G. Mark, 3rd, D. A. Goldmann, and G. B. Pier. 2002. Immunochemical properties of the staphylococcal poly-N-acetylglucosamine surface polysaccharide. Infect. Immun. 70:4433-40.

Matsuura, T., Y. Miyake, S. Nakashima, H. Komatsuzawa, Y. Akagawa, and H. Suginaka. 1996. Isolatiori and characterization of teichoic acid-lake substance as an adhesin of *Staphylococcus aureus* to HeLa cells. Microbiol. Immunol. 40:247-54.

Mayer, R., P. Ross, H. Weinhouse, D. Amikam, G. Volman, P. Ohana, R. D. Calhoon, H. C. Wong, A. W. Emerick, and M. Benziman. 1991. Polypeptide composition of bacterial cyclic diguanylic acid-dependent cellulose synthase and the occurrence of immunologically crossreacting proteins iri higher plants. Proc Natl Acad Sci U S A. 88:5472-6.

McCarthy, S. A., and F. M. Khambaty. 1994. International dissemination of epidemic *Vibrio cholerae* by cargo ship ballast and other nonpotable waters. Appl Environ Microbiol. 60:2597-2601.

McKenney, D., K. L. Pouliot, Y. Wang, V. Murthy, M. Ulrich, G. Doring, J. C. Lee, D. A. Goldmann, and G. B. Pier. 1999. Broadly protective vaccine for *Staphylococcus aureus* based on an in vivo-expressed antigen. Science. 284:1523-7.

Ménard, R., P. J. Sansonetti, and C. Parsot. 1993. Nonpolar mutagenesis of the ipa genes defines IpaB, IpaC, and IpaD as effectors of Shigella flexneri entry into epitheial cells. J. Bacteriol. 175:5899-5906.

Mest, D. R., D. H. Wong, K. J. Shimoda, M. E. Mulligan, and S. E. Wilson. 1994. Nasal colonization with methicillin-resistant *Staphylococcus aureus* on admission to the surgical intensive care unit increases the risk of infectiori. Anesth Analg. 78:644-50.

Miller, V. L. and Mekalanos, J. J. (1988.) Journal of Bacteriology 170, 2575-2583.

Miller, M. B., and B. L. Bassler (2001) Quorum sensing in bacteria, *Annu Rev Microbiol* 55:165-99.

Miller, M. B., K. Skorupski, D. H. Lenz, R. K. Taylor, and B. L. Bassler. 2002. Parallel Quorum Sensing Systems Converge to Regulate Virulence in *Vibrio cholerae*. Cell. 110: 303-314.

Miyake, Y., A. Kohada, I. Fujii, M. Sugai, and H. Suginaka. 1989. Aminoglycosides enhance the adherence of *Staphylococcus aureus* to HeLa cells. J Antimicrob Chemother. 23:79-86.

Miyake, Y., A. Kohada, M. Sugai, and H. Suginaka. 1991. Mechanism of aminoglycoside enhancement of *Staphylococcus aureus* adherence to HeLa cells. J Antimicrob Chemother. 28:811-7.

Morris Jr., J. G., M. B. Sztein, E. W. Rice, J. P. Nataro, G. A. Losonsky, P. Panigrahi, C. O. Tacket, and J. A. Johnson. 1996. *Vibrio cholerae* O1 can assume a chlorine-resistant rugose survival form that is virulent for humans. J Infect Dis. 174:1364-1368.

Muder, R. R., C. Brennen, M. M. Wagener, R. M. Vickers, J. D. Rihs, G. A. Hancock, Y. C. Yee, J. M. Miller, and V. L. Yu. 1991. Methicillin-resistant staphylococcal colonization and infection in a long-term care facility. Ann Intern Med. 114:107-12.

Muto, C. A., J. A. Jernigan, B. E. Ostrowsky, H. M. Richet, W. R. Jarvis, J. M. Boyce, and B. M. Farr. 2003. SHEA guideline for preventing nosocomial transmission of multidrug-resistant strains of *Staphylococcus aureus* and enterococcus. Infect Control Hosp Epidemiol. 24:362-86.

Nakajima, H., Y. U. Katagiri, N. Kiyokawa, T. Taguchi, T. Suzuki, T. Sekino, K. Mimori, M. Saito, H. Nakao, T. Takeda, and J. Fujimoto. 2001. Single-step method for purification of Shiga toxin-1 B subunit using receptor-mediated affinity chromatography by globotriaosylceramide-conjugated octyl sepharose CL-4B. Protein Expr Purif. 22:267-75.

National Nosocomial Infections Surveillance (NNIS) Report. 1998. Data summary from October 1986-April 1998, issued June 1998. Am J Infect Control. 26:522-33.

Nguyen, M. H., C. A. Kauffman, R. P. Goodman, C. Squier, R. D. Arbeit, N. Singh, M. M. Wagener, and V. L. Yu. 1999. Nasal carriage of and infection with *Staphylococcus aureus* in HIV-infected patients. Ann Intern Med. 130:221-5.

Nichols, W. W., S. M. Dorrington, M. P. Slack, and H. L. Walmsley. 1988. Inhibition of tobramycin diffusion by binding to alginate. Antimicrob Agents Chemother. 32:518-523.

Nickel, J. C., I. Ruseska, J. B. Wright, and J. W. Costerton. 1985. Tobramycin resistance of *Pseudomonas aeruginosa* cells growing as a biofilm on urinary catheter material. Antimicrob Agents Chemother. 27:619-624.

Notley-McRobb, L., A. Death, and T. Ferenci. 1997. The relationship between external glucose concentration and cAMP levels inside *Escherichia coli*: implications for models of phosphotransferase-mediated regulation of adenylate cyclase. Microbiology. 143 (Pt 6):1909-18.

Nunez, C., Moreno, S., Cardenas, L., Soberon-Chavez, G. and Espin, G. (2000) Journal of Bacteriology 182, 4829-4835.

Ott, S. L. 1999. Costs of herd-level production losses associated with subclinical mastitis in U.S. dairy cows. National Mastitis Council 38th Annual Meeting.

Park, J. T. (1993) J Bacteriol 175, 7-11.

Parkhill, J. et al. (2001) Nature 413, 523-7.

Parsek, M. R. 2003. The role of EPS in *Pseudomonas aeruginosa* biofilm structure and function. 103rd General meeting of the American Society for Microbiology, Washington, D.C.

Peacock, S. J., I. de Silva, and F. D. Lowy. 2001. What determines nasal carriage of *Staphylococcus aureus*? Trends Microbiol. 9:605-10.

Pei, J. and Grishin, N. V. (2001) Proteins 42, 210-6.

Petter, J. G. (1993) Appl Environ Microbiol 59, 2884-90.

Pollitzer, R. (1959) Monograph Series 43. Geneva: World Health Organization.

Pujol, M., C. Pena, R. Pallares, J. Ariza, J. Ayats, M. A. Dominguez, and F. Gudiol. 1996. Nosocomial *Staphylococcus aureus* bacteremia among nasal carriers of methicillin-resistant and methicillin-susceptible strains. Am J Med. 100:509-16.

Rajanna, C., J. Wang, D. Zhang, Z. Xu, A. Ali, Y.-M. Hou, and D. K. R. Karaolis. 2003. The Vibrio pathogenicity island of epidemic *Vibrio cholerae* forms precise extrachromosomal circular excision products. J. Bacteriol. 185:6893-6901.

Rashid, M. H., C. Rajanna, A. Ali, and D. K. R. Karaolis. 2003. Identification of genes involved in the switch between the smooth and rugose phenotypes of *Vibrio cholerae*. FEMS Microbiol. Letts. 227:113-119.

Raziuddin, S. 1980. Immunochemical studies of the lipopolysaccharides of *Vibrio cholerae*: constitution of O specific side chain and core polysaccharide. Infect Immun. 27:211-215.

Rice, E. W. et al. (1993) International Journal of Environmental Health Research 3, 89-98.

Richardson, K. (1991) Infection and Immunity 59, 2727-2736.

Richet, H. M., M. Benbachir, D. E. Brown, H. Giamarellou, I. Gould, M. Gubina, P. Heczko, S. Kalenic, M. Pana, D. Pittet, S. B. Redjeb, J. Schindler, C. Starling, M. J. Struelens, W. Witte, and W. R. Jarvis. 2003. Are there regional variations in the diagnosis, surveillance, and control of methicillin-resistant *Staphylococcus aureus*? Infect Control Hosp Epidemiol. 24:334-41.

Roche, F. M., M. Meehan, and T. J. Foster. 2003. The *Staphylococcus aureus* surface protein SasG and its homologues promote bacterial adherence to human desquamated nasal epithelial cells. Microbiology. 149:2759-67.

Roghmann, M. C., A. Siddiqui, K. Plaisance, and H. Standiford. 2001. MRSA colonization and the risk of MRSA bacteraemia in hospitalized patients with chronic ulcers. J Hosp Infect. 47:98-103.

Römling, U., M. Rohde, A. Olsen, S. Normark, and J. Reinkoster. 2000. AgfD, the checkpoint of multicellular and aggregative behaviour in *Salmonella typhimurium* regulates at least two independent pathways. Mol. Microbiol. 36:10-23.

Ross, P. et al. (1987) Nature 325, 279-281.

Ross, P., R. Mayer, and M. Benziman. 1991. Cellulose biosynthesis and function in bacteria. Microbiol. Rev. 55:35-58.

Ross, P., R. Mayer, H. Weinhouse, D. Amikam, Y. Huggirat, M. Benziman, E. de Vroom, A. Fidder, P. de Paus, L. A. Sliedregt, and et al. 1990. The cyclic diguanylic acid regulatory system of cellulose synthesis in *Acetobacter xylinum*. Chemical synthesis and biological activity of cyclic nucleotide dimer, trimer, and phosphothioate derivatives. J. Biol. Chem. 265:18933-43.

Ross, P., Y. Aloni, C. Weinhouse, D. Michaeli, P. Weinberger-Ohana, R. Meyer, and M. Benziman. 1991. An unusual guanyl oligonucleotide regulates cellulose synthesis in *Acetobacter xylinum*. FEBS Lett. 186:191-196.

Schauder, S., and B. L. Bassler (2001) The languages of bacteria, *Genes Dev* 15:1468-80.

Stark, R. M., G. J. Gerwig, R. S. Pitman, L. F. Potts, N. A. Williams, J. Greenman, I. P. Weinzweig, T. R. Hirst, and M. R. Millar. 1999. Biofilm formation by Helicobacter pylori. Lett. Appl. Microbiol. 28:121-126.

Steinberger, O., Z. Lapidot, Z. Ben-Ishai, and D. Amikam. 1999. Elevated expression of the CD4 receptor and cell cycle arrest are induced in Jurkat cells by treatment with the novel cyclic dinucleotide 3',5'-cyclic diguanylic acid. FEBS Lett. 444:125-9.

Sutra, L., and B. Poutrel. 1994. Virulence factors involved in the pathogenesis of bovine intramammary infections due to *Staphylococcus aureus*. J. Med. Microbiol. 40:79-89.

Tal, R. et al. (1998) Journal of Bacteriology 180, 4416-4425.

Tatusov, R. L., D. A. Natale, I. V. Garkavtsev, T. A. Tatusova, U. T. Shankavaram, B. S. Rao, B. Kiryutin, M. Y. Galperin, N. D. Fedorova, and E. V. Koonin. 2001. The COG database: new developments in phylogenetic classification of proteins from complete genomes. Nucl. Acids Res. 29:22-8.

Tsui, H. C., Zhao, G., Feng, G., Leung, H. C. and Winkler, M. E. (1994) Mol Microbiol 11, 189-202.

Tuazon, C. U., A. Perez, T. Kishaba, and J. N. Sheagren. 1975. *Staphylococcus aureus* among insulin-injecting diabetic patients. An increased carrier rate. Jama. 231:1272.

Tuazon, C. U., and J. N. Sheagren. 1974. Increased rate of carriage of *Staphylococcus aureus* among narcotic addicts. J. Infect. Dis. 129:725-7.

Tusher, V. G., R. Tibshirani, and G. Chu. 2001. Significance analysis of microarrays applied to the ionizing radiation response. Proc Natl Acad Sci U S A. 98:5116-21.

Valle, J., A. Toledo-Arana, C. Berasain, J. M. Ghigo, B. Amorena, J. R. Penades, and I. Lasa. 2003. SarA and not sigmaB is essential for biofilm development by *Staphylococcus aureus*. Mol. Microbiol. 48:1075-87.

von Eiff, C., K. Becker, K. Machka, H. Stammer, and G. Peters. 2001. Nasal carriage as a source of *Staphylococcus aureus* bacteremia. Study Group. N. Engl. J. Med. 344:11-6.

Wai, S. N., Y. Mizunoe, A. Takade, S. I. Kawabata, and S. I. Yoshida. 1998. *Vibrio cholerae* O1 strain TSI-4 produces the exopolysaccharide materials that determine colony morphology, stress resistance, and biofilm formation. Appl Environ Microbiol. 64:3648-3655.

Wang, R. F., and S. R. Kushner. 1999. Construction of versatile low-copy-number vectors for cloning, sequencing and gene expression in *Escherichia coli*. Gene. 100:195-199.

Watnick, P. I., and R. Kolter. 1999. Steps in the development of a *Vibrio cholerae* El Tor biofilm. Mol Microbiol. 34:586-595.

Watnick, P. I., and R. Kolter. 2000. Biofilm, city of microbes. J Bacteriol. 182:2675-2679.

Watnick, P. I., C. M. Lauriano, K. E. Klose, L. Croal, and R. Kolter. 2001. The absence of a flagellum leads to altered colony morphology, biofilm development and virulence in *Vibrio cholerae* O139. Mol Microbiol. 39:223-235.

White, P. B. 1938. The rugose variant of vibrios. Journal of Pathol. Bacteriol. 46:1-6.

White, P. B. 1940. The characteristic hapten and antigen of rugose races of *cholera* and El Tor vibrios. Journal of Pathol. Bacteriol. 50:160-164.

Whitehead, N. A., A. M. Barnard, H. Slater, N. J. Simpson, and G. P. Salmond (2001) Quorum sensing in Gram-negative bactria, *FEMS Microbiol Rev* 25:365-404.

Wimpenny, J. 2000. An overview of biofilms as functional communities, p. 1-24. In D. G. Allison, P. Gilbert, H. M. Lappin-Scott, and M. Wilson (eds), Community structure and co-operation in biofilms. Society for General Microbiology, Great Britain.

Wingender, J., T. R. Neu, and H.-C. Flemming 1999. What are bacterial extracellular polymeric substances? In J. Wingender, T. R. Neu, and H.-C. Flemming (eds), Microbial extracellular polymeric substances. Springer, Berlin.

Wolfinger, R. D., G. Gibson, E. D. Wolfinger, L. Ennett, H. Hamadeh, P. Bushel, C. Afshari, and R. S. Paules. 2001. Assessing gene significance from cDNA microarray expression data via mixed models. J. Computational Biolog. 6:625-637.

Wyatt, J. E., S. M. Poston, and W. C. Noble. 1990. Adherence of *Staphylococcus aureus* to cell monolayers. J. Appl. Bacteriol. 69:834-44.

Yancey, R. J., Willis, D. L. and Berry, L. J. (1978) Infection and Immunity 22, 387-392.

Yildiz, F. H., and G. K. Schoolnik. 1999. *Vibrio cholerae* O1 El Tor: identification of a gene cluster required for the rugose colony type, exopolysaccharide production, chlorine resistance, and biofilm formation. Proc Natl Acad Sci USA. 96:4028-4033.

Yildiz, F. H., and G. K. Schoolnik. 1999. *Vibrio cholerae* O1 El Tor: identification of a gene cluster required for the Yildiz, F. H., Dolganov, N. A. and Schoolnik, G. K. (2001) Journal of Bacteriology 183, 1716-1726.

Yu, V. L., A. Goetz, M. Wagener, P. B. Smith, J. D. Rihs, J. Hanchett, and J. J. Zuravleff. 1986. *Staphylococcus aureus* nasal carriage and infection in patients on hemodialysis. Efficacy of antibiotic prophylaxis. N. Engl. J. Med. 315: 91-6.

Zhang, D., Z. Xu, W. Sun, and D. K. Karaolis. 2003. The *Vibrio* Pathogenicity Island-Encoded Mop Protein Modulates the Pathogenesis and Reactogenicity of Epidemic *Vibrio cholerae*. Infect. Immun. 71:510-515.

Zhu, J., M. B. Miller, R. E. Vance, M. Dziejman, B. L. Bassler, and J. J. Mekalanos. 2002. Quorum sensing regulators control virulence gene expression in *Vibrio cholerae*. Proc. Natl. Acad. Sci. USA. 99:3129-3134.

What is claimed is:

1. A method for attenuating the virulence of a bacterial pathogen or for inhibiting or reducing colonization by a bacterial pathogen in a patient in need thereof, comprising administering to the patient in need an effective amount of c-di-GMP to attenuate the virulence of, or to inhibit or reduce colonization by, the bacterial pathogen, wherein the bacterial pathogen is selected from the group consisting of *Staphylococcus aureus, Klebsiella pneumoniae*, and *Streptococcus pneumoniae*.

2. The method of claim 1, wherein the attenuation of the virulence of the bacterial pathogens pathogen comprises treating bacterial infection by the pathogen.

3. The method of claim 2, wherein said bacterial infection is mastitis, a *Staphylococcus aureus* infection of the mammary gland.

4. The method of claim 2, wherein said bacterial infection is treated by inhibiting bacterial biofilm formation or by reducing the bacterial biofilm already formed.

5. The method of claim 4, wherein said bacterial biofilm is on the skin or on a nasal or mucosal surface.

6. The method of claim 2, further comprising administering an antibiotic compound which effective in treating said bacterial infection.

7. The method of claim 1, wherein the inhibition or reduction of colonization of a bacterial pathogen comprises treating a patient at risk of being colonized by the bacterial pathogen or a patient already colonized by the bacterial pathogen.

8. The method of claim 7, wherein the colonization of the bacterial pathogen that is inhibited or reduced is on the skin or on a nasal or mucosal surface.

9. The method of claim 7, wherein said patient is a carrier of *Staphylococcus aureus*.

10. A method for inhibiting bacterial colonization and biofilm formation or for reducing bacterial colonization and pre-formed biofilm on a solid surface, comprising exposing the solid surface to an effective amount of c-di-GMP to inhibit bacterial colonization and biofilm formation or to reduce bacterial colonization and pre-formed biofilm on said solid surface, wherein the bacterial colonization and biofilm is formed by a bacterial pathogen selected from the group consisting of *Staphylococcus aureus, Pseudomonas aeruginosa*, and *Vibrio parahaemolyticus*.

11. The method of claim 10, wherein said solid surface is a solid surface of a medical device.

12. The method of claim 11, wherein said medical device is implantable in or capable of attaching to a patient.

13. The method of claim 11, wherein said medical device is implanted in a patient or otherwise in contact with a patient.

14. The method of claim 1, wherein said patient in need thereof is a mammal.

15. The method of claim 1, wherein said patient in need thereof is human.

16. The method of claim 1, wherein said patient in need thereof is a bird.

17. The method of claim 2, wherein said bacterial infection is a *Staphylococcus aureus* infection.

18. The method of claim 4, wherein said bacterial biofilm is a *Staphylococcus aureus* biofilm.

19. The method of claim 7, wherein said bacterial pathogen is *Staphylococcus aureus*.

20. The method of claim 1, wherein said bacterial pathogen is *Staphylococcus aureus*.

21. The method of claim 1, wherein said bacterial pathogen is *Klebsiella pneumoniae*.

22. The method of claim 1, wherein said bacterial pathogen is *Streptococcus pneumoniae*.

23. The method of claim 5, wherein said bacterial biofilm is a *Staphylococcus aureus* biofilm.

24. The method of claim 10, wherein the bacterial colonization and biofilm is *Staphylococcus aureus* colonization and biofilm.

25. The method of claim 10, wherein the bacterial colonization and biofilm is *Pseudomonas aeruginosa* colonization and biofilm.

26. The method of claim 10, wherein the bacterial colonization and biofilm is *Vibrio parahaemolyticus* colonization and biofilm.

* * * * *

UNITED STATES PATENT AND TRADEMARK OFFICE
CERTIFICATE OF CORRECTION

PATENT NO. : 8,367,716 B2 Page 1 of 1
APPLICATION NO. : 10/565591
DATED : February 5, 2013
INVENTOR(S) : David K. R. Karaolis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 619 days.

Signed and Sealed this
First Day of September, 2015

Michelle K. Lee
*Director of the United States Patent and Trademark Office*

SEQUENCE LISTING

<160> NUMBER OF SEQ ID NOS: 5

<210> SEQ ID NO 1
<211> LENGTH: 2055
<212> TYPE: DNA
<213> ORGANISM: V. cholerae
<220> FEATURE:
<221> NAME/KEY: CDS
<222> LOCATION: (1)..(2055)

<400> SEQUENCE: 1

```
atg cct gct caa acc tca tct cag ctc aag cat tgg ttt gca aaa att       48
Met Pro Ala Gln Thr Ser Ser Gln Leu Lys His Trp Phe Ala Lys Ile
1               5                   10                  15 acg tca cac agt ccg ttc ttt ttt gca atc ctc aat gat caa cac caa       96
Thr Ser His Ser Pro Phe Phe Phe Ala Ile Leu Asn Asp Gln His Gln
            20                  25                  30 tac gtg atg gtc aac gag cgc tat tgt gat atc gcc ggt ctc tct agc      144
Tyr Val Met Val Asn Glu Arg Tyr Cys Asp Ile Ala Gly Leu Ser Ser
        35                  40                  45 gaa gag atg gtc ggg atg agc gat agt cag gtt ctg ggc gaa cat ttt      192
Glu Glu Met Val Gly Met Ser Asp Ser Gln Val Leu Gly Glu His Phe
    50                  55                  60 tat cgc cat ctc aaa ccg ttt tac gaa cgt gcg ttt aac aac gag cat      240
Tyr Arg His Leu Lys Pro Phe Tyr Glu Arg Ala Phe Asn Asn Glu His
65                  70                  75                  80 att gag tcc gag ctg acc ctc agc gaa atc gac ctc gaa acc agc tta      288
Ile Glu Ser Glu Leu Thr Leu Ser Glu Ile Asp Leu Glu Thr Ser Leu
                85                  90                  95 cac ttt tct ctc tcc ccc atc atg atc aac gat cgg gtg caa tac ctt      336
His Phe Ser Leu Ser Pro Ile Met Ile Asn Asp Arg Val Gln Tyr Leu
            100                 105                 110 gta ttc cac gcg att gat acc tca gaa aag cag att tta gtg cgc tct      384
Val Phe His Ala Ile Asp Thr Ser Glu Lys Gln Ile Leu Val Arg Ser
        115                 120                 125 ctg gaa gaa tcg gaa agc aaa tac gca ctc ctc acg aca ctg cta cct      432
Leu Glu Glu Ser Glu Ser Lys Tyr Ala Leu Leu Thr Thr Leu Leu Pro
    130                 135                 140 gat ggt tta atg atg gtg gaa aat gac tgc att att tct gcc aac cct      480
Asp Gly Leu Met Met Val Glu Asn Asp Cys Ile Ile Ser Ala Asn Pro
145                 150                 155                 160 tcc gct gca cgt tta ctc ggt ttt gac gac gca caa aaa ctg ctc gga      528
Ser Ala Ala Arg Leu Leu Gly Phe Asp Asp Ala Gln Lys Leu Leu Gly
                165                 170                 175 gaa aat ctc tcc aga ctg ttt att gat gaa aag acc aaa acc gtt ttt      576
Glu Asn Leu Ser Arg Leu Phe Ile Asp Glu Lys Thr Lys Thr Val Phe
            180                 185                 190 tca tcg cag ttg gct tcg cta ctg aca gaa aaa ccc ttg gtg tgc ttg      624
Ser Ser Gln Leu Ala Ser Leu Leu Thr Glu Lys Pro Leu Val Cys Leu
        195                 200                 205
```

```
acc ggg cca agg tgt ggg ttt gaa cgg aaa atc cag tta cac gca ggt      672
Thr Gly Pro Arg Cys Gly Phe Glu Arg Lys Ile Gln Leu His Ala Gly
    210                 215                 220 tgc acc tct tta ctc ggt aat cag tcg cag ttg atc tta ttg caa gat      720
Cys Thr Ser Leu Leu Gly Asn Gln Ser Gln Leu Ile Leu Leu Gln Asp
225                 230                 235                 240 gcc gat gaa gcc cca aaa cag ttt tct gcg acc act caa gtc gat gcg      768
Ala Asp Glu Ala Pro Lys Gln Phe Ser Ala Thr Thr Gln Val Asp Ala
                245                 250                 255 cat att gat agc ctc act ggg ctg tat aac cga cac ggg ttt acc aag      816
His Ile Asp Ser Leu Thr Gly Leu Tyr Asn Arg His Gly Phe Thr Lys
            260                 265                 270 cgc tta gag cag tgc atc caa aat gag acg cct ttg gtt atg ctc tat      864
Arg Leu Glu Gln Cys Ile Gln Asn Glu Thr Pro Leu Val Met Leu Tyr
        275                 280                 285 ctg gac att gat aac ttc aaa aac atc aat gac tct ctc ggc cat cac      912
Leu Asp Ile Asp Asn Phe Lys Asn Ile Asn Asp Ser Leu Gly His His
    290                 295                 300 atc ggt gac aaa gtg att aaa gag gtg gcg gca cgt tta aaa cgc tta      960
Ile Gly Asp Lys Val Ile Lys Glu Val Ala Ala Arg Leu Lys Arg Leu
305                 310                 315                 320 ctg cca cag caa gcc gta ctt ggc cat ttg ggc ggt gat gag ttt ggt     1008
Leu Pro Gln Gln Ala Val Leu Gly His Leu Gly Gly Asp Glu Phe Gly
                325                 330                 335 ttg atc ttg ccg gag cca gaa cac aac cgc tct gca gaa atg ttg gca     1056
Leu Ile Leu Pro Glu Pro Glu His Asn Arg Ser Ala Glu Met Leu Ala
            340                 345                 350 gat cgc att atc tct ttg att aat cag cct ttt gac ctg cac cat ttc     1104
Asp Arg Ile Ile Ser Leu Ile Asn Gln Pro Phe Asp Leu His His Phe
        355                 360                 365 agt aag cgt tta gct tgt tcg att ggc agc gtg cgt tat ccc ggt gac     1152
Ser Lys Arg Leu Ala Cys Ser Ile Gly Ser Val Arg Tyr Pro Gly Asp
    370                 375                 380 ggc aat gat gct cgc gta tta ctg caa aat gcc gat acc gcg atg tat     1200
Gly Asn Asp Ala Arg Val Leu Leu Gln Asn Ala Asp Thr Ala Met Tyr
385                 390                 395                 400 gag gct aaa gag cgc ggt cgc aat cgc ctg atc aaa ttc aat gat cag     1248
Glu Ala Lys Glu Arg Gly Arg Asn Arg Leu Ile Lys Phe Asn Asp Gln
                405                 410                 415 atg aac aaa gaa gcg cgg atg cgc ctt tgg ttg gaa att gaa ctg caa     1296
Met Asn Lys Glu Ala Arg Met Arg Leu Trp Leu Glu Ile Glu Leu Gln
            420                 425                 430 aaa gcg cta caa caa aac ggc cta gaa gtg tgg tac caa ccg aaa gtc     1344
Lys Ala Leu Gln Gln Asn Gly Leu Glu Val Trp Tyr Gln Pro Lys Val
        435                 440                 445 aac gcg cgt gat ttt agc atc aat ggc gca gaa gcc ttg gta cgc tgg     1392
Asn Ala Arg Asp Phe Ser Ile Asn Gly Ala Glu Ala Leu Val Arg Trp
    450                 455                 460 aaa cat ccc gtt gaa ggc tat atc agc cca ggt gct ttc att ccc gtt     1440
Lys His Pro Val Glu Gly Tyr Ile Ser Pro Gly Ala Phe Ile Pro Val
465                 470                 475                 480 gcg gaa aaa gcc ggc tta atc gaa cat ttg ggt cgc gtg gtt atg cgt     1488
Ala Glu Lys Ala Gly Leu Ile Glu His Leu Gly Arg Val Val Met Arg
                485                 490                 495 gaa gtc ttc gcg acc gtc aag cgc tgg aag cta caa ggc att tta ccc     1536
Glu Val Phe Ala Thr Val Lys Arg Trp Lys Leu Gln Gly Ile Leu Pro
            500                 505                 510 gga cgt gtg gcg atc aac atc tcc ccc gag cag ttt ggc aat cct caa     1584
Gly Arg Val Ala Ile Asn Ile Ser Pro Glu Gln Phe Gly Asn Pro Gln
        515                 520                 525
```

```
ctg att gat tat tta gaa aaa cta ctg cga aca act ggg cta gat ccc     1632
Leu Ile Asp Tyr Leu Glu Lys Leu Leu Arg Thr Thr Gly Leu Asp Pro
    530                 535                 540 aac aac atc aca ttt gaa ctg acc gaa agt gtg gtg atg agc gat agt     1680
Asn Asn Ile Thr Phe Glu Leu Thr Glu Ser Val Val Met Ser Asp Ser
545                 550                 555                 560 gaa cat acc cag caa atg ctc aat gcc atc aag aaa ctc ggc ttc acc     1728
Glu His Thr Gln Gln Met Leu Asn Ala Ile Lys Lys Leu Gly Phe Thr
                565                 570                 575 ttg tca att gat gac ttc ggt aca ggt tac tcg tcg ctg gct tat tta     1776
Leu Ser Ile Asp Asp Phe Gly Thr Gly Tyr Ser Ser Leu Ala Tyr Leu
            580                 585                 590 gct cgc ttc ccg atc gat gag ctc aaa atc gac cgc gcg ttt atc agt     1824
Ala Arg Phe Pro Ile Asp Glu Leu Lys Ile Asp Arg Ala Phe Ile Ser
        595                 600                 605 aat atc gac act cta ccc aaa cag ctc acg gtg att gaa aac atc att     1872
Asn Ile Asp Thr Leu Pro Lys Gln Leu Thr Val Ile Glu Asn Ile Ile
    610                 615                 620 aat ttg ggg cgc tca ctg aac ctg acc gta gtt gca gaa gga gta gaa     1920
Asn Leu Gly Arg Ser Leu Asn Leu Thr Val Val Ala Glu Gly Val Glu
625                 630                 635                 640 act cag caa caa gcc act tta ctc tcc aac cta aat tgc cac tcc atc     1968
Thr Gln Gln Gln Ala Thr Leu Leu Ser Asn Leu Asn Cys His Ser Ile
                645                 650                 655 caa ggc ttc cat ttt tat cgc cca caa ccg aag cac gaa gtg gaa gag     2016
Gln Gly Phe His Phe Tyr Arg Pro Gln Pro Lys His Glu Val Glu Glu
            660                 665                 670 ttg ttt gcg caa aat cgc cgc cat cgc aaa tcc ctc taa                 2055
Leu Phe Ala Gln Asn Arg Arg His Arg Lys Ser Leu
        675                 680
```

<210> SEQ ID NO 2
<211> LENGTH: 684
<212> TYPE: PRT
<213> ORGANISM: V. cholerae

<400> SEQUENCE: 2

```
Met Pro Ala Gln Thr Ser Ser Gln Leu Lys His Trp Phe Ala Lys Ile
1               5                   10                  15

Thr Ser His Ser Pro Phe Phe Phe Ala Ile Leu Asn Asp Gln His Gln
            20                  25                  30

Tyr Val Met Val Asn Glu Arg Tyr Cys Asp Ile Ala Gly Leu Ser Ser
        35                  40                  45

Glu Glu Met Val Gly Met Ser Asp Ser Gln Val Leu Gly Glu His Phe
    50                  55                  60

Tyr Arg His Leu Lys Pro Phe Tyr Glu Arg Ala Phe Asn Asn Glu His
65                  70                  75                  80

Ile Glu Ser Glu Leu Thr Leu Ser Glu Ile Asp Leu Glu Thr Ser Leu
                85                  90                  95

His Phe Ser Leu Ser Pro Ile Met Ile Asn Asp Arg Val Gln Tyr Leu
            100                 105                 110

Val Phe His Ala Ile Asp Thr Ser Glu Lys Gln Ile Leu Val Arg Ser
        115                 120                 125

Leu Glu Glu Ser Glu Ser Lys Tyr Ala Leu Leu Thr Thr Leu Leu Pro
    130                 135                 140

Asp Gly Leu Met Met Val Glu Asn Asp Cys Ile Ile Ser Ala Asn Pro
145                 150                 155                 160

Ser Ala Ala Arg Leu Leu Gly Phe Asp Asp Ala Gln Lys Leu Leu Gly
                165                 170                 175
```

-continued

Glu Asn Leu Ser Arg Leu Phe Ile Asp Glu Lys Thr Lys Thr Val Phe
            180                 185                 190

Ser Ser Gln Leu Ala Ser Leu Leu Thr Glu Lys Pro Leu Val Cys Leu
        195                 200                 205

Thr Gly Pro Arg Cys Gly Phe Glu Arg Lys Ile Gln Leu His Ala Gly
    210                 215                 220

Cys Thr Ser Leu Leu Gly Asn Gln Ser Gln Leu Ile Leu Leu Gln Asp
225                 230                 235                 240

Ala Asp Glu Ala Pro Lys Gln Phe Ser Ala Thr Thr Gln Val Asp Ala
                245                 250                 255

His Ile Asp Ser Leu Thr Gly Leu Tyr Asn Arg His Gly Phe Thr Lys
            260                 265                 270

Arg Leu Glu Gln Cys Ile Gln Asn Glu Thr Pro Leu Val Met Leu Tyr
        275                 280                 285

Leu Asp Ile Asp Asn Phe Lys Asn Ile Asn Asp Ser Leu Gly His His
    290                 295                 300

Ile Gly Asp Lys Val Ile Lys Glu Val Ala Ala Arg Leu Lys Arg Leu
305                 310                 315                 320

Leu Pro Gln Gln Ala Val Leu Gly His Leu Gly Gly Asp Glu Phe Gly
                325                 330                 335

Leu Ile Leu Pro Glu Pro Glu His Asn Arg Ser Ala Glu Met Leu Ala
            340                 345                 350

Asp Arg Ile Ile Ser Leu Ile Asn Gln Pro Phe Asp Leu His His Phe
        355                 360                 365

Ser Lys Arg Leu Ala Cys Ser Ile Gly Ser Val Arg Tyr Pro Gly Asp
    370                 375                 380

Gly Asn Asp Ala Arg Val Leu Leu Gln Asn Ala Asp Thr Ala Met Tyr
385                 390                 395                 400

Glu Ala Lys Glu Arg Gly Arg Asn Arg Leu Ile Lys Phe Asn Asp Gln
                405                 410                 415

Met Asn Lys Glu Ala Arg Met Arg Leu Trp Leu Glu Ile Glu Leu Gln
            420                 425                 430

Lys Ala Leu Gln Gln Asn Gly Leu Glu Val Trp Tyr Gln Pro Lys Val
        435                 440                 445

Asn Ala Arg Asp Phe Ser Ile Asn Gly Ala Glu Ala Leu Val Arg Trp
    450                 455                 460

Lys His Pro Val Glu Gly Tyr Ile Ser Pro Gly Ala Phe Ile Pro Val
465                 470                 475                 480

Ala Glu Lys Ala Gly Leu Ile Glu His Leu Gly Arg Val Val Met Arg
                485                 490                 495

Glu Val Phe Ala Thr Val Lys Arg Trp Lys Leu Gln Gly Ile Leu Pro
            500                 505                 510

Gly Arg Val Ala Ile Asn Ile Ser Pro Glu Gln Phe Gly Asn Pro Gln
        515                 520                 525

Leu Ile Asp Tyr Leu Glu Lys Leu Leu Arg Thr Thr Gly Leu Asp Pro
    530                 535                 540

Asn Asn Ile Thr Phe Glu Leu Thr Glu Ser Val Val Met Ser Asp Ser
545                 550                 555                 560

Glu His Thr Gln Gln Met Leu Asn Ala Ile Lys Lys Leu Gly Phe Thr
                565                 570                 575

Leu Ser Ile Asp Asp Phe Gly Thr Gly Tyr Ser Ser Leu Ala Tyr Leu
            580                 585                 590

Ala Arg Phe Pro Ile Asp Glu Leu Lys Ile Asp Arg Ala Phe Ile Ser

-continued

```
                595                 600                 605
Asn Ile Asp Thr Leu Pro Lys Gln Leu Thr Val Ile Glu Asn Ile Ile
        610                 615                 620

Asn Leu Gly Arg Ser Leu Asn Leu Thr Val Val Ala Glu Gly Val Glu
625                 630                 635                 640

Thr Gln Gln Gln Ala Thr Leu Leu Ser Asn Leu Asn Cys His Ser Ile
                645                 650                 655

Gln Gly Phe His Phe Tyr Arg Pro Gln Pro Lys His Glu Val Glu Glu
                660                 665                 670

Leu Phe Ala Gln Asn Arg Arg His Arg Lys Ser Leu
        675                 680

<210> SEQ ID NO 3
<211> LENGTH: 31
<212> TYPE: DNA
<213> ORGANISM: Artificial
<220> FEATURE:
<223> OTHER INFORMATION: synthetic

<400> SEQUENCE: 3
cgggatcccg ctaagtcaga gtttttatcg c                              31

<210> SEQ ID NO 4
<211> LENGTH: 29
<212> TYPE: DNA
<213> ORGANISM: Artificial
<220> FEATURE:
<223> OTHER INFORMATION: synthetic

<400> SEQUENCE: 4
tccccgcggg tcggtggttt tgatcgtgt                                 29

<210> SEQ ID NO 5
<211> LENGTH: 5
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: Residue at this position can be either Asp or
      Glu.

<400> SEQUENCE: 5

Gly Gly Xaa Glu Phe
1               5
```